(12) United States Patent
Altshuler et al.

(10) Patent No.: US 8,182,473 B2
(45) Date of Patent: May 22, 2012

(54) COOLING SYSTEM FOR A PHOTOCOSMETIC DEVICE

(75) Inventors: Gregory B. Altshuler, Wilmington, MA (US); Joseph P. Caruso, Reading, MA (US); Henry H. Zenzie, Dover, MA (US); James G. Burke, III, Londonderry, NH (US); Andrei V. Erofeev, N. Andover, MA (US)

(73) Assignee: Palomar Medical Technologies, Burlington, MA (US)

( * ) Notice: Subject to any disclaimer, the term of this patent is extended or adjusted under 35 U.S.C. 154(b) by 1400 days.

(21) Appl. No.: 11/603,712

(22) Filed: Nov. 22, 2006

(65) Prior Publication Data

US 2007/0129711 A1    Jun. 7, 2007

Related U.S. Application Data

(63) Continuation of application No. 10/154,756, filed on May 23, 2002, now Pat. No. 7,204,832, and a continuation-in-part of application No. 10/052,474, filed on Jan. 18, 2002, now Pat. No. 6,663,620, which is a continuation of application No. 09/473,910, filed on Dec. 28, 1999, now Pat. No. 6,517,532, and a continuation-in-part of application No. 09/078,055, filed on May 13, 1998, now Pat. No. 6,273,884, which is a continuation-in-part of application No. 09/268,433, filed on Mar. 12, 1999, now Pat. No.

(Continued)

(51) Int. Cl.
   *A61B 18/18*     (2006.01)
(52) U.S. Cl. .................... 606/9; 607/89; 606/13

(58) Field of Classification Search .................. None
   See application file for complete search history.

(56) References Cited

U.S. PATENT DOCUMENTS 853,033 A    5/1907 Roberts (Continued)

FOREIGN PATENT DOCUMENTS

AT    400305    12/1995

(Continued)

OTHER PUBLICATIONS

A. V. Belikov et al., "Indentification of enamel and dentine under tooth laser treatment," SPIE vol. 2623, Progress in Biomedical Optics Europt Series, Proceedings of Medical Applications of Lasers III, pp. 109-116, Sep. 1995.

(Continued)

*Primary Examiner* — Henry M Johnson, III
*Assistant Examiner* — Lynsey Crandall
(74) *Attorney, Agent, or Firm* — Wilmer Cutler Pickering Hale and Dorr LLP

(57) ABSTRACT

Photocosmetic device for use in medical or non-medical environments (e.g., a home, barbershop, or spa), which can be used for a variety of tissue treatments. Radiation is delivered to the tissue via optical systems designed to pattern the radiation and project the radiation to a particular depth. The device has a variety of cooling systems including phase change cooling solids and liquids to cool treated skin and the radiation sources. Contact sensors and motion sensor may be used to enhance treatment. The device may be modular to facilitate manufacture and replacement of parts.

16 Claims, 25 Drawing Sheets

Related U.S. Application Data 6,508,813, which is a continuation-in-part of application No. 08/759,036, filed on Dec. 2, 1996, now Pat. No. 6,015,404, and a continuation-in-part of application No. 08/759,136, filed on Dec. 2, 1996, now abandoned, which is a continuation-in-part of application No. 09/634,981, filed on Aug. 9, 2000, now Pat. No. 6,511,475, which is a continuation-in-part of application No. 09/847,043, filed on Apr. 30, 2001, now Pat. No. 6,653,618.

(60) Provisional application No. 60/363,798, filed on Mar. 12, 2002, provisional application No. 60/115,447, filed on Jan. 8, 1999, provisional application No. 60/164,492, filed on Nov. 9, 1999, provisional application No. 60/046,542, filed on May 15, 1997, provisional application No. 60/077,794, filed on Jan. 8, 1999, provisional application No. 60/077,726, filed on Mar. 12, 1998, provisional application No. 60/200,431, filed on Apr. 28, 2000, provisional application No. 60/292,827, filed on May 23, 2001, provisional application No. 60/363,871, filed on Mar. 12, 2002.

(56) References Cited

U.S. PATENT DOCUMENTS

| | | |
|---|---|---|
| 1,590,283 A | 6/1926 | Catlin |
| 1,706,161 A | 3/1929 | Hollnagel |
| 2,472,385 A | 6/1949 | Rollman |
| 2,669,771 A | 2/1954 | Burge et al. |
| 3,261,978 A | 7/1966 | Brennan |
| 3,327,712 A | 6/1967 | Kaufman et al. |
| 3,486,070 A | 12/1969 | Engel |
| 3,527,932 A | 9/1970 | Thomas |
| 3,538,919 A | 11/1970 | Meyer |
| 3,597,652 A | 8/1971 | Gates, Jr. |
| 3,622,743 A | 11/1971 | Muncheryan |
| 3,653,778 A | 4/1972 | Freiling |
| 3,667,454 A | 6/1972 | Prince |
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |
| 3,857,015 A | 12/1974 | Clark et al. |
| 3,890,537 A | 6/1975 | Park et al. |
| 3,900,034 A | 8/1975 | Katz et al. |
| 3,909,649 A | 9/1975 | Arsena |
| 3,939,560 A | 2/1976 | Lyall |
| 3,977,083 A | 8/1976 | Leslie et al. |
| 4,047,106 A | 9/1977 | Robinson |
| 4,213,462 A | 7/1980 | Sato et al. |
| 4,232,678 A | 11/1980 | Skovajsa et al. |
| 4,233,493 A | 11/1980 | Nath et al. |
| 4,269,067 A | 5/1981 | Tynan et al. |
| 4,273,109 A | 6/1981 | Enderby |
| 4,275,335 A | 6/1981 | Ishida et al. |
| 4,298,005 A | 11/1981 | Mutzhas |
| 4,316,467 A | 2/1982 | Muckerheide |
| 4,333,197 A | 6/1982 | Kuris |
| 4,335,726 A | 6/1982 | Kolstedt |
| 4,388,924 A | 6/1983 | Weissman et al. |
| 4,409,479 A | 10/1983 | Sprague et al. |
| 4,452,081 A | 6/1984 | Seppi |
| 4,456,872 A | 6/1984 | Froeschle |
| 4,461,294 A | 7/1984 | Baron |
| 4,504,727 A | 3/1985 | Melcher et al. |
| 4,512,197 A | 4/1985 | von Gutfeld et al. |
| 4,524,289 A | 6/1985 | Hammond et al. |
| 4,539,987 A | 9/1985 | Nath et al. |
| 4,553,546 A | 11/1985 | Javelle et al. |
| 4,561,440 A | 12/1985 | Kubo et al. |
| 4,566,271 A | 1/1986 | French et al. |
| 4,591,762 A | 5/1986 | Nakamura et al. |
| 4,601,753 A | 7/1986 | Soileau et al. |
| 4,608,978 A | 9/1986 | Rohr |
| 4,608,979 A | 9/1986 | Breidenthal et al. |
| 4,617,926 A * | 10/1986 | Sutton .................. 606/9 |
| 4,623,929 A | 11/1986 | Johnson et al. |
| 4,653,495 A | 3/1987 | Nanaumi |
| 4,677,347 A | 6/1987 | Nakamura |
| 4,686,986 A | 8/1987 | Fenyo et al. |
| 4,695,697 A | 9/1987 | Kosa |
| 4,710,677 A | 12/1987 | Halberstadt et al. |
| 4,718,416 A | 1/1988 | Nanaumi et al. |
| 4,733,660 A | 3/1988 | Itzkan |
| 4,736,745 A | 4/1988 | Gluckman |
| 4,745,909 A | 5/1988 | Pelton et al. |
| 4,747,660 A | 5/1988 | Nishioka et al. |
| 4,749,913 A | 6/1988 | Stuermer et al. |
| 4,775,361 A | 10/1988 | Jacques et al. |
| 4,779,173 A | 10/1988 | Carr et al. |
| 4,784,135 A | 11/1988 | Blum et al. |
| 4,799,479 A | 1/1989 | Spears |
| 4,808,789 A * | 2/1989 | Muncheryan .............. 219/121.6 |
| 4,819,669 A | 4/1989 | Politzer et al. |
| 4,826,431 A | 5/1989 | Fujimura et al. |
| 4,832,024 A | 5/1989 | Boussignac et al. |
| 4,840,174 A | 6/1989 | Gluckman |
| 4,845,608 A | 7/1989 | Gdula |
| 4,852,549 A | 8/1989 | Mori |
| 4,860,172 A | 8/1989 | Schlager et al. |
| 4,860,744 A | 8/1989 | Johnson et al. |
| 4,862,903 A | 9/1989 | Campbell |
| 4,871,479 A | 10/1989 | Bachelard et al. |
| 4,884,560 A | 12/1989 | Kuracina |
| 4,898,438 A | 2/1990 | Mori |
| 4,905,690 A | 3/1990 | Ohshiro et al. |
| 4,914,298 A | 4/1990 | Quad et al. |
| 4,917,084 A | 4/1990 | Sinofsky |
| 4,926,227 A | 5/1990 | Jensen |
| 4,928,038 A | 5/1990 | Nerone |
| 4,930,504 A | 6/1990 | Diamantopoulos et al. |
| 4,932,954 A | 6/1990 | Wondrazek et al. |
| 4,945,239 A | 7/1990 | Wist et al. |
| 4,973,848 A | 11/1990 | Kolobanov et al. |
| 4,976,308 A | 12/1990 | Faghri |
| 4,992,256 A | 2/1991 | Skaggs et al. |
| 5,000,752 A | 3/1991 | Hoskin et al. |
| 5,030,090 A | 7/1991 | Maeda et al. |
| 5,032,178 A | 7/1991 | Cornell |
| 5,046,494 A | 9/1991 | Searfoss et al. |
| 5,050,597 A | 9/1991 | Daikuzono |
| 5,057,104 A | 10/1991 | Chess |
| 5,059,192 A | 10/1991 | Zaias |
| 5,065,515 A * | 11/1991 | Iderosa .................. 30/140 |
| 5,066,293 A | 11/1991 | Furumoto |
| 5,071,417 A | 12/1991 | Sinofsky |
| 5,074,661 A | 12/1991 | Reynolds et al. |
| 5,074,861 A | 12/1991 | Schneider et al. |
| 5,099,910 A | 3/1992 | Walpole et al. |
| 5,108,388 A | 4/1992 | Trokel |
| 5,127,395 A | 7/1992 | Bontemps et al. |
| 5,133,102 A | 7/1992 | Sakuma |
| 5,137,530 A | 8/1992 | Sand |
| 5,140,984 A | 8/1992 | Dew et al. |
| 5,159,601 A | 10/1992 | Huber |
| 5,160,194 A | 11/1992 | Feldman |
| 5,171,564 A | 12/1992 | Nathoo et al. |
| 5,178,617 A | 1/1993 | Kuizenga et al. |
| 5,182,557 A | 1/1993 | Lang |
| 5,182,857 A * | 2/1993 | Simon .................. 30/34.05 |
| 5,192,278 A | 3/1993 | Hayes et al. |
| 5,196,004 A | 3/1993 | Sinofsky |
| 5,207,671 A | 5/1993 | Franken et al. |
| 5,220,804 A | 6/1993 | Tilton et al. |
| 5,222,907 A | 6/1993 | Katabuchi et al. |
| 5,225,926 A | 7/1993 | Cuomo et al. |
| 5,226,907 A | 7/1993 | Tankovich |
| 5,267,399 A | 12/1993 | Johnston |
| 5,281,211 A | 1/1994 | Parel et al. |
| 5,282,797 A | 2/1994 | Chess |
| 5,287,372 A | 2/1994 | Ortiz |

| | | |
|---|---|---|
| 5,287,380 A | 2/1994 | Hsia |
| 5,293,880 A | 3/1994 | Levitt |
| 5,300,097 A | 4/1994 | Lerner et al. |
| 5,303,585 A | 4/1994 | Lichte |
| 5,304,170 A | 4/1994 | Green |
| 5,304,173 A | 4/1994 | Kittrell et al. |
| 5,306,143 A | 4/1994 | Levy |
| 5,306,274 A | 4/1994 | Long |
| 5,316,075 A | 5/1994 | Quon et al. |
| 5,320,618 A | 6/1994 | Gustafsson et al. |
| 5,334,191 A | 8/1994 | Poppas et al. |
| 5,334,193 A | 8/1994 | Nardella |
| 5,336,217 A | 8/1994 | Buys et al. |
| 5,342,358 A | 8/1994 | Daikuzono et al. |
| 5,344,418 A | 9/1994 | Ghaffari |
| 5,344,434 A | 9/1994 | Talmore et al. |
| 5,348,551 A | 9/1994 | Spears et al. |
| 5,350,376 A | 9/1994 | Brown |
| 5,353,020 A | 10/1994 | Schurmann |
| 5,353,790 A | 10/1994 | Jacques et al. |
| 5,356,081 A | 10/1994 | Sellar |
| 5,358,503 A | 10/1994 | Bertwell et al. |
| 5,360,426 A | 11/1994 | Muller et al. |
| 5,369,831 A | 12/1994 | Bock |
| 5,380,317 A | 1/1995 | Everett et al. |
| 5,386,427 A | 1/1995 | Zayhowski |
| 5,403,306 A | 4/1995 | Edwards et al. |
| 5,405,368 A | 4/1995 | Eckhouse et al. |
| 5,409,446 A | 4/1995 | Rattner |
| 5,415,654 A | 5/1995 | Daikuzono et al. |
| 5,425,728 A | 6/1995 | Tankovich |
| 5,425,735 A | 6/1995 | Rosen et al. |
| 5,425,754 A | 6/1995 | Braun et al. |
| 5,445,608 A | 8/1995 | Chen et al. |
| 5,445,611 A | 8/1995 | Eppstein et al. |
| 5,454,807 A | 10/1995 | Lennox et al. |
| 5,458,140 A | 10/1995 | Eppstein et al. |
| 5,464,436 A * | 11/1995 | Smith .............................. 607/89 |
| 5,474,549 A | 12/1995 | Ortiz et al. |
| 5,486,170 A | 1/1996 | Winston et al. |
| 5,486,172 A | 1/1996 | Chess |
| 5,491,363 A | 2/1996 | Yoshikawa et al. |
| 5,501,680 A | 3/1996 | Kurtz et al. |
| 5,502,582 A | 3/1996 | Larson et al. |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles et al. |
| 5,527,368 A | 6/1996 | Supkis et al. |
| 5,531,739 A | 7/1996 | Trelles et al. |
| 5,531,740 A | 7/1996 | Black |
| 5,536,168 A | 7/1996 | Bourke |
| 5,549,660 A | 8/1996 | Mendes et al. |
| 5,558,667 A | 9/1996 | Yarborough et al. |
| 5,561,881 A | 10/1996 | Klinger et al. |
| 5,571,098 A | 11/1996 | Domankevitz et al. |
| 5,578,866 A | 11/1996 | DePoorter et al. |
| 5,595,568 A | 1/1997 | Anderson et al. |
| 5,611,475 A | 3/1997 | Sim et al. |
| 5,611,793 A | 3/1997 | Wilson et al. |
| 5,616,140 A | 4/1997 | Prescott |
| 5,618,284 A | 4/1997 | Sand |
| 5,620,478 A | 4/1997 | Eckhouse et al. |
| 5,626,631 A | 5/1997 | Eckhouse et al. |
| 5,628,744 A | 5/1997 | Coleman et al. |
| 5,630,811 A | 5/1997 | Miller |
| 5,634,711 A | 6/1997 | Kennedy et al. |
| 5,649,972 A | 7/1997 | Hochstein |
| 5,652,481 A | 7/1997 | Johnson et al. |
| 5,653,706 A | 8/1997 | Zavislan et al. |
| 5,655,547 A | 8/1997 | Karni et al. |
| 5,657,760 A | 8/1997 | Ying et al. |
| 5,658,148 A | 8/1997 | Neuberger et al. |
| 5,658,323 A | 8/1997 | Miller |
| 5,660,836 A | 8/1997 | Knowlton |
| 5,661,744 A | 8/1997 | Murakami et al. |
| 5,662,643 A | 9/1997 | Kung et al. |
| 5,662,644 A | 9/1997 | Swor |
| 5,673,451 A | 10/1997 | Moore et al. |
| 5,679,113 A | 10/1997 | Caisey et al. |
| 5,683,380 A | 11/1997 | Eckhouse et al. |
| 5,692,509 A | 12/1997 | Voss et al. |
| 5,698,866 A | 12/1997 | Doiron et al. |
| 5,707,401 A | 1/1998 | Talmore |
| 5,707,403 A | 1/1998 | Grove et al. |
| 5,713,738 A | 2/1998 | Yarborough |
| 5,714,119 A | 2/1998 | Kawagoe et al. |
| 5,718,117 A | 2/1998 | McDunn et al. |
| 5,720,772 A | 2/1998 | Eckhouse et al. |
| 5,722,397 A | 3/1998 | Eppstein |
| 5,725,522 A | 3/1998 | Sinofsky |
| 5,728,090 A | 3/1998 | Martin et al. |
| 5,735,844 A | 4/1998 | Anderson et al. |
| 5,735,884 A | 4/1998 | Thompson et al. |
| 5,738,678 A | 4/1998 | Patel et al. |
| 5,742,392 A | 4/1998 | Anderson et al. |
| 5,743,901 A | 4/1998 | Grove et al. |
| 5,743,902 A | 4/1998 | Trost |
| 5,746,735 A | 5/1998 | Furumoto et al. |
| 5,748,822 A | 5/1998 | Miura et al. |
| 5,755,751 A | 5/1998 | Eckhouse et al. |
| 5,759,200 A | 6/1998 | Azar et al. |
| 5,760,362 A | 6/1998 | Eloy |
| 5,768,103 A | 6/1998 | Kobrinetz et al. |
| 5,769,076 A | 6/1998 | Maekawa et al. |
| 5,782,249 A | 7/1998 | Weber et al. |
| 5,802,136 A | 9/1998 | Carol |
| 5,810,801 A | 9/1998 | Anderson et al. |
| 5,812,567 A | 9/1998 | Jeon et al. |
| 5,813,855 A | 9/1998 | Crisio, Jr. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,827,264 A | 10/1998 | Hohla et al. |
| 5,828,803 A | 10/1998 | Eckhouse et al. |
| 5,830,208 A | 11/1998 | Muller |
| 5,835,648 A | 11/1998 | Narciso, Jr. et al. |
| 5,836,877 A | 11/1998 | Zavislan |
| 5,836,999 A | 11/1998 | Eckhouse et al. |
| 5,840,048 A | 11/1998 | Cheng et al. |
| 5,849,029 A | 12/1998 | Eckhouse et al. |
| 5,851,181 A | 12/1998 | Talmor et al. |
| 5,853,407 A | 12/1998 | Miller |
| 5,860,967 A | 1/1999 | Zavislan et al. |
| 5,868,731 A | 2/1999 | Budnik et al. |
| 5,871,480 A | 2/1999 | Tankovich |
| 5,879,159 A | 3/1999 | Cipolla |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A | 4/1999 | Uram |
| 5,895,350 A | 4/1999 | Hori |
| 5,897,549 A | 4/1999 | Tankovich |
| 5,906,609 A | 5/1999 | Assa et al. |
| 5,908,418 A | 6/1999 | Dority et al. |
| 5,913,883 A | 6/1999 | Alexander et al. |
| 5,916,211 A | 6/1999 | Quon et al. |
| 5,920,374 A | 7/1999 | Vaphiades et al. |
| 5,921,926 A | 7/1999 | Rolland et al. |
| 5,928,222 A | 7/1999 | Kleinerman |
| 5,944,687 A | 8/1999 | Benett et al. |
| 5,944,748 A | 8/1999 | Mager et al. |
| 5,947,957 A | 9/1999 | Morris |
| 5,948,011 A | 9/1999 | Knowlton |
| 5,949,222 A | 9/1999 | Buono |
| 5,954,710 A | 9/1999 | Paolini et al. |
| 5,955,490 A | 9/1999 | Kennedy et al. |
| 5,957,915 A | 9/1999 | Trost |
| 5,964,749 A | 10/1999 | Eckhouse et al. |
| 5,968,033 A | 10/1999 | Fuller et al. |
| 5,968,034 A * | 10/1999 | Fullmer et al. .................... 606/9 |
| 5,974,059 A | 10/1999 | Dawson |

| | | | | | |
|---|---|---|---|---|---|
| 5,974,616 A | 11/1999 | Dreyfus | 6,235,016 B1 | 5/2001 | Stewart |
| 5,977,723 A | 11/1999 | Yoon et al. | 6,236,891 B1 | 5/2001 | Ingle et al. |
| 5,979,454 A | 11/1999 | Anvari et al. | 6,239,442 B1 | 5/2001 | Iimura |
| 5,984,915 A | 11/1999 | Loeb et al. | 6,240,306 B1 | 5/2001 | Rohrscheib et al. |
| 5,993,440 A * | 11/1999 | Ghassemi .................. 606/9 | 6,245,093 B1 | 6/2001 | Li et al. |
| 6,007,219 A | 12/1999 | O'Meara | 6,251,100 B1 | 6/2001 | Flock et al. |
| 6,015,404 A | 1/2000 | Altshuler et al. | 6,251,127 B1 | 6/2001 | Biel |
| 6,022,316 A | 2/2000 | Eppstein et al. | 6,254,388 B1 | 7/2001 | Yarborough |
| 6,026,828 A | 2/2000 | Altshuler | 6,263,233 B1 | 7/2001 | Zavislan et al. |
| 6,027,495 A | 2/2000 | Miller | 6,264,649 B1 | 7/2001 | Whitcroft et al. |
| 6,029,303 A | 2/2000 | Dewan | 6,267,779 B1 | 7/2001 | Gerdes |
| 6,029,304 A | 2/2000 | Hulke et al. | 6,267,780 B1 | 7/2001 | Streeter |
| 6,030,378 A | 2/2000 | Stewart | 6,273,884 B1 | 8/2001 | Altshuler et al. |
| 6,030,399 A | 2/2000 | Ignotz et al. | 6,273,885 B1 | 8/2001 | Koop et al. |
| 6,032,071 A | 2/2000 | Binder | 6,280,438 B1 | 8/2001 | Eckhouse et al. |
| RE36,634 E | 3/2000 | Ghaffari | 6,283,956 B1 | 9/2001 | McDaniel |
| 6,036,684 A | 3/2000 | Tankovich et al. | 6,287,549 B1 | 9/2001 | Sumian et al. |
| 6,044,514 A | 4/2000 | Kaneda et al. | 6,290,496 B1 | 9/2001 | Azar et al. |
| 6,050,990 A | 4/2000 | Tankovich et al. | 6,290,713 B1 | 9/2001 | Russell |
| 6,055,154 A | 4/2000 | Azar | 6,306,130 B1 * | 10/2001 | Anderson et al. ............. 606/27 |
| D424,197 S | 5/2000 | Sydlowski et al. | 6,306,160 B1 | 10/2001 | Nidetzky |
| 6,056,548 A | 5/2000 | Neuberger et al. | 6,315,772 B1 | 11/2001 | Marchitto et al. |
| 6,056,738 A | 5/2000 | Marchitto et al. | 6,317,624 B1 | 11/2001 | Kollias et al. |
| 6,058,937 A | 5/2000 | Doiron et al. | 6,319,274 B1 | 11/2001 | Shadduck |
| 6,059,820 A | 5/2000 | Baronov | 6,325,769 B1 | 12/2001 | Klopotek |
| 6,063,108 A | 5/2000 | Salansky et al. | 6,328,733 B1 | 12/2001 | Trost |
| 6,070,092 A | 5/2000 | Kazama et al. | 6,331,111 B1 | 12/2001 | Cao |
| 6,071,239 A | 6/2000 | Cribbs et al. | 6,340,495 B1 | 1/2002 | Sumian et al. |
| 6,074,382 A | 6/2000 | Asah et al. | 6,343,400 B1 | 2/2002 | Massholder et al. |
| 6,080,146 A | 6/2000 | Altshuler et al. | 6,343,933 B1 | 2/2002 | Montgomery et al. |
| 6,080,147 A | 6/2000 | Tobinick | 6,350,261 B1 | 2/2002 | Domankevitz et al. |
| 6,083,217 A | 7/2000 | Tankovich | 6,350,276 B1 | 2/2002 | Knowlton |
| 6,086,363 A | 7/2000 | Moran et al. | 6,354,370 B1 | 3/2002 | Miller et al. |
| 6,086,580 A | 7/2000 | Mordon et al. | 6,355,054 B1 | 3/2002 | Neuberger |
| 6,094,767 A | 8/2000 | Iimura | 6,358,242 B1 | 3/2002 | Cecchetti |
| 6,096,029 A | 8/2000 | O'Donnell, Jr. | 6,358,272 B1 | 3/2002 | Wilden et al. |
| 6,096,209 A | 8/2000 | O'Brien et al. | 6,383,176 B1 | 5/2002 | Connors et al. |
| 6,099,521 A | 8/2000 | Shadduck | 6,383,177 B1 | 5/2002 | Balle-Petersen et al. |
| 6,104,959 A | 8/2000 | Spertell | 6,387,089 B1 | 5/2002 | Kreindel et al. |
| 6,106,293 A | 8/2000 | Wiesel | 6,387,353 B1 | 5/2002 | Jensen et al. |
| 6,106,294 A | 8/2000 | Daniel | 6,395,016 B1 | 5/2002 | Oron et al. |
| 6,110,195 A | 8/2000 | Xie et al. | 6,400,011 B1 | 6/2002 | Miki |
| 6,113,559 A | 9/2000 | Klopotek | 6,402,739 B1 | 6/2002 | Neev |
| 6,117,129 A | 9/2000 | Mukai et al. | 6,406,474 B1 | 6/2002 | Neuberger et al. |
| 6,120,497 A | 9/2000 | Anderson et al. | 6,409,665 B1 | 6/2002 | Scott et al. |
| 6,126,655 A | 10/2000 | Domankevitz et al. | 6,413,267 B1 | 7/2002 | Dumoulin-White et al. |
| 6,129,723 A | 10/2000 | Anderson et al. | 6,416,319 B1 | 7/2002 | Cipolla |
| 6,135,774 A | 10/2000 | Hack et al. | 6,419,389 B1 | 7/2002 | Fuchs et al. |
| 6,142,650 A | 11/2000 | Brown et al. | 6,424,852 B1 | 7/2002 | Zavislan |
| 6,142,939 A | 11/2000 | Eppstein et al. | 6,425,912 B1 | 7/2002 | Knowlton |
| 6,149,644 A | 11/2000 | Xie | 6,435,873 B1 | 8/2002 | Burgio |
| 6,149,895 A | 11/2000 | Kutsch | 6,436,094 B1 | 8/2002 | Reuter |
| 6,159,236 A | 12/2000 | Biel | 6,439,888 B1 | 8/2002 | Boutoussov et al. |
| 6,162,055 A | 12/2000 | Montgomery et al. | 6,440,155 B1 | 8/2002 | Matsumae et al. |
| 6,162,211 A | 12/2000 | Tankovich et al. | 6,443,978 B1 | 9/2002 | Zharov |
| 6,162,212 A | 12/2000 | Kreindel et al. | 6,451,007 B1 | 9/2002 | Koop et al. |
| 6,171,300 B1 | 1/2001 | Adams | 6,461,296 B1 | 10/2002 | Desai |
| 6,171,301 B1 | 1/2001 | Nelson et al. | 6,464,694 B1 | 10/2002 | Massengill |
| 6,171,302 B1 | 1/2001 | Talpalriu et al. | 6,471,712 B2 | 10/2002 | Burres |
| 6,171,332 B1 | 1/2001 | Whitehurst | 6,471,716 B1 | 10/2002 | Pecukonis |
| 6,173,202 B1 | 1/2001 | Eppstein | 6,475,211 B2 | 11/2002 | Chess et al. |
| 6,174,325 B1 | 1/2001 | Eckhouse et al. | 6,484,052 B1 | 11/2002 | Visuri et al. |
| 6,176,854 B1 | 1/2001 | Cone | 6,485,413 B1 | 11/2002 | Boppart et al. |
| 6,183,434 B1 | 2/2001 | Eppstein | 6,491,685 B2 | 12/2002 | Visuri et al. |
| 6,183,500 B1 | 2/2001 | Kohler et al. | 6,494,900 B1 | 12/2002 | Salansky et al. |
| 6,183,773 B1 | 2/2001 | Anderson | 6,497,702 B1 | 12/2002 | Bernaz |
| 6,187,001 B1 | 2/2001 | Azar et al. | 6,503,486 B2 | 1/2003 | Xu et al. |
| 6,187,029 B1 | 2/2001 | Shapiro et al. | 6,508,785 B1 | 1/2003 | Eppstein |
| 6,197,020 B1 | 3/2001 | O'Donnell, Jr. | 6,508,813 B1 | 1/2003 | Altshuler |
| 6,200,134 B1 | 3/2001 | Kovac et al. | 6,511,475 B1 | 1/2003 | Altshuler et al. |
| 6,200,309 B1 | 3/2001 | Rice et al. | 6,514,243 B1 | 2/2003 | Eckhouse et al. |
| 6,202,242 B1 | 3/2001 | Salmon et al. | 6,517,532 B1 | 2/2003 | Altshuler et al. |
| 6,203,540 B1 | 3/2001 | Weber | 6,519,376 B2 | 2/2003 | Biagi et al. |
| 6,210,425 B1 | 4/2001 | Chen | 6,525,819 B1 | 2/2003 | Delawter et al. |
| 6,214,034 B1 | 4/2001 | Azar | 6,527,764 B1 | 3/2003 | Neuberger et al. |
| 6,221,095 B1 | 4/2001 | Van Zuylen et al. | 6,530,915 B1 | 3/2003 | Eppstein et al. |
| 6,228,075 B1 | 5/2001 | Furumoto | 6,537,270 B1 | 3/2003 | Elbrecht et al. |
| 6,229,831 B1 | 5/2001 | Nightingale et al. | 6,547,780 B1 | 4/2003 | Sinofsky |
| 6,235,015 B1 * | 5/2001 | Mead et al. .................. 606/9 | 6,551,346 B2 | 4/2003 | Crossley |

| | | | | | |
|---|---|---|---|---|---|
| 6,554,439 B1 | 4/2003 | Teicher et al. | 7,041,100 B2 | 5/2006 | Kreindel |
| 6,556,596 B1 | 4/2003 | Kim et al. | 7,044,959 B2 | 5/2006 | Anderson et al. |
| 6,558,372 B1 | 5/2003 | Altshuler | 7,060,061 B2 | 6/2006 | Altshuler et al. |
| 6,561,808 B2 | 5/2003 | Neuberger | 7,066,733 B2 | 6/2006 | Logan et al. |
| 6,569,155 B1 | 5/2003 | Connors et al. | 7,070,611 B2 | 7/2006 | Biel |
| 6,570,892 B1 | 5/2003 | Lin et al. | 7,077,840 B2 | 7/2006 | Altshuler et al. |
| 6,570,893 B1 | 5/2003 | Libatique et al. | 7,081,128 B2 | 7/2006 | Hart et al. |
| 6,572,634 B2 | 6/2003 | Koo | 7,097,639 B1 | 8/2006 | Almeida |
| 6,572,637 B1 | 6/2003 | Yamazaki et al. | 7,097,656 B1 | 8/2006 | Akopov et al. |
| 6,595,934 B1 | 7/2003 | Hissong et al. | 7,144,247 B2 | 12/2006 | Black |
| 6,600,951 B1 | 7/2003 | Anderson | 7,144,248 B2 | 12/2006 | Irwin |
| 6,602,245 B1 | 8/2003 | Thiberg et al. | 7,145,105 B2 | 12/2006 | Gaulard |
| 6,605,080 B1 | 8/2003 | Altshuler et al. | 7,145,108 B2 | 12/2006 | Kanel et al. |
| 6,605,083 B2 | 8/2003 | Clement et al. | 7,160,289 B2 | 1/2007 | Cohen |
| 6,606,755 B1 | 8/2003 | Robinson et al. | 7,182,760 B2 | 2/2007 | Kubota |
| 6,616,447 B1 | 9/2003 | Rizoiu et al. | 7,198,634 B2 | 4/2007 | Harth et al. |
| 6,616,451 B1 | 9/2003 | Rizolu et al. | 7,204,832 B2 | 4/2007 | Altshuler et al. |
| 6,618,531 B1 | 9/2003 | Goto et al. | 7,220,254 B2 | 5/2007 | Altshuler et al. |
| 6,623,272 B2 | 9/2003 | Clemans | 7,223,270 B2 | 5/2007 | Altshuler et al. |
| 6,623,513 B2 | 9/2003 | Biel | 7,223,281 B2 | 5/2007 | Altshuler et al. |
| 6,629,971 B2 | 10/2003 | McDaniel | 7,255,691 B2 | 8/2007 | Tolkoff et al. |
| 6,629,989 B2 | 10/2003 | Akita et al. | 7,274,155 B2 | 9/2007 | Inochkin et al. |
| 6,632,219 B1 | 10/2003 | Baranov et al. | 7,291,140 B2 | 11/2007 | MacFarland et al. |
| 6,635,075 B2 | 10/2003 | Li et al. | 7,309,335 B2 | 12/2007 | Altshuler et al. |
| 6,641,578 B2 | 11/2003 | Mukai | 7,311,722 B2 | 12/2007 | Larsen |
| 6,641,600 B1 | 11/2003 | Kohler et al. | 7,320,593 B2 | 1/2008 | Ostler et al. |
| 6,648,904 B2 | 11/2003 | Altshuler et al. | 7,322,972 B2 | 1/2008 | Viator et al. |
| 6,652,459 B2 | 11/2003 | Payne et al. | 7,329,273 B2 | 2/2008 | Altshuler et al. |
| 6,653,618 B2 | 11/2003 | Zenzie | 7,329,274 B2 | 2/2008 | Altshuler et al. |
| 6,659,999 B1 | 12/2003 | Anderson et al. | 7,331,964 B2 | 2/2008 | Maricle et al. |
| 6,660,000 B2 | 12/2003 | Neuberger et al. | 7,333,698 B2 | 2/2008 | Israel |
| 6,663,620 B2 | 12/2003 | Altshuler et al. | 7,351,252 B2 | 4/2008 | Altshuler et al. |
| 6,663,658 B1 | 12/2003 | Kollias et al. | 7,422,598 B2 | 9/2008 | Altshuler et al. |
| 6,663,659 B2 | 12/2003 | McDaniel | 7,423,767 B2 | 9/2008 | Steinsiek et al. |
| 6,666,856 B2 | 12/2003 | Connors et al. | 7,431,419 B2 | 10/2008 | Turner et al. |
| 6,675,425 B1 | 1/2004 | Iimura | 7,431,719 B2 | 10/2008 | Altshuler et al. |
| 6,676,654 B1 | 1/2004 | Balle-Petersen et al. | 7,540,869 B2 | 6/2009 | Altshuler et al. |
| 6,679,837 B2 | 1/2004 | Daikuzono | 7,624,640 B2 | 12/2009 | Maris et al. |
| 6,685,639 B1 | 2/2004 | Wang et al. | 7,647,092 B2 | 1/2010 | Motz et al. |
| 6,685,699 B1 | 2/2004 | Eppstein et al. | 2001/0007068 A1 | 7/2001 | Ota et al. |
| 6,689,124 B1 | 2/2004 | Thiberg et al. | 2001/0008973 A1 | 7/2001 | Van Zuylen et al. |
| 6,699,040 B1 | 3/2004 | Hahn et al. | 2001/0023363 A1 | 9/2001 | Harth et al. |
| 6,706,035 B2 | 3/2004 | Cense et al. | 2001/0024777 A1 | 9/2001 | Azar et al. |
| 6,709,269 B1 | 3/2004 | Altshuler | 2001/0041886 A1 | 11/2001 | Durkin et al. |
| 6,709,446 B2 | 3/2004 | Lundahl et al. | 2001/0046652 A1 | 11/2001 | Ostler et al. |
| 6,723,090 B2 | 4/2004 | Altshuler | 2001/0048077 A1 | 12/2001 | Afanassieva |
| 6,743,222 B2 | 6/2004 | Durkin et al. | 2002/0004066 A1 | 1/2002 | Stanley et al. |
| 6,746,444 B2 | 6/2004 | Key | 2002/0005475 A1 | 1/2002 | Zenzie |
| 6,749,623 B1 | 6/2004 | Hsi et al. | 2002/0013572 A1 | 1/2002 | Berlin |
| 6,770,069 B1 | 8/2004 | Hobart et al. | 2002/0016587 A1 | 2/2002 | Furumoto |
| 6,790,205 B1 | 9/2004 | Yamazaki et al. | 2002/0018754 A1 | 2/2002 | Sagel et al. |
| 6,801,595 B2 | 10/2004 | Grodzins et al. | 2002/0019624 A1 | 2/2002 | Clement et al. |
| 6,808,331 B2 | 10/2004 | Hall et al. | 2002/0026225 A1 | 2/2002 | Segal |
| 6,808,532 B2 | 10/2004 | Andersen et al. | 2002/0029071 A1 | 3/2002 | Whitehurst |
| RE38,670 E | 12/2004 | Asah et al. | 2002/0035360 A1* | 3/2002 | Connors et al. ............ 606/9 |
| 6,858,009 B2 | 2/2005 | Kawata et al. | 2002/0049483 A1 | 4/2002 | Knowlton |
| 6,860,879 B2 | 3/2005 | Irion et al. | 2002/0058890 A1 | 5/2002 | Visuri et al. |
| 6,862,771 B1 | 3/2005 | Muller | 2002/0071287 A1 | 6/2002 | Haase |
| 6,863,781 B2 | 3/2005 | Nocera et al. | 2002/0071827 A1 | 6/2002 | Petersen et al. |
| 6,868,436 B1 | 3/2005 | Fleming, III | 2002/0072676 A1 | 6/2002 | Afanassieva |
| 6,878,144 B2 | 4/2005 | Altshuler et al. | 2002/0081555 A1 | 6/2002 | Wiesel |
| 6,881,212 B1 | 4/2005 | Clement et al. | 2002/0091377 A1 | 7/2002 | Anderson et al. |
| 6,887,260 B1 | 5/2005 | McDaniel | 2002/0108193 A1 | 8/2002 | Gruber |
| 6,888,319 B2 | 5/2005 | Inochkin et al. | 2002/0111610 A1 | 8/2002 | Nordquist |
| 6,893,259 B1 | 5/2005 | Reizenson | 2002/0120256 A1 | 8/2002 | Furuno et al. |
| 6,902,397 B2 | 6/2005 | Farrell et al. | 2002/0123745 A1 | 9/2002 | Svaasand et al. |
| 6,902,563 B2 | 6/2005 | Wilkens et al. | 2002/0127224 A1 | 9/2002 | Chen |
| 6,936,046 B2 | 8/2005 | Hissong et al. | 2002/0128635 A1 | 9/2002 | Altshuler et al. |
| 6,942,658 B1 | 9/2005 | Rizoiu et al. | 2002/0128695 A1 | 9/2002 | Harth et al. |
| 6,953,341 B2 | 10/2005 | Black | 2002/0161357 A1 | 10/2002 | Anderson et al. |
| 6,974,451 B2 | 12/2005 | Altshuler et al. | 2002/0161418 A1 | 10/2002 | Wilkens et al. |
| 6,976,985 B2 | 12/2005 | Altshuler et al. | 2002/0173780 A1 | 11/2002 | Altshuler et al. |
| 6,989,023 B2 | 1/2006 | Black | 2002/0182563 A1 | 12/2002 | Boutoussov et al. |
| 6,991,644 B2 | 1/2006 | Spooner et al. | 2002/0183808 A1 | 12/2002 | Biel |
| 6,997,923 B2 | 2/2006 | Anderson | 2002/0198517 A1 | 12/2002 | Alfano et al. |
| 7,001,413 B2 | 2/2006 | Butler | 2003/0004499 A1 | 1/2003 | McDaniel |
| 7,006,223 B2 | 2/2006 | Mullani | 2003/0009158 A1 | 1/2003 | Perricone |
| 7,029,469 B2 | 4/2006 | Vasily | 2003/0009205 A1 | 1/2003 | Biel |
| 7,033,349 B2 | 4/2006 | Key | 2003/0018373 A1 | 1/2003 | Eckhardt et al. |

| | | |
|---|---|---|
| 2003/0023235 A1 | 1/2003 | Cense et al. |
| 2003/0023283 A1 | 1/2003 | McDaniel |
| 2003/0023284 A1 | 1/2003 | Gartstein et al. |
| 2003/0028227 A1 | 2/2003 | Neuberger et al. |
| 2003/0032900 A1 | 2/2003 | Ella |
| 2003/0032950 A1 | 2/2003 | Altshuler et al. |
| 2003/0036680 A1 | 2/2003 | Black |
| 2003/0040739 A1 | 2/2003 | Koop |
| 2003/0055414 A1 | 3/2003 | Altshuler et al. |
| 2003/0057875 A1 | 3/2003 | Inochkin et al. |
| 2003/0059738 A1 | 3/2003 | Neuberger |
| 2003/0065314 A1 | 4/2003 | Altshuler et al. |
| 2003/0083649 A1 | 5/2003 | Margaron et al. |
| 2003/0084534 A1 | 5/2003 | Kaizuka |
| 2003/0097122 A1 | 5/2003 | Ganz et al. |
| 2003/0100936 A1 | 5/2003 | Altshuler et al. |
| 2003/0104340 A1 | 6/2003 | Clemans |
| 2003/0109787 A1 | 6/2003 | Black |
| 2003/0109860 A1 | 6/2003 | Black |
| 2003/0113684 A1 | 6/2003 | Scott |
| 2003/0129154 A1 | 7/2003 | McDaniel |
| 2003/0130709 A1 | 7/2003 | D.C. et al. |
| 2003/0152528 A1 | 8/2003 | Singh et al. |
| 2003/0163884 A1 | 9/2003 | Weihrauch |
| 2003/0167080 A1 | 9/2003 | Hart et al. |
| 2003/0169433 A1 | 9/2003 | Koele et al. |
| 2003/0181896 A1 | 9/2003 | Zvuloni et al. |
| 2003/0187486 A1 | 10/2003 | Savage et al. |
| 2003/0195494 A1 | 10/2003 | Altshuler et al. |
| 2003/0199859 A1 | 10/2003 | Altshuler et al. |
| 2003/0216795 A1 | 11/2003 | Harth et al. |
| 2003/0232303 A1 | 12/2003 | Black |
| 2004/0006332 A1 | 1/2004 | Black |
| 2004/0010298 A1 | 1/2004 | Altshuler et al. |
| 2004/0015156 A1 | 1/2004 | Vasily |
| 2004/0015158 A1 | 1/2004 | Chen et al. |
| 2004/0019990 A1 | 2/2004 | Farrell et al. |
| 2004/0024388 A1 | 2/2004 | Altshuler |
| 2004/0030326 A1 | 2/2004 | Altshuler et al. |
| 2004/0034319 A1 | 2/2004 | Anderson et al. |
| 2004/0034341 A1 | 2/2004 | Altshuler et al. |
| 2004/0073079 A1 | 4/2004 | Altshuler et al. |
| 2004/0082940 A1 | 4/2004 | Black et al. |
| 2004/0085026 A1 | 5/2004 | Inochkin et al. |
| 2004/0093042 A1 | 5/2004 | Altshuler et al. |
| 2004/0093043 A1 | 5/2004 | Edel et al. |
| 2004/0111132 A1 | 6/2004 | Shenderova et al. |
| 2004/0116984 A1 | 6/2004 | Spooner et al. |
| 2004/0133251 A1 | 7/2004 | Altshuler et al. |
| 2004/0143920 A1 | 7/2004 | Nanda |
| 2004/0147984 A1 | 7/2004 | Altshuler et al. |
| 2004/0156626 A1 | 8/2004 | Thoms |
| 2004/0161213 A1 | 8/2004 | Lee |
| 2004/0162549 A1 | 8/2004 | Altshuler |
| 2004/0162596 A1 | 8/2004 | Altshuler et al. |
| 2004/0167500 A1* | 8/2004 | Weckwerth et al. ............ 606/9 |
| 2004/0176764 A1 | 9/2004 | Dant |
| 2004/0191729 A1 | 9/2004 | Altshuler et al. |
| 2004/0193234 A1 | 9/2004 | Butler |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2004/0204745 A1 | 10/2004 | Altshuler et al. |
| 2004/0210276 A1 | 10/2004 | Altshuler et al. |
| 2004/0214132 A1 | 10/2004 | Altshuler |
| 2004/0225339 A1 | 11/2004 | Yaroslavsky et al. |
| 2004/0230258 A1 | 11/2004 | Altshuler et al. |
| 2004/0230260 A1 | 11/2004 | MacFarland et al. |
| 2004/0234460 A1 | 11/2004 | Tarver et al. |
| 2005/0038418 A1 | 2/2005 | Altshuler et al. |
| 2005/0049467 A1 | 3/2005 | Stamatas et al. |
| 2005/0049582 A1 | 3/2005 | DeBenedictis et al. |
| 2005/0049658 A1 | 3/2005 | Connors et al. |
| 2005/0063931 A1 | 3/2005 | Paus et al. |
| 2005/0065531 A1 | 3/2005 | Cohen |
| 2005/0085875 A1 | 4/2005 | Van Zuylen |
| 2005/0107849 A1 | 5/2005 | Altshuler et al. |
| 2005/0168158 A1 | 8/2005 | Inochkin et al. |
| 2005/0171517 A1 | 8/2005 | Altshuler et al. |
| 2005/0171581 A1 | 8/2005 | Connors et al. |
| 2005/0177026 A1 | 8/2005 | Hoeg et al. |
| 2005/0182389 A1 | 8/2005 | LaPorte et al. |
| 2005/0197681 A1 | 9/2005 | Barolet et al. |
| 2005/0215988 A1 | 9/2005 | Altshuler et al. |
| 2005/0220726 A1 | 10/2005 | Pauly et al. |
| 2005/0251118 A1 | 11/2005 | Anderson et al. |
| 2006/0004306 A1 | 1/2006 | Altshuler et al. |
| 2006/0004347 A1 | 1/2006 | Altshuler et al. |
| 2006/0009750 A1 | 1/2006 | Altshuler et al. |
| 2006/0020309 A1 | 1/2006 | Altshuler et al. |
| 2006/0047281 A1 | 3/2006 | Kreindel |
| 2006/0058712 A1 | 3/2006 | Altshuler et al. |
| 2006/0079947 A1 | 4/2006 | Tankovich et al. |
| 2006/0089687 A1 | 4/2006 | Spooner et al. |
| 2006/0094988 A1 | 5/2006 | Tosaya et al. |
| 2006/0122668 A1 | 6/2006 | Anderson et al. |
| 2006/0149343 A1 | 7/2006 | Altshuler et al. |
| 2006/0161143 A1 | 7/2006 | Altshuler et al. |
| 2006/0194164 A1 | 8/2006 | Altshuler et al. |
| 2006/0206103 A1 | 9/2006 | Altshuler et al. |
| 2006/0253176 A1 | 11/2006 | Caruso et al. |
| 2006/0271028 A1 | 11/2006 | Altshuler et al. |
| 2006/0287646 A1 | 12/2006 | Altshuler et al. |
| 2007/0027440 A1 | 2/2007 | Altshuler et al. |
| 2007/0038206 A1 | 2/2007 | Altshuler et al. |
| 2007/0049910 A1 | 3/2007 | Altshuler et al. |
| 2007/0060819 A1 | 3/2007 | Altshuler et al. |
| 2007/0067006 A1 | 3/2007 | Altshuler et al. |
| 2007/0073308 A1 | 3/2007 | Anderson et al. |
| 2007/0078501 A1 | 4/2007 | Altshuler et al. |
| 2007/0159592 A1 | 7/2007 | Rylander et al. |
| 2007/0185552 A1 | 8/2007 | Masotti et al. |
| 2007/0194717 A1 | 8/2007 | Belikov |
| 2007/0198004 A1 | 8/2007 | Altshuler et al. |
| 2007/0213696 A1 | 9/2007 | Altshuler et al. |
| 2007/0213698 A1 | 9/2007 | Altshuler et al. |
| 2007/0213792 A1 | 9/2007 | Yaroslavsky et al. |
| 2007/0219604 A1 | 9/2007 | Yaroslavsky et al. |
| 2007/0219605 A1 | 9/2007 | Yaroslavsky et al. |
| 2007/0239142 A1 | 10/2007 | Altshuler et al. |
| 2007/0239143 A1 | 10/2007 | Altshuler et al. |
| 2007/0255355 A1 | 11/2007 | Altshuler et al. |
| 2007/0288071 A1 | 12/2007 | Rogers |
| 2008/0009842 A1 | 1/2008 | Manstein et al. |
| 2008/0058783 A1 | 3/2008 | Altshuler et al. |
| 2008/0132886 A1 | 6/2008 | Cohen et al. |
| 2008/0139901 A1 | 6/2008 | Altshuler et al. |
| 2008/0140164 A1 | 6/2008 | Oberreiter et al. |
| 2008/0172047 A1 | 7/2008 | Altshuler et al. |
| 2008/0183162 A1 | 7/2008 | Altshuler et al. |
| 2008/0183250 A1 | 7/2008 | Tanojo et al. |
| 2008/0195183 A1 | 8/2008 | Botchkareva et al. |
| 2008/0214988 A1 | 9/2008 | Altshuler et al. |
| 2008/0294150 A1 | 11/2008 | Altshuler et al. |
| 2008/0306471 A1 | 12/2008 | Altshuler et al. |
| 2009/0048557 A1 | 2/2009 | Yeshurun et al. |
| 2009/0069741 A1 | 3/2009 | Altshuler et al. |

FOREIGN PATENT DOCUMENTS

| | | |
|---|---|---|
| AU | 1851583 | 3/1984 |
| AU | 2002303863 | 12/2002 |
| CN | 2053926 U | 3/1990 |
| CN | 1073607 A | 6/1993 |
| CN | 1182572 A | 5/1998 |
| CN | 1351483 A | 5/2002 |
| CN | 1535126 A | 10/2004 |
| CN | 1262249 C | 7/2006 |
| DE | 3304230 A1 | 8/1984 |
| DE | 3719561 | 1/1988 |
| DE | 3837248 | 5/1990 |
| DE | 9102407 | 8/1991 |
| DE | 19803460 C1 | 8/1999 |
| DE | 19944401 A1 | 3/2001 |
| DE | 10140715 A1 | 3/2002 |
| DE | 10112289 | 9/2002 |
| DE | 10120787 A1 | 1/2003 |
| EP | 0142671 | 5/1985 |
| EP | 0 172 490 | 2/1986 |

| | | | | | |
|---|---|---|---|---|---|
| EP | 0565331 | 10/1993 | WO | WO-9623447 | 8/1996 |
| EP | 0598984 | 6/1994 | WO | WO-9625979 | 8/1996 |
| EP | 0724894 | 8/1996 | WO | WO-96/28212 | 9/1996 |
| EP | 0726083 | 8/1996 | WO | WO-9636396 | 11/1996 |
| EP | 0736308 | 10/1996 | WO | WO-9641579 | 12/1996 |
| EP | 0743029 | 11/1996 | WO | WO-9713458 | 4/1997 |
| EP | 0755698 | 1/1997 | WO | WO-9713552 | 4/1997 |
| EP | 0763371 | 3/1997 | WO | WO-97/22384 A1 | 6/1997 |
| EP | 0765673 | 4/1997 | WO | WO-97/28752 A1 | 8/1997 |
| EP | 0765674 | 4/1997 | WO | WO-98/05286 A1 | 2/1998 |
| EP | 0783904 | 7/1997 | WO | WO-98/05380 A1 | 2/1998 |
| EP | 0 885 629 | 12/1998 | WO | WO-98/06456 A1 | 2/1998 |
| EP | 0884066 | 12/1998 | WO | WO-98/07379 A1 | 2/1998 |
| EP | 0885629 | 12/1998 | WO | WO-9804317 | 2/1998 |
| EP | 1038505 | 9/2000 | WO | WO-98/20937 A2 | 5/1998 |
| EP | 1057454 | 12/2000 | WO | WO-9824507 | 6/1998 |
| EP | 1075854 | 2/2001 | WO | WO-98/41158 A1 | 9/1998 |
| EP | 1138349 | 10/2001 | WO | WO-9851235 | 11/1998 |
| EP | 1147785 | 10/2001 | WO | WO-9852481 | 11/1998 |
| EP | 1219258 | 7/2002 | WO | WO-9858595 | 12/1998 |
| EP | 1226787 | 7/2002 | WO | WO-99/10046 A1 | 3/1999 |
| EP | 1238683 A1 | 9/2002 | WO | WO-99/17668 A1 | 4/1999 |
| EP | 1250893 | 10/2002 | WO | WO-9917666 | 4/1999 |
| EP | 1457234 | 9/2004 | WO | WO-9917667 | 4/1999 |
| EP | 1495735 A1 | 1/2005 | WO | WO-9927997 | 6/1999 |
| EP | 1512373 | 3/2005 | WO | WO-9929243 | 6/1999 |
| EP | 1627662 | 2/2006 | WO | WO-99/34867 A1 | 7/1999 |
| EP | 1839705 A1 | 10/2007 | WO | WO-9938569 A2 | 8/1999 |
| EP | 1854505 A2 | 11/2007 | WO | WO-9938569 A3 | 8/1999 |
| EP | 1535582 | 3/2009 | WO | WO-99/43387 A1 | 9/1999 |
| FR | 2199453 | 4/1974 | WO | WO-99/44638 A1 | 9/1999 |
| FR | 2591902 | 6/1987 | WO | WO-9946005 | 9/1999 |
| GB | 1546625 | 5/1979 | WO | WO-9949937 | 10/1999 |
| GB | 2044908 | 10/1980 | WO | WO-99/62472 A1 | 12/1999 |
| GB | 2059053 | 4/1981 | WO | WO-99/66988 A1 | 12/1999 |
| GB | 2059054 | 4/1981 | WO | WO-0002491 | 1/2000 |
| GB | 2123287 | 2/1984 | WO | WO-0003257 | 1/2000 |
| GB | 2239675 A | 7/1991 | WO | WO-00/07514 A1 | 2/2000 |
| GB | 2270159 A | 3/1994 | WO | WO-00/30714 A1 | 6/2000 |
| GB | 2356570 | 5/2001 | WO | WO-0032272 | 6/2000 |
| GB | 2360461 A | 9/2001 | WO | WO-00/41278 A1 | 7/2000 |
| GB | 2360946 | 10/2001 | WO | WO-0040266 | 7/2000 |
| GB | 2364376 | 1/2002 | WO | WO-0043070 | 7/2000 |
| GB | 2368020 | 4/2002 | WO | WO-0044294 | 8/2000 |
| GB | 2390021 | 12/2003 | WO | WO-00/54649 A2 | 9/2000 |
| GB | 2397528 | 7/2004 | WO | WO-00/54685 | 9/2000 |
| JP | 54129791 A | 10/1979 | WO | WO-0054685 | 9/2000 |
| JP | 03-066387 | 3/1991 | WO | WO-0062700 | 10/2000 |
| JP | 10014661 A | 1/1998 | WO | WO-00/66226 A1 | 11/2000 |
| JP | 10165410 A | 6/1998 | WO | WO-0064537 | 11/2000 |
| JP | 11047146 A | 2/1999 | WO | WO-0071045 | 11/2000 |
| JP | 11081877 A | 3/1999 | WO | WO-0074583 | 12/2000 |
| JP | 2000037400 | 2/2000 | WO | WO-0074781 | 12/2000 |
| JP | 2000300684 A | 10/2000 | WO | WO-0078242 | 12/2000 |
| JP | 2001029124 A | 2/2001 | WO | WO-0103257 | 1/2001 |
| JP | 2001145520 | 5/2001 | WO | WO-01/14012 A1 | 3/2001 |
| JP | 2001343560 A | 12/2001 | WO | WO-0126573 | 4/2001 |
| JP | 2002506362 A | 2/2002 | WO | WO-01/34048 | 5/2001 |
| JP | 2002272861 A | 9/2002 | WO | WO-0134048 | 5/2001 |
| JP | 2003192809 | 7/2003 | WO | WO-01/41872 A1 | 6/2001 |
| JP | 2005017796 A | 1/2005 | WO | WO-01/42671 | 6/2001 |
| JP | 2005027702 A | 2/2005 | WO | WO-0154606 | 8/2001 |
| RU | 2082337 | 6/1997 | WO | WO-0154770 | 8/2001 |
| RU | 2089126 | 9/1997 | WO | WO-0178830 | 10/2001 |
| RU | 2089127 | 9/1997 | WO | WO-02/26147 A1 | 4/2002 |
| RU | 2096051 | 11/1997 | WO | WO-02053050 | 7/2002 |
| RU | 2122848 | 12/1998 | WO | WO-02069825 | 9/2002 |
| WO | WO-8602783 | 5/1986 | WO | WO-02/078559 | 10/2002 |
| WO | WO-8804592 | 6/1988 | WO | WO-02/094116 | 11/2002 |
| WO | WO-9000420 | 1/1990 | WO | WO-02094116 | 11/2002 |
| WO | WO-9102562 | 3/1991 | WO | WO-03/005883 A2 | 1/2003 |
| WO | WO-9113652 | 9/1991 | WO | WO-03/049633 A1 | 6/2003 |
| WO | WO-9216338 | 10/1992 | WO | WO-2004/000150 A1 | 12/2003 |
| WO | WO-9219165 | 11/1992 | WO | WO-2004/011848 A2 | 2/2004 |
| WO | WO-9305920 | 4/1993 | WO | WO-2004033040 | 4/2004 |
| WO | WO-95/10243 A1 | 4/1995 | WO | WO-2004/037068 A2 | 5/2004 |
| WO | WO-9515725 | 6/1995 | WO | WO-2004/037287 A2 | 5/2004 |
| WO | WO-9532441 | 11/1995 | WO | WO-2004/080279 A2 | 9/2004 |
| WO | WO-96/22741 A1 | 8/1996 | WO | WO-2004073537 | 9/2004 |

| | | |
|---|---|---|
| WO | WO-2004084752 | 10/2004 |
| WO | WO-2004086947 | 10/2004 |
| WO | WO-2005007003 | 1/2005 |
| WO | WO-2005009266 | 2/2005 |
| WO | WO-2005030317 | 4/2005 |
| WO | WO-2005/046793 A2 | 5/2005 |
| WO | WO-2005/065288 A2 | 7/2005 |
| WO | WO-2005/092438 A1 | 10/2005 |
| WO | WO-2005/096981 A2 | 10/2005 |
| WO | WO-2005/099369 A2 | 10/2005 |
| WO | WO-2005112815 | 12/2005 |
| WO | WO-2006/006123 A1 | 1/2006 |
| WO | WO-2006036968 | 4/2006 |
| WO | WO-2006/066226 A1 | 6/2006 |
| WO | WO-2006/089227 A2 | 8/2006 |
| WO | WO-2006/101735 A1 | 9/2006 |
| WO | WO-2006/116141 A1 | 11/2006 |
| WO | WO-2007/035444 | 3/2007 |
| WO | WO-2007/122611 A2 | 11/2007 |
| WO | WO-2008/070747 A2 | 6/2008 |

OTHER PUBLICATIONS

A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.
Abstract Nos. 17-19, Lasers in Surgery and Medicine, ASLMS, Supplement 13, 2001.
Abstracts, Lasers in Surgery and Medicine, *ASLMS*, Twenty-First Annual Meeting, Sep. 13, 2001.
Abstracts, various.
Altshuler et al, "Acoustic Response of Hard Dental Tissues to Pulsed Laser Action", *SPIE* 2080:97-103 1993.
Altshuler et al., "Extended Theory of Selective Photothermolysis", *Lasers in Surgery and Medicine* 29:416-432 2001.
Anderson et al., "Selective Photothermolysis: Precise Microsurgery by Selective Absorption of Pulsed Radiation", *Science*, 220:524-527, 1983.
Anderson et al., "The Optics of Human Skin", *The Journal of Investigative Dermatology*, 77:13-19, 1981.
Bjerring et al., "Selective non-ablative wrinkle reduction by laser", *Journal of Cutaneous Laser Therapy* 2000; 2:9-15.
C.R. Taylor et al., "Treatment of tattoos by Q-switched ruby laser," Arch. Dermatol. vol. 126, pp. 893-899, Jul. 1990.
Doukas et al., "Transdermal Drug Delivery With a Pressure Wave", *Advanced Drug Delivery Reviews* 56, pp. 559-579, 2004.
Dover et al., "Pigmented Guinea Pig Skin Irradiated With Q-Switched Ruby Laser Pulses", *Arch Dermatol*, 125:43-49, 1989.
E. Klein et al., "Biological effects of laser radiation 1.,"Northeast Electronics Research and Engineering Meeting, NEREM Record, IEEE catalogue No. F-60, pp. 108-109, 1965.
E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.
Finkelstein et al., "Epilation of Hair-Bearing Urethral Grafts Using the Neodymium:Yag Surgical Laser", *The Journal of Urology*, 146:840-842, 1991.
Fiskerstrand, et al., "Hair Removal With Long Pulsed Diode Lasers: A Comparison Between Two Systems With Different Pulse Structures", *Lasers in Surgery and Medicine*, 32:399-404, 2003.
G.G. Riggle et al., "Laser effects on normal and tumor tissue," Laser Applications in Medicine and Biology, vol. I, M.L. Wolbarsht, editor, Plenum Press, publishers, Chapter 3, pp. 35-65, 1971.
Goldman et al., "Preliminary Investigation of Fat Embolization from Pulsed Ruby Laser Impacts of Bone", *Nature*, 221:361-363, 1969.
Goldman et al., "Effect of the Laser Beam on the Skin: III. Exposure of Cytological Preparations", *The Journal of Investigative Dermatology*, 42:247-251, 1964.
Goldman et al., "Impact of the Laser on Nevi and Melanomas", *Arch Dermatol*, 90:71-75, 1964.
Goldman et al.,"Laser Action at the Cellular Level", *JAMA*, 198:641-644, 1966.

Goldman et al., "Laser Treatment of Tattoos", *JAMA*, 201:841-844, 1967.
Goldman et al., "Long-Term Laser Exposure of a Senile Freckle", *Arch Environ Health*, 22:401-403, 1971.
Goldman et al., "Pathology of the Effect of the Laser Beam on the Skin", *Nature*, 197:912-914, 1963.
Goldman et al., "Replica Microscopy and Scanning Electron Microscopy of Lawer Impacts on the Skin", *The Journal of Investigative Dermatology*, 52:18-24, 1969.
Goldman et al., "The Effect of Repeated Exposures to Laser Beams", *Acta derm. venereol.* 44:264-268, 1964.
Goldman et al., "Treatment of Basal Cell Epithelioma by Laser Radiation", *JAMA*, 189:773-775, 1964.
Goldman, et al., "Effect of the Laser Beam on the Skin: Preliminary and Short Report", *The Journal of Investigative Dermatology*, 40:121-122, 1963.
Goldman, et al., "Radiation from a Q-Switched Ruby Laser. Effect of Repeated Impacts of Power Output of 10 Megawatts on a Tattoo of Men", *The Journal of Investigative Dermatology*, 44:69-71, 1965.
Goldman, et al., "The Biomedical Aspects of Lasers", *JAMA*, 188: 1967 (15 pgs).
Goldman, Leon, "Dermatologic Manifestations of Laser Radiation", *Federation of American Societies for Experimental Biology*, Suppl. 14:S-92-S-93, 1965.
Goldman, Leon, "Effects of New Laser Systems on the Skin", *Arch Dermatol*, 108:385-390, 1973.
Goldman, Leon, "Laser Surgery for Skin Cancer", *New York State Journal of Medicine*, 77:1897-1900, 1977.
Goldman, Leon, "Surgery by Laser for Malignant Melanoma", *J. Dermatol. Surg. Oncol.* 5:2:141-144, 1979.
Goldman, Leon, "The Skin", *Arch Environ Health*, 18:434-436, 1969.
Grossman et al., "Damage to Hair Follicles by Normal-Mode Ruby Laser Pulses", *Journal of the American Academy of Dermatology*, 35:889-894, 1996.
Grossman et al., "Laser Targeted at Hair Follicles", *American Society for Laser Medicine and Surgery*, Suppl. 7:221, 1995 (4 pgs).
J.A. Parrish, "Selective thermal effects with pulsed irradiation from lasers: From organ to organelle," Journal of Investigative Dermatology, vol. 80, No. 6 Supplement, pp. 75s-80s, 1983.
J.G. Kuhns et al., "Biological effects of laser radiation II Effects of laser irradiation on the skin," NEREM Record, pp. 152-153, 1965.
J.G. Kuhns et al., "Laser injury in skin," Laboratory Investigation, vol. 17, No. 1, pp. 1-13, Jul. 1967.
L. Goldman et al., "Effect of the laser beam on the skin, Preliminary report" Journal of Investigative Dermatology, vol. 40, pp. 121-122, 1963.
L. Goldman et al., "Laser treatment of tattoos, A preliminary survey of three year's clinical experience," JAMA, vol. 201, No. 11, pp. 841-844, Sep. 1967.
L. Goldman et al., The biomedical aspects of lasers, JAMA, vol. 188, No. 3, pp. 302-306, Apr. 1964.
L. Goldman, Biomedical Aspects of the Laser, Springer-Verlag New York Inc., publishers, Chapts. 1, 2, & 23, 1967.
L. Polla et al., "Melanosomes are a primary target of Q-switched ruby laser irradiation in guinea pig skin," Journal of Investigative Dermatology, vol. 89, No. 3, pp. 281-286, Sep. 1987.
Manstein et al., "Selective Photothermolysis of Lipio Rich Tissue", *American Society for Laser Medicine and Surgery Abstracts*, 2001 (2 pgs).
Margolis et al., "Visible Action Spectrum for Melanin-Specific Selective Photothermolysis", *Lasers in Surgery and Medicine* 9:389-397, 1989.
Ohshiro et al., "The Ruby and Argon Lasers in the Treatment of the Naevi," Annals Academy of Medicine, Apr. 1983, vol. 12, No. 2, pp. 388-395.
P. Bjerring et al., "Selective Non-Ablative Wrinkle Reduction by Laser," J Cutan Laser Ther, vol. 2, pp. 9-15, 2000.
S. Watanabe et al, "Comparative studies of femtosecondd to microsecond laser pulses on selective pigmented cell injury in skin," Photochemistry and Photobiology, vol. 53, No. 6, pp. 757-762, 1991.
Shimbashi, et al., "Ruby LaserTreatment of Pigmented Skin Lesions", *Aesthetic Plastic Surgery*, 19:225-229, 1995.

Storb et al., "Selective Mitochondrial Damage by a Ruby Laser Microbeam: An Electron Microscopic Study", *Science*, pp. 736-738, 1965.

Stratton, et al., "Biological Effects of Laser Radiation II: ESR Studies of Melanin Containing Tissues after Laser Irradiation", *NEREM Record*, IEEE Catalogue No. F-60, pp. 150-151, 1965.

Sumian et al., "Laser Skin Resurfacing Using a Frequency Doubled Nd:YAG Laser After Topical Application of an Exogenous Chromophore", *Lasers in Surgery and Medicine* 25:43-50, 1999.

Sumian, C.C. et al., "A Preliminary Clinical and Histopathological Study of Laser Skin Resurfacing Using a Frequency-Doubled Nd:YAG Laser After Application of Chromofilm.RTM.," Journal of Cutaneous Laser Therapy, vol. 1, pp. 159-166, 1999.

T. Shimbashi & T. Kojima, "Ruby laser treatment of pigmented skin lesions," Aesth. Plast. Surg., vol. 19, pp. 225-229, 1995.

Yules, et al., "The Effect of Q-Switched Ruby Laser Radiation on Dermal Tattoo Pigment in Man", *Arch Surg.*, 95:179-180, 1967.

International Preliminary Examination Report, International Patent Application No. PCT/US02/16435, completed Sep. 24, 2003 (5 pages).

International Search Report, International Patent Application No. PCT/US02/16435, mailed Sep. 26, 2002 (4 pages).

PCT International Preliminary Report on Patentability dated Oct. 8, 2007 for International Application No. PCT/US2006/035927 (7 pages).

Written Opinion from the International Preliminary Examining Authority, International Patent Application No. PCT/US02/16435, mailed May 22, 2003 (5 pages).

Examination Report, Canadian Patent Application No. 2,448,385, dated Jul. 9, 2007 (5 pgs).

Examination Report, Canadian Patent Application No. 2,448,385, dated Aug. 4, 2008 (4 pgs).

Supplemental Partial European Search Report, European Patent Application No. 02731925, dated Oct. 13, 2005 (5 pgs).

European Examination Report, European Patent Application No. 02731925, dated Apr. 5, 2007 (5 pgs).

European Examination Report, European Patent Application No. 02731925, dated Sep. 1, 2008 (3 pgs).

Examination Report, Australian Patent Application No. 2002303863, dated Apr. 27, 2005 (2 pgs).

Examination Report, Australian Patent Application No. 2006246485, dated Mar. 27, 2007 (2 pgs).

Japan Office Action, Japanese Patent Application No. 2002-590840, dated Jan. 24, 2008 (1 pg).

Japan Office Action, Japanese Patent Application No. 2002-590840, dated Sep. 2, 2008 (1 pg).

First Office Action, Chinese Patent Application No. 02814860.6, issued Apr. 22, 2005 (11 pgs).

First Office Action, Chinese Patent Application No. 200610079270.1, issued Dec. 7, 2007 (7 pgs).

Second Office Action, Chinese Patent Application No. 200610079270.1, issued Aug. 22, 2008 (17 pgs).

First Office Action, Chinese Patent Application No. 200610093460.9, issued Dec. 7, 2007 (7 pgs).

Second Office Action, Chinese Patent Application No. 200610093460.9, issued Aug. 22, 2008 (8 pgs).

Marinelli et al., "Diode Laser Illuminated Automotive Lamp Systems", *SPIE*, 3285:170-177, 1998.

Remillard, et al., "Diode Laser Illuminators for Night Vision Applications", Proc. SPIE 4285, 14-22, 2001.

Remillard, et al., "Diode Laser Illuminted Automotive Brake Lamp Using Linear Fanout Diffractive Optical Element in Diffractive Optics and Micro-Optics", OSA Technical Digest Series, vol. 10, 192-194, 1998.

Rhorer et al., Evaluating the Safety and Efficacy of a Novel Light Based Hair Removal System, ASLMS 2001 Convention, New Orleans, Apr. 2001 (2 pgs).

Watanabe, et al., "The Effect of Pulse Duration on Selective Pigmented Cell Injury by Dye Lasers," *The Journal of Investigative Dermatology*, 88:523, 1987 (2 pgs).

"Bioptron Light Therapy System," website print-out, accessed Jul. 13, 2006 (1 page).

Altshuler et al., "Human Tooth as an Optical Device," SPIE vol. 1429 Holography Interferometry and Optical Pattern Recognition in Biomedicine, pp. 95-104, 1991. 10 pages.

Altshuler et al., "Modern Optics and Dentistry," Lasers in Dentistry, pp. 283-297, 1995. 17 pages.

Altshuler et al., "New Optical Effects in the Human Hard Tooth Tissues," Lasers and Medicine, Proc. SPIE vol. 1353, pp. 97-102, 1989. 6 pages.

Amy, R.L. et al., "Selective mitochondrial damage by a ruby laser microbeam: An electron microscopic study," Science, vol. 150, pp. 756-758, Nov. 1965. 3 pages.

Anderson, R.R. et al., "Selective photothermolysis: Precise microsurgery by selective absorption of pulsed radiation," Science, vol. 220, pp. 524-527, Apr. 1983. www.sciencemag.org, accessed Oct. 13, 2011, 4 pages.

Apfelberg et al. "Analysis of Complications of Argon Laser Treatment for Port Wine Hemangiomas with Reference to Striped Technique," Lasers in Surgery and Medicine, 2:357-371 (1983). 16 pages.

Apfelberg et al. "Dot or Pointillistic Method for Improvement in Results of Hypertrophic Scarring in the Argon Laser Treatment of Portwine Hemangiomas," Lasers in Surgery and Medicine, 6:552-558 (1987). 8 pages.

Blankenau et al., "In Vivo Caries-Like Lesion Prevention with Argon Laser: Pilot Study," Journal of Clinical Laser Medicine and Surgery, vol. 17, No. 6, pp. 241-243, 1999.

Chan, E.K., "Effects of Compression on Soft Tissue Optical Properties," IEEE Journal of Selected Topics in Quantum Electronics, vol. 2, No. 4, pp. 943-950 (Dec. 1996). 8 pages.

Dabrowska, "Intravital Treatment of the Pulp with Stimulation Laser Biostimulation," Rocz-Akad-Med-Bialymst. 1997; 42(1): 168-76.—Abstract 10 pages.

Dixon et al. "Hypertrophic Scarring in Argon Laser Treatment of Port-Wine Stains," Plastic and Reconstructive Surgery, 73:771-777 (1984). 8 pages.

Forrest-Winchester et al., "The Effect of Infrared Laser Radiation on Dentinal Permeability in vitro," Department of Dentistry, University of Queensland Dental School, pp. 1-8, 1992. 8 pages.

Ginsbach et al. "New Aspects in the Management of Benign Cutaneous Tumors," Laser 79 Opto-Electronics, Munich Conference Proceedings, 344-347 (1979).

Gottlieb, I., "Power Supplies, Switching Regulators, Inverters & Converters," 1976. 6 pages.

Greenwald et al. "Comparative Histological Studies of the Tunable Dye (at 577 nm) Laser and Argon Laser: The Specific Vascular Effects of the Dye Laser," The Journal of Investigative Dermatology, 77:305-310 (1981). 7 pages.

Grossman, et al., "780 nm Low Power Diode Laser Irradiation Stimulates Proliferation of Keratinocyte Cultures: Involvement of Reactive Oxygen Species," Lasers in Surgery and Medicine vol. 22, pp. 212-218, 1998. 8 pages.

Hicks et al., "Enamel Carries Initiation and Progression Following Low Fluence (energy) and Argon Laser and Fluoride Treatment," The Journal of Clinical Pediatric Dentistry, vol. 20, No. 1 pp. 9-13, 1995. 6 pages.

Hsu et al., "Combined Effects of Laser Irradiation/Solution Flouride Ion on Enamel Demineralization," Journal of Clinical Laser Medicine and Surgery, vol. 16, No. 2 pp. 93-105, 1998. 13 pages.

Hulsbergen Henning et al. "Clinical and Histological Evaluation of Portwine Stain Treatment with a Microsecond-Pulsed Dye-Laser at 577 NM," Lasers in Surgery and Medicine, 4:375-380 (1984). 7 pages.

Hulsbergen Henning et al., "Port Wine Stain Coagulation Experiments with a 540-nm Continuous Wave Dye-Laser," Lasers in Surgery and Medicine, 2:205-210 (1983). 7 pages.

IPG Data Sheet for TFL Thulium Laser, Jun. 2001. 2 pges.

Ivanov, A.P. et al., "Radiation Propagation in Tissues and Liquids with Close Particle Packing," Zhurnal Prikladnoi Spektroskopii, vol. 47, No. 4, pp. 662-668 (Oct. 1987). English Translation. 6 pages.

Kalivradzhiyan et al., "The Usage of Low Intensity Laser Radiation for the Treatment of the Inflammatory processes of the Oral Cavity Mucosa after Applying Removable Plate Dentures," SPIE vol. 1984 pp. 225-230. (1995) 6 pages.

Karu, "Cell Attachment to Extracellular Matrices is Modulated by Pulsed Radiation at 820 nm and Chemicals that Modify the Activity of Enzymes in the Plasma Membrane," Lasers in Surgery and Medicine, vol. 29, pp. 274-281, 2001. 9 pages.

Karu, "Photobiological Fundamentals of Low-Power Laser Therapy," IEEE Journal of Quantum Electronics, vol. QE-23, No. 10, Oct. 1987, pp. 1703-1717. 15 pages.

Kazmina et al., "Laser Prophlaxis and Treatment of Primary Caries," SPIE vol. 1984, pp. 231-233. (1995) 3 pages.

Kozlov et al., "Laser in Diagnostics and Treatment of Microcirculation Disorders Under Parodontitis," SPIE vol. 1984, pp. 253-264. (1995) 12 pages.

Kuhns, J.G. et al., "Biological effects of laser radiation II: Effects of laser irradiation on the skin," NEREM Record, pp. 152-153, 1965. 4 pages.

Kuhns, J.G. et al., "Laser injury in skin," Laboratory Investigation, vol. 17, No. 1, pp. 1-13, Jul. 1967. 14 pages.

Levin, G. et al., "Designing with hysteretic current-mode control, " EDN Magazine, pp. 1-8, Apr. 11, 1996. www.edn.com/archives/1996/041196/08df5.htm, accessed Oct. 3, 2011, 8 pages.

Levin, G. et al., "Designing with hyseretic current-mode control," EDN Magazine, pp. 1-8, Apr. 28, 1994. www.edn.com/archives/1994/042894/09df3.htm, accessed Oct. 3, 2011, 8 pages.

Maegawa, et al., "Effects of Near-Infrared Low-Level Laser Irradiation on Microcirculation," Lasers in Surgery and Medicine, vol. 27, pp. 427-437, 2000. 12 pages.

Mamedova et al., "Microbiological Estimate of Parodontis Laser Therapy Efficiency," SPIE vol. 1984, pp. 247-249. 1995. 3 pages.

Mumford, "Effect of Soft Laser Treatment on Wound Healing in the Hamster Oral Mucosa," Lasers in Surgery and Medicine, Supplement 8, Abstracts, Abstract 25, pp. 6. 1996. 2 pages.

McDaniel, et al., "Hexascan: A New Robotized Scanning Laser Handpiece," Cutis, 45:300-305 (1990). 7 pages.

Nemeth, et al., "Copper vapor laser treatment of pigmented lesions," Lasers Surg. Med. Supp. 2:51 (1990). Abstract 214. 2 pages.

Ohbayashi, "Stimulatory Effect of Laser Irradiation on Calcified Nodule Formation in Human Dental Pulp Fibroblasts," J-Endod. Jan. 1999; 25(1): 30-3. 5 pages.

Oleinik, et al., "Automatized Securing Definition for Laser Therapy Indications in Case of Non-complicated Caries," SPIE, vol. 1984, pp. 238-244. 1995. 7 pages.

Orchardson, "Effect of Pulsed Nd:YAG Laser Radiation on Action Potential Conduction in Nerve Fibres Inside Teeth in vitro," J-Dent. Jul.-Aug. 1998; 26(5-6): 421-6. 7 pages.

Osigo et al, "Phase Transitions of Rat Stratum Corneum Lipids by an Electron Paramagnetic Resonance Study and Relationship of Phase States to Drug Penetration," Biochimica et Biophysica Acta 1301:97-104 (1996). 9 pages.

Ozawa et al., "Stimulatory Effects of Low-Power Laser Irradiation on Bone Formation in vitro," SPIE vol. 1984, pp. 281-288. 1995. 8 pages.

Petrischev et al. "Clinical and Experimental Low-Intense Laser Therapy in Dentistry," SPIE, vol. 1984, pp. 212-214. 1995. 3 pages.

Petrischev et al., "Report on Low Intensity Laser Radiation Usage in Dentistry," SPIE vol. 1984, pp. 202-211. 1995. 10 pages.

Powell, "Laser Dental Decay Prevention: does it have a future?" SPIE vol. 3192, pp. 2-5. 1997. 4 pages.

Rohrer, "Evaluating the Safety and Efficacy of a Novel Light Based Hair Removal System," Lasers. Surg. Med. Supp.13. Abstrace 97, p. 24 (2001). 2 pages.

Rotteleur, et al., "Robotized scanning laser handpiece for the treatment of port wine stains and other angiodysplasias," Lasers Surg. Med., 8:283-287 (1998). 6 pages.

Rubach et al., "Histological and Clinical Evaluation of Facial Resurfacing Using a Carbon Dioxide Laser With the Computer Pattern Generator," Arch Otolaryngol Head Neck Surg., 123:929-934 (1997). 7 pages.

Rylander, C.G. et al., "Mechanical Tissue Optical Clearing Devices: Enhancement of Light Penetration in Ex Vivo Porcine Skin and Adipose Tissue," Lasers in Surgery and Medicine, vol. 40, pp. 688-694 (2008). 7 pages.

Sandford et al., "Thermal Effects During Desensitisation of Teeth with Gallium-Aluminum-Arsenide Lasers," University of Queensland Dental School, Periodontology 15: 25-30 (1994). 6 pages.

Schindl, "Does Low Intensity Laser Irradiation Really Cause Cell Damage?" Laser in Surgery and Medicine vol. 29, pp. 105, 2001. 2 pages.

Sheehan-Dare, et al., "Lasers in Dermatology," British Journal of Dermatology, 129:1-8 (1993). 10 pages.

Shimizu et al., "Prospect of Relieving Pain Due to Tooth Movement During Orthodontic Treatment Utilizing a GA-AI-As Diode Laser," SPIE vol. 1984, pp. 275-280. 1995. 6 pages.

Shumilovitch et al., "Influence of Low Intensity Laser Radiation Upon the Microflora of Carious Cavities and Root Canal," SPIE vol. 1984, pp. 215-220. 1995. 6 pages.

Sing, "Electroacupuncture and Laser Stimulation Treatment: Evaluated by Somatosensory Evoked Potential in Conscious Rabbits," AM-J-Chin-Med. 1997; 25(3-4): 263-71. 9 pages.

Sokolova et al., "Low-intense Laser Radiation in Complex Treatment of Inflammatory Diseases of Parodontium," SPIE vol. 1984, pp. 234-237. 1995. 4 pages.

Sumian, C.C. et al., "A Preliminary Clinical and Histopathological Study of Laser Skin Resurfacing Using a frequency-Doubled Nd:YAG Laser After Application of Chromofilm®," Journal of Cutaneous Laser Therapy, vol. 1, pp. 159-166, 1999 8 pages.

Unger, "Laser Hair Transplantation III, Computer-assisted Laser Transplanting," Dermatol. Surg., 21:1047-1055 (1995). 10 pages.

Van Bruegel, "Power Density and Exposure Time of He-Ne Irradiation Are More Important Than Total Energy Dose in Photo-Biomodulation of Human Fibroblasts in Vitro," Lasers in Surgery and Medicine, vol. 12 pp. 528-537, 1992. 11 pages.

Walsh, "Laser "Curettage": a Critical Analysis," Periodontology 14:4-12, 1993. 9 pages.

Walsh, "The Current Status of Low Level Laser Therapy in Dentistry. Part 1. Soft Tissue Applications". Australian Dental Journal, 42(4):247-254 (1997) 8 pages.

Watanabe, S. et al., "The Effect of Pulse Duration on Selective Pigmented Cell Injury by Dye Lasers," The Journal of Investigative Dermatology, 88:523, 1987. Abstract. 2 pages.

Westerman et al., "Argon Laser Irradiation Effects on Sound Root Surfaces: In Vitro Scanning Electron Microscopic Observations," Journal of Clinical Laser Medicine and Surgery, vol. 16, No. 2, pp. 111-115, 1998. 6 pages.

Yules, R.B. et al., "The effect of Q-switched ruby laser radiation on dermal tattoo pigment in man," Arch Surg, vol. 95, pp. 179-180, Aug. 1967. 3 pages.

Zonios et al., "Skin Melanin, Hemoglobin, and Light Scattering Properties can be Quantitatively Assessed In Vivo Using Diffuse Reflectance Spectroscopy," Journal of Investigative Dermatology,117:1452-1457 (Dec. 2001). 7 pages.

US 6,230,044, 05/2001, Afanassieva et al. (withdrawn)

* cited by examiner

COOLING SYSTEM FOR A PHOTOCOSMETIC DEVICE

RELATED APPLICATIONS

This application is a continuation of application Ser. No. 10/154,756 ("the '756 application"), filed May 23, 2002, which claims priority to provisional application Ser. No. 60/363,798, filed Mar. 12, 2002. The '756 application is also a continuation-in-part of application Ser. No. 10/052,474, filed Jan. 18, 2002, which application is a continuation of application Ser. No. 09/473,910, filed Dec. 28, 1999, which application claims priority to provisional application Ser. No. 60/115,447, filed Jan. 8, 1999, claims priority from provisional application Ser. No. 60/164,492, filed Nov. 9, 1999, and is a continuation-in-part of application Ser. No. 09/078,055, filed May 13, 1998, now U.S. Pat. No. 6,273,884, which application claims priority to provisional application Ser. No. 60/046,542, filed May 15, 1997 and provisional application Ser. No. 60/077,726, filed Mar. 12, 1998. The '756 application is also a continuation-in-part of application Ser. No. 09/268,433, filed Mar. 12, 1999, which application claims priority to provisional application Ser. No. 60/115,447, filed Jan. 8, 1999 and provisional application Ser. No. 60/077,794, filed Jan. 8, 1999 and is a continuation-in-part of application Ser. No. 08/759,036, filed Dec. 2, 1996, now U.S. Pat. No. 6,015,404, and is a continuation-in-part of application Ser. No. 08/759,136, filed Dec. 2, 1996, now abandoned, and is a continuation-in-part of application Ser. No. 09/078,055, filed May 13, 1998, now U.S. Pat. No. 6,273,884, which application claims priority to provisional application Ser. No. 60/046,542, filed May 15, 1997 and provisional application Ser. No. 60/077,726, filed Mar. 12, 1998. The '756 application is also a continuation-in-part of application Ser. No. 09/634,981, filed Aug. 9, 2000, which application is a continuation of application Ser. No. 09/078,055, filed May 13, 1998, now U.S. Pat. No. 6,273,884, which application claims priority to provisional application Ser. No. 60/046,542, filed May 15, 1997 and provisional application Ser. No. 60/077,726, filed Mar. 12, 1998. The '756 application is also a continuation-in-part of application Ser. No. 09/847,043, filed Apr. 30, 2001, which claims priority to provisional application Ser. No. 60/200,431, filed Apr. 28, 2000. The '756 application also claims priority to provisional application Ser. No. 60/292,827, filed May 23, 2001. The '756 application also claims priority to provisional application Ser. No. 60/363,871, filed Mar. 12, 2002. The contents of all of these prior application specifications are incorporated herein by reference.

BACKGROUND OF THE INVENTION

Related Art

There exists a variety of conditions treatable using photocosmetic procedures (also referred to herein as photocosmetic treatments), including light-based (e.g., using a laser or lamp) hair removal, treatment of various skin lesions, tattoo removal, facial resurfacing, and skin rejuvenation. Currently, photocosmetic procedures are performed using professional-grade devices that cause destructive heating of target structures located in the epidermis/dermis of a patient's skin.

To date, photocosmetic procedures have been performed in a dermatologist's office, partially because of the expense of the devices used to perform the procedures, partially because of safety concerns related to the devices, and partially because of the need to care for optically induced wounds on the patient's skin. Such wounds may arise from damage to a patient's epidermis caused by the high-power radiation and may result in significant pain and/or risk of infection. While certain photocosmetic procedures, such as $CO_2$ laser facial resurfacing, will continue to be performed in the dermatologist's office for medical reasons (e.g., the need for post-operative wound care), there are a large number of photocosmetic procedures that could be performed in a non-medical environment (e.g., home, barber shop, or spa) if the consumer could perform the procedure in a safe and effective manner. Even for procedures performed in a medical environment, reduced skin damage would reduce recovery time.

Photocosmetic devices for use in medical or non-medical environments may benefit from following characteristics: (1) The device must be safe. For example, it is necessary to avoid eye and skin injuries. (2) Preferably the device is easy to use, thus allowing an operator to achieve acceptable cosmetic results after only reading a brief training period. (3) Preferably the device is robust and rugged enough to withstand abuse. (5) Preferably the device is easy to maintain. (6) Preferably the device is manufacturable in high volume. (7) Preferably the device is available at a reasonable price. (8) Preferably the device is small and easily stored, for example, in a bathroom. Currently available photocosmetic devices have limitations related to one or more of the above challenges.

SUMMARY OF THE INVENTION

A first aspect of the invention is a photocosmetic device for use on an area of a patient's skin comprising a treatment head for use in close proximity to the patient's skin, at least one source of electromagnetic radiation positioned within the treatment head and configured to project radiation onto the area of skin, a cooling surface thermally coupled to the at least one source, and a mechanism to direct a phase change substance onto the cooling surface. Optionally, the phase change substance comprises a liquid. Alternatively, the phase change substance comprises a solid.

In some embodiments of the first aspect, the surface has a texture. The texture may be a linear groove pattern or a concentric groove pattern. Alternatively, the texture is a plurality of projections. The mechanism may be a spray jet. The mechanism may further comprise a valve coupled to the spray jet, wherein the valve controls the amount of liquid projected onto the cooling surface. A heat sensor may be used to produce a signal indicative of the temperature of at least a portion of the area of skin, and a controller maybe be used to receive the signal from the heat sensor and control the valve in response to the temperature.

A container may be included to hold the substance. In some embodiments, the substance is a refrigerant. For example, the refrigerant comprises tetra flouroethane. The solid may be ice or an organic compound, or an Ga/In alloy.

The cooling surface may be a thermally conductive electrode providing power to the source. Alternatively, the cooling surface may be a surface of a thermally conductive heat sink that is thermally coupled to the source. The cooling surface may have at least one channel therethrough to receive the phase change substance. Alternatively, the cooling surface has a plurality of channels therethrough to receive the phase change substance, the plurality of channels aligned along the length.

A second aspect of the invention is a photocosmetic device for use on an area of a patient's skin comprising a treatment head for use in close proximity to the patient's skin, at least one electromagnetic radiation source configured to project radiation through the treatment head onto the area of skin, and a first mechanism coupled to the treatment head and configured to project a first substance onto the patient's skin. The electromagnetic radiation source may be positioned within the treatment head. The device may include an optical system to transmit radiation to the area of skin, the optical system having a surface configured to contact the patient's skin. The device may further comprise a cooling surface thermally coupled to the at least one source and said surface; and second mechanism to project a phase change substance onto the cooling surface, wherein the first mechanism is configured to use a gas formed by the phase change of the second substance to drive the first substance onto the patient's skin. The device may further comprising a cooling surface thermally coupled to the source and said surface, and a second mechanism configured to project a portion of the first substance onto the cooling surface.

The first substance may be a liquid and the portion of the first substance projected onto the skin is a gas resulting from a phase change of the first substance. Alternatively, the first substance is a solid and the portion of the first substance projected onto the skin is a liquid resulting from a phase change of the first substance. In yet another alternative, the first substance is a solid and the portion of the first substance projected onto the skin is a gas resulting from a phase change of the first substance.

The first substance may be a liquid, and the liquid may be a lotion. Alternatively, the first substance may be a gas, and the gas may be cooled air. The second substance may comprise a plurality of components. The cooling surface may be a surface of a thermally conductive electrode providing power to the source. The cooling surface may be a surface of a thermally conductive heat sink that is thermally coupled to the source. Optionally, the source is one of a diode laser bar, light emitting diode and lamp.

A third aspect of the invention is a device for use on an area of a patient's skin comprising a treatment head for use in close proximity to the patient's skin, at least one electromagnetic radiation source positioned in the treatment head and configured to project electromagnetic radiation onto the area of skin, a cooling surface thermally coupled to the at least one source of electromagnetic radiation and including at least one channel therethrough, and a mechanism to project a substance onto the cooling surface, and into the at least one channel.

The substance may be a liquid or a gas.

A fourth aspect of the invention is a device for use on an area of a patient's skin comprising at least one electromagnetic radiation source configured to project radiation onto the area of skin, a cooling surface thermally coupled to the at least one source, and a solid mass thermally coupled to the cooling surface, the solid mass changing phase in response to heat absorbed from the cooling surface.

In some embodiments the solid mass is ice or may be dry ice. The device may further comprise a mechanism to bring the solid mass into contact with the cooling surface. The device may further comprise a treatment head, wherein the source is positioned within the treatment head. The source may be one of a diode laser bar, light emitting diode and lamp.

The cooling surface is a surface of a thermally conductive electrode providing power to the source or a thermally conductive heat sink that is thermally coupled to the source.

A fifth aspect of the invention is a device for use on an area of a patient's skin comprising at least one electromagnetic radiation source configured to project electromagnetic radiation onto the area of skin, a cooling surface thermally coupled to the at least one source, a solid mass thermally coupled to the cooling surface, at least a portion of the mass becoming a liquid in response to absorption of heat from the cooling surface, and an exhaust vent configured to receive a portion of the liquid and project the portion of the liquid onto the patient's skin.

The device may further comprise a mechanism for combining the liquid with a chemical substance and directing the liquid and chemical combination onto the patient's skin.

A sixth aspect of the invention is a device for use on an area of a patient's skin comprising at least one electromagnetic radiation source configured to project electromagnetic radiation onto the area of skin, a cooling surface thermally coupled to the at least one source, and a reaction chamber thermally coupled to the cooling surface and containing at least a first chemical compound and a second chemical compound, the first and second chemical compounds selected to provide an endothermic reaction within the reaction chamber.

The cooling surface may be a surface of a thermally conductive electrode providing power to the source, or the cooling surface may be a surface of a thermally conductive heat sink that is thermally coupled to the source.

A seventh aspect of the invention is a device for use on an area of a patient's skin comprising a treatment head for use in close proximity to the patient's skin, at least one source of electromagnetic radiation positioned in the treatment head and configured to project electromagnetic radiation onto the area of skin, and a cooling surface thermally coupled to the at least one source of electromagnetic radiation, the cooling surface having a channel therethrough to allow a low-boiling point liquid to flow onto a surface of the cooling surface.

The device may further comprise a valve connected to the channel to control the evaporation of the low-boiling point liquid. The device may also further comprise a heat sensor to produce a signal indicative of the temperature of the area of skin, and a controller to receive the signal from the heat sensor and control the valve in response to the signal. The device may have a pressure source is coupled to the channel to control the boiling of the low-boiling point liquid. The source is one of a laser diode bar, light emitting diode and lamp.

The eighth aspect of the invention is a device for use on an area of a patient's skin comprising a treatment head for use in close proximity to the patient's skin, at least one electromagnetic radiation source positioned in the treatment head and configured to project radiation onto the area of skin, a heat spreader thermally coupled to the at least one source, and a cooling surface thermally coupled to the heat spreader. The source may be one of a diode laser bar, light emitting diode and lamp. The cooling surface may be a surface of a thermally conductive electrode providing power to the source, or may be a surface of a thermally conductive heat sink that is thermally coupled to the source.

A ninth aspect of the invention is a cooling system for cooling a heat generating device a cooling surface thermally coupled to the heat generating device, and a nozzle configured to project a high pressure liquid, the liquid forming a flowing liquid on the cooling surface. The high pressure liquid may be projected such that the liquid forms a stream of liquid the entire distance between the nozzle and the cooling surface. The cooling surface may be textured. Optionally the cooling system may further comprise a cooling chamber to redirect the liquid to the cooling surface. The cooling chamber may include sidewalls and a cover. While many of the embodiments are described with reference to performing photocosmetic treatments in a non-medical environment, it is to be understood that the benefits of aspects of this invention apply to medical devices as well as non-medical devices, and the invention applies to either without limitation.

BRIEF DESCRIPTION OF THE DRAWINGS

Illustrative, non-limiting embodiments of the present invention will be described by way of example with reference to the accompanying drawings, in which the same reference numeral is for the common elements in the various figures, and in which.

DETAILED DESCRIPTION OF THE INVENTION

Figure 1:
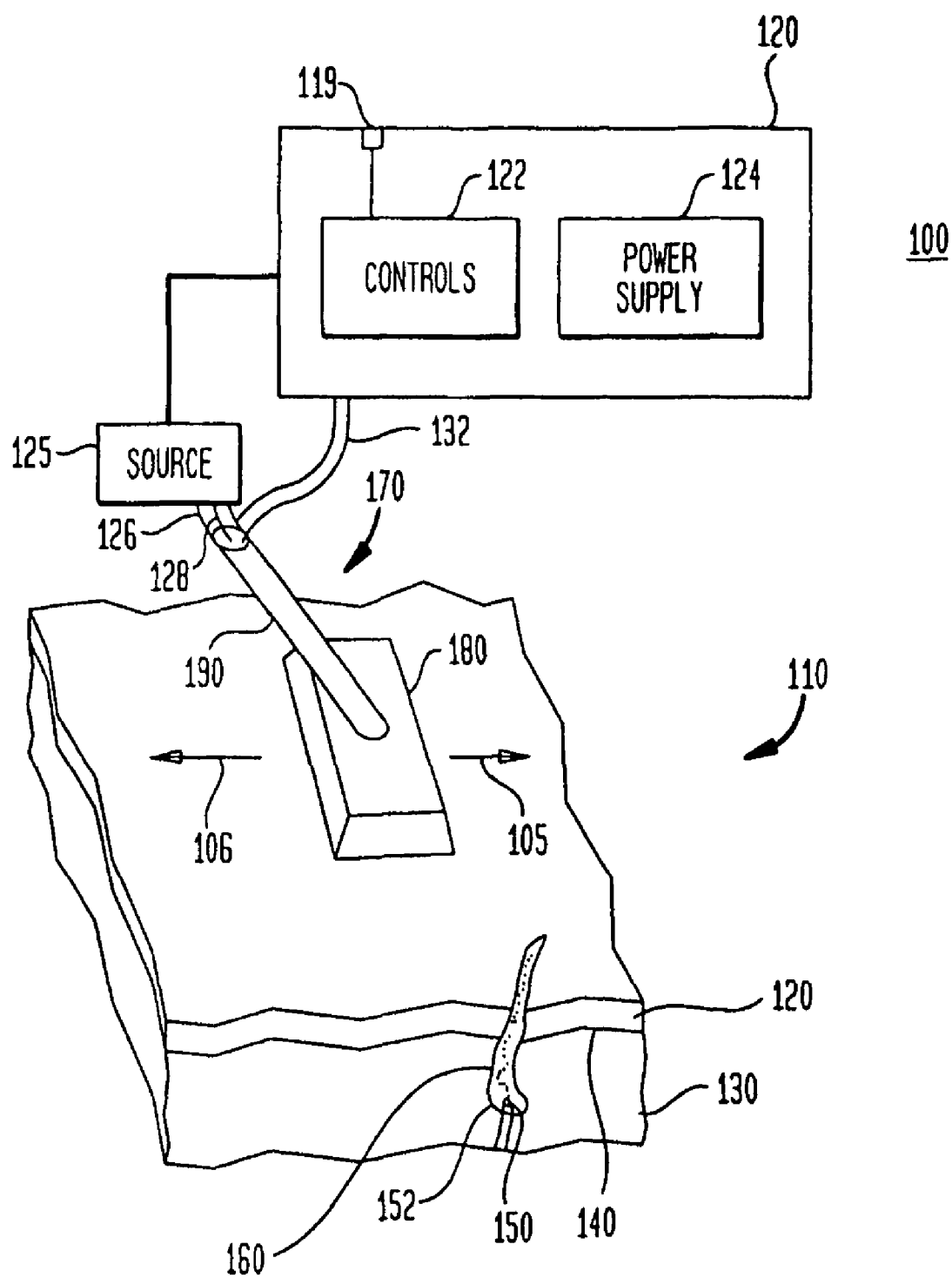
FIG. 1 is a schematic illustration of some basic elements of a photocosmetic device according to some aspects of the present invention.

FIG. 1 is a schematic illustration of some basic elements of a photocosmetic device 100 according to some aspects of the present invention. Area 110 is an area of a patient's skin on which a selected photocosmetic treatment is to be performed. Area of skin 110 has a basal layer 140 in between an epidermal layer 120 and a dermal layer 130. Typically, photocosmetic treatments involve treating a target area located within epidermal layer 120 or dermal layer 130. For example, in the case of hair removal, it may be desirable to heat a bulb 150 of a hair follicle 160. Alternatively, only a portion of bulb 150 may be heated, for example, the basement membrane 152 between the papilla and the follicle.

In some embodiments of the present invention, the major sub-systems of device 100 include a handpiece 170, a base unit 120 and cord 126 to couple handpiece 170 to base unit 120. Base unit 120 may include a power supply 124 to power control electronics 122 and electromagnetic radiation (EMR) source 125. Power supply 124 can be coupled to handpiece 170 via cord 126. Cord 126 is preferably lightweight and flexible. Alternatively, as described with reference to FIG. 21 below, cord 126 may be omitted and base unit 120 may be used as a charging station for a rechargeable power source (e.g., batteries or capacitors) located in handpiece 170. In some embodiments, base unit 120 can be completely eliminated by including a rechargeable power source and an AC adapter in the handpiece 170.

Handpiece 170 includes a treatment head 180 (also referred to simply as a head) configured to be in contact with a patient's skin, and a handle 190 that may be grasped by an operator to move head 180 in any direction across the patients skin. For example, head 180 may be pushed across the skin in a forward direction 105 or pulled across the skin in a backward direction 106. Typically, during a given stroke, contact will be maintained between head 180 and the patient's skin 110 while head 180 is moved. Handpiece 170 may be mechanically driven or hand-scanned across the skin surface of area 110. Firm contact between head 180 and skin 110 is preferable to ensure good thermal and optical contact. As described in greater detail below, in some embodiments of the present invention, head 180 and/or area of skin 110 are cooled by a passive or active cooling apparatus to prevent damage to the head and reduce the occurrence of skin damage (e.g., wounds).

In an exemplary embodiment, source 125 is located in handpiece 170, for example in head 180. Alternatively, source 125 is located in base unit 120 and connected to head 180 via an optical fiber 128. Optical fiber 128 may extend through handle 190, or may be otherwise connected to head 180 for the purpose of delivering light to the patient's skin.

In some embodiments, controls 122 receive information from head 180 over lines 132, for example information relating to contact of head 180 with skin 110, the rate of movement of head 180 over the patient's skin, and/or skin temperature. Controls 122 may transmit control signals to head 180 over lines 132. Lines 132 may be part of a cable that is also connected to head 180 through handle 190 or may be otherwise connected to the head. Controls 122 may also generate outputs to control the operation of source 125 and may also receive information from the source. Controls 122 may also control a selected output device 119, for example an audio output device (e.g., buzzer), optical output device, a sensory output device (e.g., vibrator), or other feedback control to an operator. Depending on operator preference, other commonly used output devices may also be used. In some embodiments, output device 119 is located within handpiece 170.

Figure 2A:
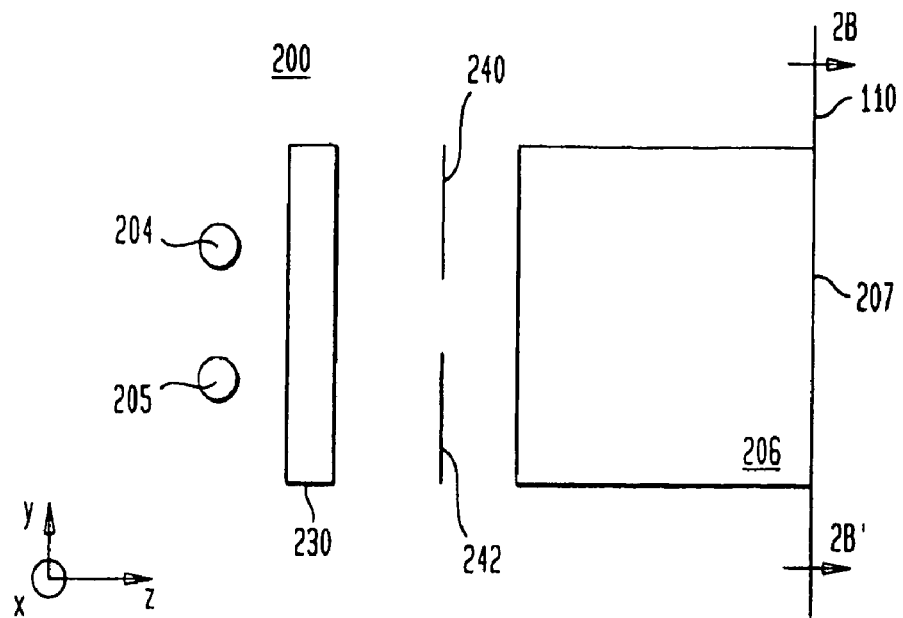
FIG. 2A is a side view of one example of a radiation system according to some aspects of the present invention for use in performing a photocosmetic procedure on an area of a patient's skin.
Figure 2B:
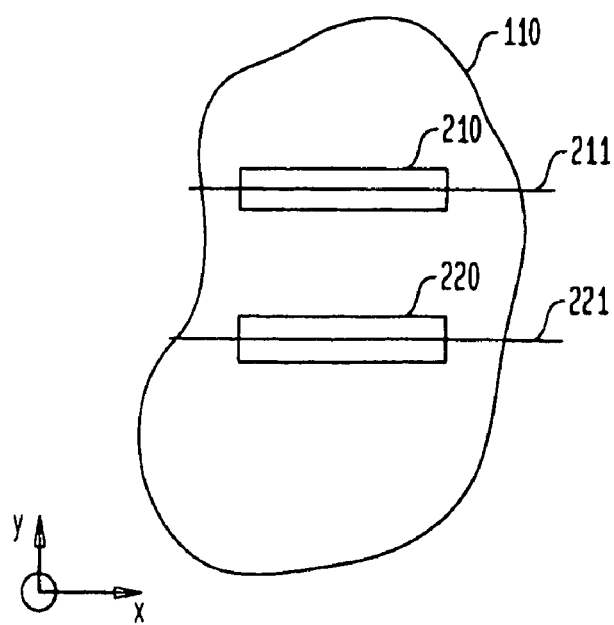
FIG. 2B is a schematic top view of an irradiated area of a patient's skin taken along lines 2B-2B' of FIG. 2A.

FIG. 2A is a side view of one example of an illumination system 200 according to some aspects of the present invention for use in performing a photocosmetic procedure on an area of a patient's skin 110. FIG. 2B is a schematic top view of an irradiated area of a patient's skin 110 taken along lines 2B-2B' of FIG. 2A. In an exemplary embodiment of the invention, system 200, including an EMR source 204, is located in the head of a photocosmetic device (e.g., head 180 in FIG. 1) such that the EMR source is located proximate the skin surface 110.

Depending on the treatment to be performed, source 204 may be configured to emit at a single wavelength, multiple wavelengths, or in a wavelength band. Source 204 may be a coherent light source, for example a ruby, alexandrite or other solid state laser, gas laser, diode laser bar, or other suitable laser light source. Alternatively source 204 may be an incoherent light source for example, an LED, arc lamp, flashlamp, fluorescent lamp, halogen lamp, halide lamp or other suitable lamp.

An optical system 206, comprised of a plurality of optical elements, includes a surface 207 for transmitting radiation from an EMR source 204 and for contacting the patient's skin 110. Further details of optical system 206, are given below with reference to FIG. 12-16. The phrase "optical system" is used herein to refer to a system for transmitting any type of optical radiation suitable for performing photocosmetic procedures.

In some embodiments, source 204 has an extended dimension in the x-direction (e.g., the light source is substantially linear). One of ordinary skill would understand that a plurality of point sources may be combined to form a substantially linear source. Additionally, relatively small linear sources may be combined to form a single, longer continuous linear source, or a longer linear source having one or more discontinuities. For example, source 204 may be a diode laser bar having a 1 cm long emission line and a few micron line width; optionally source 204 may include two or three bars placed in a line along the x-direction to create a 2 cm or 3 cm long emission line.

Alternatively, linear sources may be placed adjacent to one another in the y-direction to form a source having an increased line width. System 200 may include one or more additional sources 205, similarly or differently configured than the one or more sources 204. In embodiments having two sources, source 204 and source 205 may emit at the same or different wavelength ranges.

In embodiments having multiple EMR sources 204, 205, it may be desirable to activate only selected sources for a given treatment. For example, in embodiments having sources emitting at different wavelengths, for certain applications, for example, hair removal, it may be preferable to only activate a selected one or more sources and for certain other applications, for example, acne treatment or skin rejuvenation, to activate a selected one or more other sources. While sources are discussed as emitting radiation at a wavelength, one of ordinary skill would understand that any radiation source produces light over a finite range of wavelengths, accordingly a specified wavelength may be a part of a broader range.

Radiation source 204 may be a pulsed or continuous wave (CW) source. For applications that require coverage of large areas such as hair removal, CW diode laser bars may be preferable. A method of utilizing continuous wave (CW) light sources for the treatment of various dermatologic disorders is described in U.S. Pat. No. 6,273,884 B1 entitled "Methods and Apparatus for Dermatology Treatment," to Altshuler, et al., the substance of which is hereby incorporated by reference. Some aspects of that patent teach the use of a CW light source in combination with a contact optical delivery system that can be either hand scanned or mechanically driven across the skin surface to create a precise temperature rise in the targeted biological structures (i.e., using continuous contact scanning (CCS)).

Most commercial diode laser bars exhibit lifetimes of >5000 hours, but application according to the present invention may only require 10-100 hour lifetimes. Accordingly, in some embodiments of the present invention, a source 204 may be overdriven with current to increase radiation output, thus causing the diode laser to operate at a higher temperature, and thereby sacrificing lifetime.

Diode laser bars appropriate for use with the present invention include diode laser bars emitting at wavelengths of 790-980 nm or other suitable wavelengths. Examples of sources of diode laser bars appropriate for use with aspects of the present invention include Coherent Inc. of Santa Clara, Calif., or Spectra Physics of Mountain View, Calif. The above examples of sources 204, 205 are exemplary and it should be understood that aspects of the present invention include devices and apparatus using any appropriate EMR source currently available or yet-to-be-developed.

For some embodiments of the present invention, for example those requiring either low power or for treatment of small areas of a patient's skin, LEDs may be used as light sources 204, 205. LEDs are available in a wide range of emission wavelengths. Similar to the diode laser sources discussed above, multiple LEDs emitting at different wavelengths could be used in a single optical system. Typical lifetimes for LEDs are in the 50,000-hour range; similar to laser diodes, it may be possible to overdrive an LED and sacrifice lifetime to generate higher optical power. For applications that require high power density, a reflective concentrator (e.g., a parabolic reflector) could be used to decrease the spot size at the skin surface.

Broadband sources (e.g., low-power halogen lamps, arc lamps and halide lamps) are another type of light source that could be used as sources 204, 205. One or more optical filters 240 and 242 can be used to provide a wavelength band of interest for a given application. Multiple lamps can be combined to produce high power, and, similar to the case of LEDs, a concentrator could be used to decrease the spot size at the skin surface. In some embodiments, several different types of light sources can be incorporated into a photocosmetic device (e.g., device 100 of FIG. 1).

In some embodiments of system 200, a beam splitter 230 splits radiation from source 204 to form a first portion of EMR and a second portion of EMR. The first portion and second portion may be filtered by filters 240 and 242 respectively. After filtering, the portions may have the same or different wavelength ranges. The functions of the first and second portions may be the same or different. For example, the function of the second portion of EMR may be to preheat the patient's skin 110 in preparation for treatment by the first portion of EMR. Alternatively, both the first portion of EMR and the second portion of EMR may provide treatment.

Referring to FIG. 2B, in some embodiments, optical system 206 (visible in FIG. 2A) is configured to form a first area of radiation 210 along a first axis 211 on the patient's skin 110. First area of radiation 210 is formed from at least a first portion of electromagnetic radiation from source 204 (visible in FIG. 2A). In some embodiments, a second area of radiation 220 along a second axis 221 is formed on the patient's skin 110. Second area of radiation 220 may be formed from a second portion of electromagnetic radiation from the radiation source 204; alternatively second area of radiation 220 may be formed from light from second radiation source 205 (visible in FIG. 2A).

In some aspects of the present invention, the first axis 211 and second axes 221 are parallel; however in other embodiments, the axes 211, 221 are not parallel. System 206 may be configured to form the first area 210 a selected distance from the second area 220, or may be configured such that the first portion of radiation overlaps at least a part of the second portion of radiation. Optionally, system 206 is configured to form (e.g., focus or collimate) the first portion and second portion substantially as lines. Optical system 200 may be configured to produce one or more lines of light at the skin surface, each having a length of 1-300 mm and a width of 0.1-10 mm. Astigmatism of the beam can be in the range 0.01-0.5. The term "astigmatism" is herein defined to mean the ratio of beam width to the beam length. Also, optionally, system 206 may be configured to form one or more additional areas of radiation along additional axes (not shown) on the patient's skin 110, the additional areas of radiation formed from corresponding additional portions of electromagnetic radiation from the radiation source 204 or 205, or radiation from one or more additional radiation sources.

Figure 3:
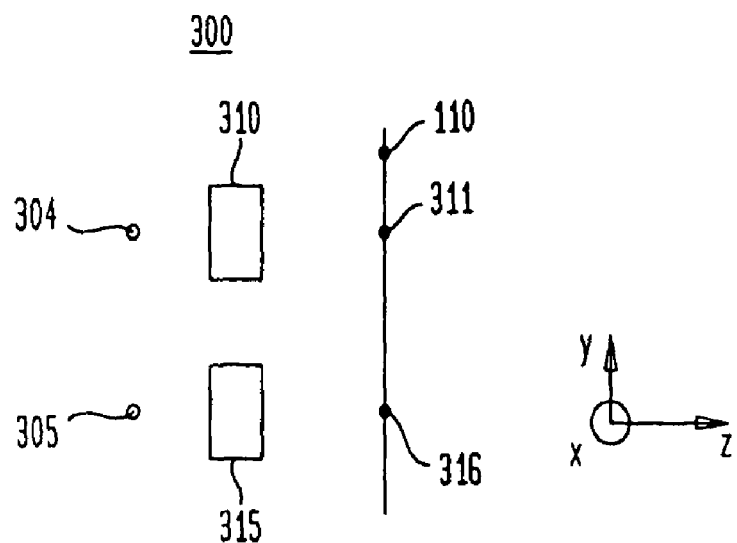
FIG. 3 is a side view of an example of a radiation system that is capable of forming two areas of radiation on an area of a patient's skin.

FIG. 3 is a side view of another example of an illumination system 300 for use in performing photocosmetic procedures, that is capable of forming two areas of radiation 311, 316 on an area of a patient's skin 110. In system 300, two optical systems 310, 315, instead of a single optical system 206 (FIG. 2), each generate a corresponding area of radiation 311, 316 (e.g., areas of radiation 210, 220). The radiation used to generate the lines may be from two sources 304, 305 or a single divided source as described above with reference to FIG. 2.

Figure 4:
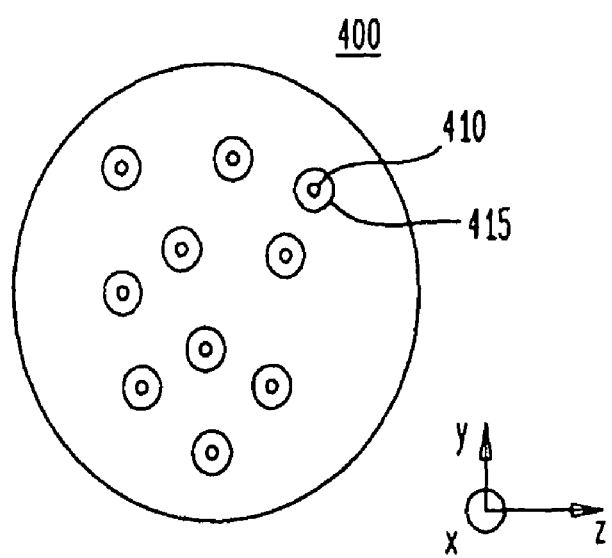
FIG. 4 is a top view of one example of a system appropriate for formation of islands of treatment.

FIG. 4 is a top view of one example of an illumination system 400 appropriate for formation of islands of treatment. System 400 includes a plurality of sources 410 (e.g., a conventional laser diode emitting a line or circular spot of illumination), each having a corresponding optical system 415 to direct light onto an area of skin. The illustrated system may be used to create a square (or arbitrarily shaped) matrix of focal spots having islands of treatment within the area of skin. The term "island" as used here is defined to mean an area of specified treatment separated from other areas of the specified treatment, such that areas between two or more areas receive radiation in an amount below that necessary to achieve the specified treatment. Islands of illumination are discussed in greater detail in U.S. Provisional patent application Ser. No. 10/033,302, filed Dec. 27, 2001, by Anderson, entitled "Method and Apparatus for EMR Treatment" the substance of which is hereby incorporated by reference.

For embodiments of photocosmetic devices according to the present invention that utilize high-power sources, management of waste heat from the sources is important for avoiding wounds and other injuries to the consumer. For example, in the case of a photocosmetic device that includes diode laser bars in the handpiece, up to 60% of the electrical energy may be dissipated in non-optical waste heat. In addition to the removal of heat to avoid wounds, removal of heat may be important to prevent the source from overheating and shortening the lifetime of the source.

Figure 5:
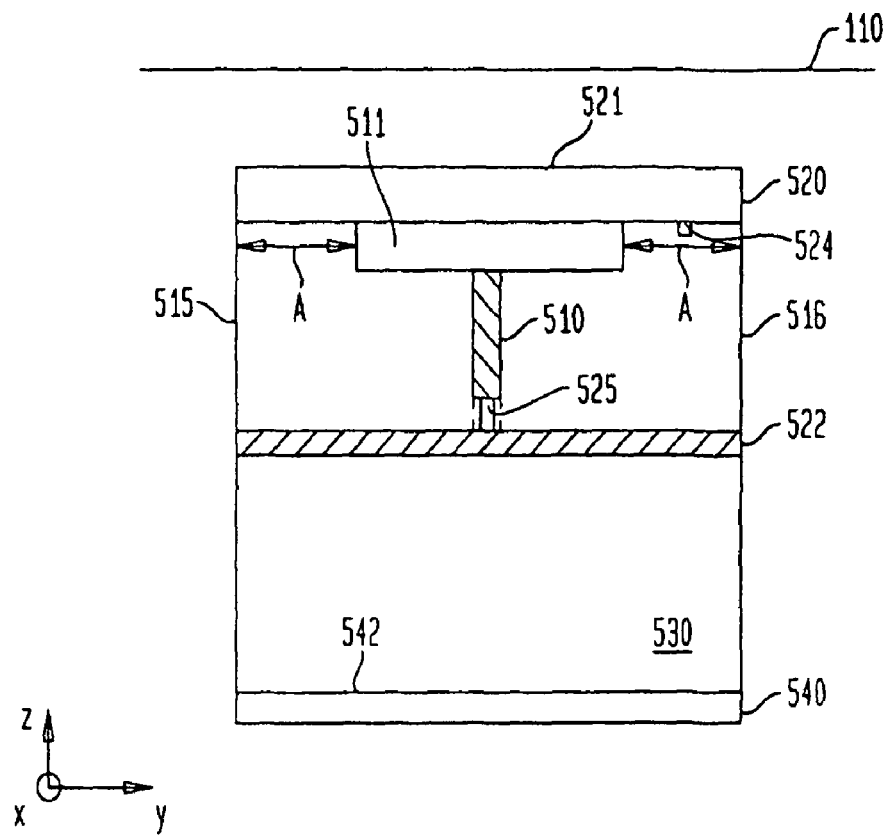
FIG. 5 is a schematic cross-sectional side view of one embodiment of a head according to aspects of the present invention.

FIG. 5 is a schematic cross-sectional side view of one embodiment of a head 500 according to aspects of the present invention. Head 500 includes an illumination system including an EMR source (e.g., diode laser bar 510) and an optical system 520. Head 500 may be located in a housing to protect the optical components and to protect the operator of a photocosmetic device; the housing is omitted to avoid obfuscation. In FIG. 5, a diode laser bar 510 operates as the source of electromagnetic radiation (e.g., source 204 in FIG. 2) and may be used to form one or more areas of radiation (e.g., 210, 220 in FIG. 2). Diode laser bar 510 is located between positive electrode 515 and negative electrode 516. Electrodes 515, 516 provide electrical power to diode laser bar 510, and may be made of any suitable material having good electrical conductivity. In some embodiments, electrodes 515, 516 are in thermal contact with diode laser bar 510, and have good thermal conductivity to transfer waste heat away from diode laser bar 510. For example, electrodes 515 and 516 may be made of aluminum or copper.

Optionally, waste heat from diode laser bar 510 may be transferred via electrodes 515 and 516 to a heatsink 530. Heat sink 530 may be made of any material having good thermal conductivity to transfer waste heat away from diode bar 510. For example, heat sink 530 may be made of aluminum or copper. Heat sink 530 can be cooled by any appropriate, known method of cooling including a stream of air. Optionally, cooling may be enhanced by adding fins (not shown) to heat sink 530. Alternatively, heat sink 530 may be cooled by one or more of the heat removal methods discussed below with reference to FIGS. 6-11. Also optionally, a heat spreader 522 may be located between electrodes 515, 516 and heatsink 530. Heat spreader 522 is thermally coupled to electrodes 515, 516 and heat sink 530. Heat spreader 522 may be made of any suitable material having good thermal conductivity; preferably heat spreader 522 is electrically insulative. Diamond and carbon fiber are two examples of materials suitable for use as heat spreaders.

In some embodiments, electrodes 515, 516 are configured to be heat sinks to conduct waste heat away from diode laser bar 510. Accordingly, heat sink 530 and heat spreader 522 may be omitted. In such embodiments, electrodes 515 and 516 can be made of any materially exhibiting good thermal and electrical conductivity. Optionally, one or more thermal sensors 524 (e.g. a thermocouple, a thermistor) may be used to monitor a temperature indicative of a patient's skin (e.g., the temperature at the interface of an optical system 520 and electrode 516) for use in a cooling system as described below.

Diode laser bar 510 may be secured to electrodes 515 and 516 using any method capable of maintaining good electrical contact between bar 510 and electrodes 515,516. In embodiments where transfer of waste heat is desired, any suitable method of achieving good thermal and electrical contact may be used. In one embodiment, diode laser bar 510 is clamped between the two electrodes 515 and 516. A spring or other suitable device may be used to clamp diode laser bar 510 firmly between electrodes 515, 516. In another embodiment, diode laser bar 510 may also be glued in place with thermal/electrical conductive epoxy. In another embodiment, diode laser bar 510 is soldered in place with a low-temperature solder (In or Au/Sn solder, etc.). Automated soldering may be achieved using an indium preform placed between diode laser bar 510 and electrodes 515 and 516, and applying heat using a die bonder to heat, compress, and then cool the solder and diode bar. Optionally, a spacer 525, made out of a material with high thermal and low electrical conductivity such as BeO, may be included to provide electrical insulation between the electrodes 515 and 516.

According to some aspects of the present invention, optical system 520 couples light from diode laser bar 510 to a patient's skin. Optical system 520 may be separated from diode laser bar 510 by an air gap 511. Exemplary optical systems 520 are described in greater detail below with reference to FIGS. 12-15. In embodiments according some aspects of the present invention, optical system 520 is configured to contact an area of a patient's skin, and the optical surface 521 is cooled to provide cooling to the patient's skin.

In some embodiments, cooling of diode laser bar 510 and optical system 520 are achieved using a single cooling system. For example, electrodes 515, 516 may be thermally coupled to optical system 520 along dimensions A; accordingly, both diode laser bar 510 and optical system 520 may be cooled by cooling the electrodes 515, 516 directly or via cooling of a heat sink 530 that is thermally coupled to electrodes 515, 516. Dimensions A are typically both between roughly 1 and 10 mm. Further detail regarding simultaneous cooling of an optical source and an optical system are given in U.S. application Ser. No. 09/473,910, filed Dec. 28, 1999, the substance of which is hereby incorporated by reference.

Contact cooling of the skin may be used to protect a patient's epidermis during delivery of high-fluence radiation to the skin, for example at wavelengths where melanin exhibits significant absorption. In some embodiments of head 500, optical system 520 includes a sapphire element configured to contact a patient's skin due to its good optical transmissivity and thermal conductivity. As described above, optical system 520 may be cooled to remove heat from the sapphire element during treatment. Optionally, prior to treatment with the photocosmetic device, a lotion that is transparent at the operative wavelength(s) may be applied on the skin. Preferably, the location is thermally conductive to enhance heat removal from the skin through optical surface 521. Preferably, the lotion also facilitates the gliding motion of the optical system 520 over the skin surface and has a refractive index match between contact surface 520 and the skin 110 to provide efficient optical coupling of the radiation into the skin.

The lotion may also be used to show which skin areas have been treated by choosing a lotion with optical properties (e.g., color or reflectance) that are altered in response to irradiation by an EMR source (e.g., laser diode 510). For example, if the lotion is initially a given color, after irradiation it would become transparent (or a different color). The ability to distinguish treated from untreated areas is particularly important for treatments such as hair removal that are performed over a large surface area.

FIG. 5 also illustrates one embodiment of a system for cooling diode bar 510 and optical system 520 via heat sink 530. In FIG. 5, a heat absorbitive liquid flows through a thermally conductive conduit 540 that is thermally coupled to heatsink 530. For example, in one embodiment, water is used as the liquid. Optionally water may be provided by attaching a source of cold water, such as tap water; referring to FIG. 1, water may be provided through a handle 190 having suitable plumbing. Alternatively, a closed-circuit cooling loop having a heat exchanger (not shown) to remove heat from the liquid; the heat exchanger may be located in handle 190 or base unit 120.

Referring again to FIG. 5, conduit 540 covers at least a portion of one or more surfaces, for example, surface 542 of heat sink 530. A single planar conduit may cover the entirety of one or more surfaces of heat sink 530. Alternatively, a plurality of conduits, each covering a portion of a surface heatsink 530, may be used. Alternatively, one or more conduits 540 may cover at least a portion of electrodes 515, 516. Since cooling may be applied to either heat sink 530, directly to electrodes 515, 516, a surface of a heatsink (e.g., surface 542), a surface of an electrode, or any other appropriate surface from which heat is to be removed shall hereinafter be referred to as a "cooling surface." While a cooling surface is illustrated as an external surface, it is to be understood that a cooling surface may be an internal surface, such as a surface exposed to a conduit through a heat sink or an electrode.

Figure 6A:
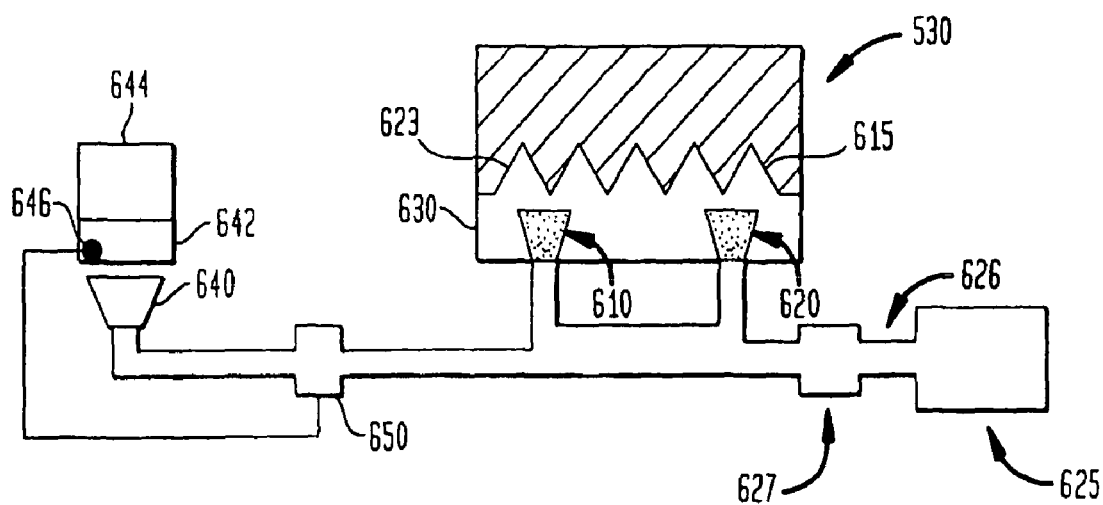
FIG. 6A is a cross-sectional side view one example of one embodiment of a cooling system that uses evaporative cooling.

FIG. 6A is a cross-sectional side view one example of one embodiment of a cooling system 600 that uses evaporative cooling. In FIG. 6, a phase change liquid is sprayed from one or more spray jets 610 and 620 onto the cooling surface 623. The liquid can be any suitable evaporative liquid, such that the liquid evaporates in response to heat absorbed from the cooling surface. In some embodiments, the liquid is a low-temperature boiling-point liquid, directed on the heat sink such that as the liquid boils in response to heat absorbed from the cooling surface 623. In some embodiments, the liquid is tetrafluoroethane (boiling point −26° C.), $CO_2$ (boiling point −78° C.) although any other suitable liquids (e.g., freon or liquid nitrogen) could also be used. In some embodiments, the liquid is atomized by spray jets 610 and 620.

Optionally, the liquid can be contained in a container 625 located in the base unit or handle. Preferably, container 625 is conveniently accessible by a user so as to be user-replaceable. A conduit 626 is used to transport the liquid to spray jets 610 and 620. The amount of coolant flow is regulated by valve 627, which can be controlled manually or electrically using information regarding the amount of heat present in a system (e.g., system 500 of FIG. 5). For example, a sensor (e.g., sensor 524 in FIG. 5) can be used to control a feedback-controlled solenoid in valve 627. Optionally, each spray jet 610 and 620 can be a combination valve and spray jet eliminating the need for a separate valve 627.

Optionally, the cooling surface 623 from which evaporation occurs can be textured to increase the surface area from which the liquid can be evaporated. Although triangular texturing 615 of the evaporative surface is shown, any shape suitable for increasing surface area may be implemented. The illustrated triangular texturing 615 may be a part of a linear grooves pattern, a cross-sectional view of a concentric circular groove pattern or any other appropriate groove pattern. Other texturing includes a plurality of projections (e.g, semi-spheres, cylinders, or pyramids projecting from the cooling surface). Optionally, a collar 630 may be used to surround spray jets 610, 620 and heat sink 530 to contain the spray.

A phase change liquid may also be used to cool the electronics 644 used to power and/or control a photocosmetic device. In particular, power field effect transistors (FETs) used to control the power of a photocosmetic device generate a large amount of heat. Conventionally, power FETs have been cooled using a relatively large heat sink, and a fan to remove heat. Such systems tend to be large and heavy. Cooling systems according to the present invention provide an alternative method of cooling.

Optionally, a portion of the phase change liquid conduit 626 that provides liquid to remove heat generated by the EMR source may be configured to direct a portion of the phase change liquid to the spray jet 640. Spray jet 640 directs a portion of the phase change liquid onto a cooling surface (e.g., a surface of a heat sink 642). A heat sensor 646 (e.g., a thermistor) may be used to control the amount of liquid projected onto cooling surface, for example, by controlling a valve 650.

Figure 6B:
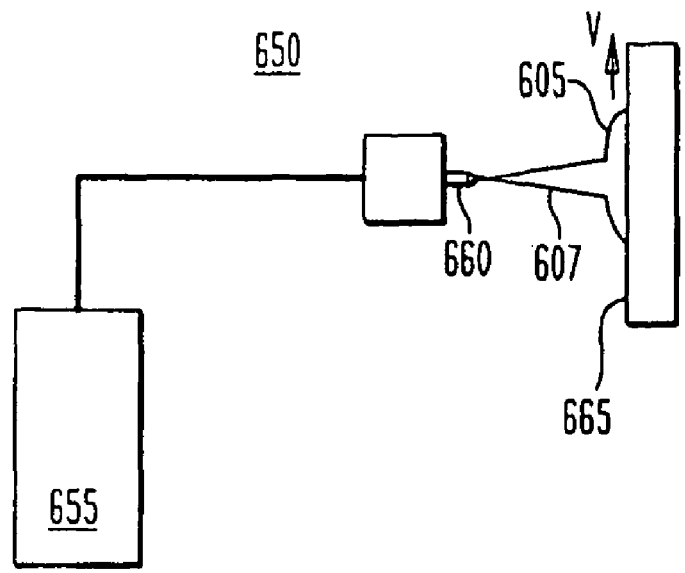
FIG. 6B is a cross-sectional side view of another embodiment of a cooling system utilizing a cooling liquid.

FIG. 6B is a schematic of another embodiment of a cooling system 650 for use in a head utilizing a flowing, cooling liquid 605. In FIG. 6B, a high-pressure liquid is maintained in a container 655 (e.g., tetrafluoroethane under 1 to 5 atmospheres of pressure) and projected through a nozzle 660 onto a cooling surface 665. The projected liquid 607 from nozzle 660 may be in the form of droplets or stream of liquid. In some embodiments, the liquid is projected as a stream to overcome the poor aerodynamic properties (i.e., high drag) of droplets, thus improving the heat removal properties of cooling system 650. As described above, cooling surface 665 may be any material that is a good conductor of heat (e.g., copper or silver). Preferably, cooling surface 665 is selected to have dimensions large enough such that the liquid 655 evaporates from surface 665 rather than drips off said surface.

Projected liquid 607 from nozzle 660 is projected onto cooling surface 665 to form a flowing liquid 605 on cooling surface 665. Nozzle 660 and cooling surface 665 may be selected such that the liquid 607 projected from the nozzle 660 is a stream of liquid the entire distance between the nozzle 660, and upon impinging surface 665 forms a flowing liquid at cooling surface 665. Alternatively, nozzle 660 and cooling surface 665 may be selected such that the liquid 607 projected from nozzle 660 may form a spray of droplets between nozzle 660 and cooling surface 665 before aggregating to form a flowing liquid at cooling surface 665. Because liquid projected from nozzle 660 is under high pressure, the flowing liquid on the cooling surface 665 flows across the cooling surface 665 at a relatively high speed V.

Forming a flowing liquid 605 on cooling surface 665 may be used to provide increased heat removal from surface 665 compared to conventional cooling system in which droplets (i.e., a non-flowing liquid) are formed on cooling surface 665. For example, the improved heat removal may result from the fact that droplets (as formed in a conventional system) are not formed in sufficient number or density to achieve and maintain a selected amount of heat removal.

Figure 6C:
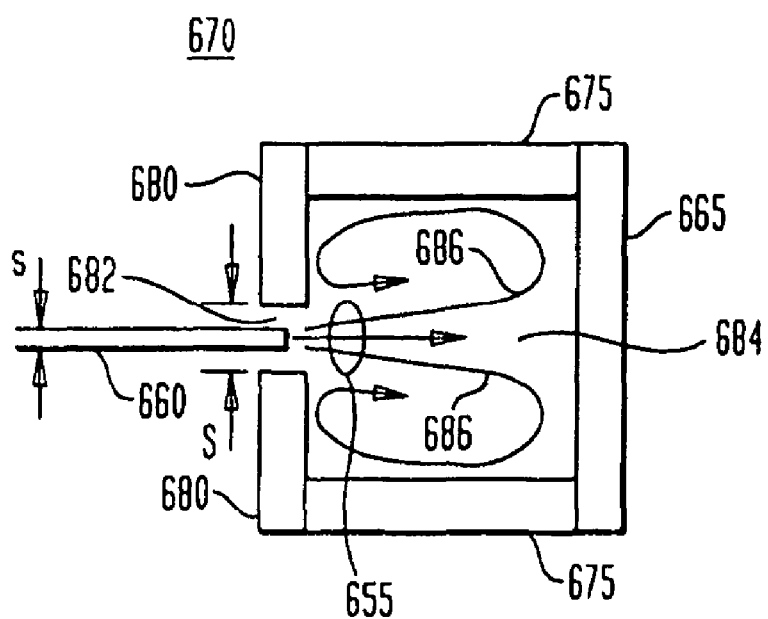
FIG. 6C is a schematic of another embodiment of a cooling system utilizing a cooling liquid and having a cooling chamber.

FIG. 6C is a schematic of another embodiment of a cooling system 670 for use in a head, utilizing a cooling liquid 655 and having a cooling chamber 684. Head 670 has sidewalls 675 and a cover 680 having a port 682 for entry of the liquid 655 from nozzle 660. Sidewall 675 and cover 680 form chamber 684. Port 682 may also serve as an exhaust vent for evaporated cooling liquid. As indicated by arrows 686, sidewalls 675 and cover 680 redirect the liquid 655 from cover 680 back to the cooling surfaces 665. The sidewalls 675 are preferably selected to be thermally coupled to the cooling surface 665 such that liquid contacting the sidewalls 675 may remove heat from the cooling surface 665. Optionally, the side walls 675 may be integrated with cooling surface 665 such that liquid contacting the sidewall 675 may remove heat. In some embodiments, it may be preferable that cover 680 have poor thermal conductivity and poor wetting characteristics for the cooling liquid to improve the likelihood that the cooling liquid will reach the cooling surface 665. For example, in some embodiments, cover 680 is made of a polymer or organic glass. Although chamber 684 is illustrated as having sidewalls and a cover forming an angle therebetween, the chamber may be formed having a continuous curvature.

Because port 682 operates as an exhaust vent from evaporated liquid 655, the area S of port 682 determines the pressure maintained within chamber 684. In some embodiments, port 682 is selected to have a area S large enough to prevent back pressure that slows the speed of the liquid projected on the cooling surface 665; however, port 682 may be selected to be small enough to allow the cover 680 to redirect a significant portion of liquid back to the cooling surface 665, and to maintain pressure in chamber 684 to keep the liquid from evaporating too quickly. For example, port area S may be approximately one hundred to two hundred times as large as the area s of nozzle 660. In some embodiments, the cooling liquid is selected to be a liquid that has an boiling temperature (i.e., evaporation temperature) of less than −26 degrees Celsius for pressures less than or equal to atmospheric pressure.

Figure 6D:
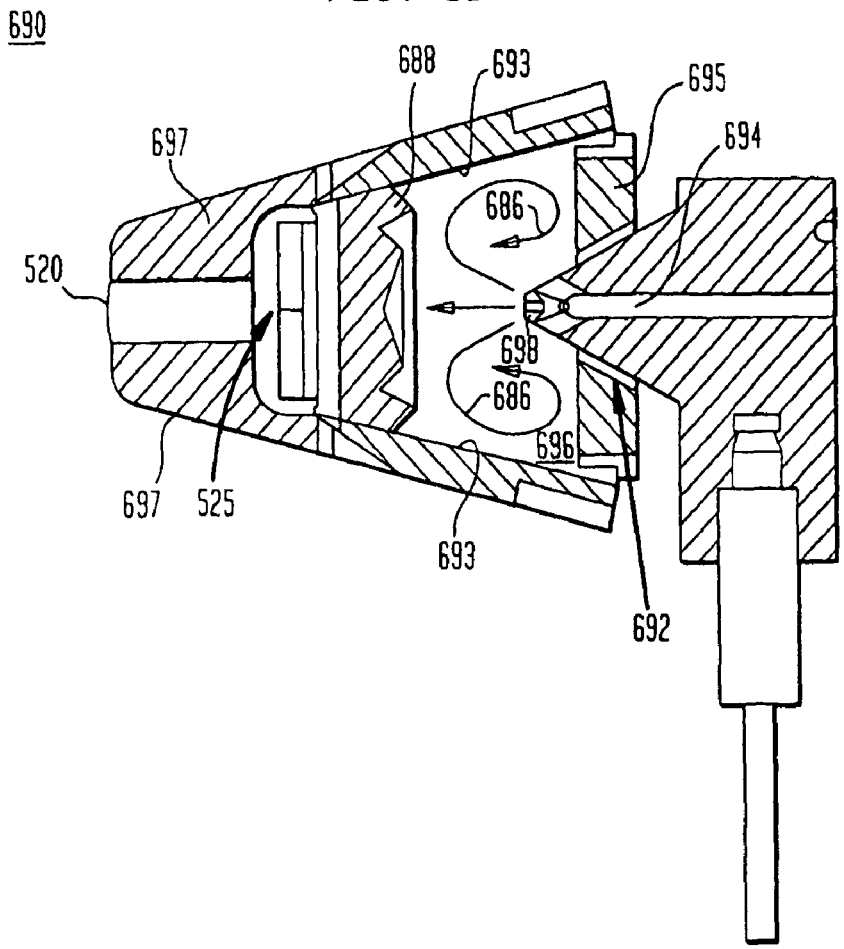
FIG. 6D is a cross-sectional side view of an embodiment a head utilizing a cooling liquid in which the exhaust vent is separated from the port through which cooling liquid enters chamber.

FIG. 6D is a cross-sectional side view of an embodiment a laser head 690 utilizing a cooling liquid in which the exhaust vent 692 is separated from the port 694 through which cooling liquid enters chamber 696. Chamber 696 is bounded by a cooling surface 688, side walls 693, and a cover 695. Cooling surface 688 is thermally coupled to source 525, and optical system 520 via coupling plates (described in greater detail below). A cooling liquid from nozzle 698 is projected onto textured cooling surface 688. A portion of the cooling liquid which does not contact cooling surface 688 directly is redirected by side walls 693 and cover 695 as indicated by arrows 686.

Optionally, cover 695 may be selected to have a resonant frequency to enhance its ability to redirect the liquid to cooling surface 688. Also, optionally a means to reduce the kinetic energy of the liquid (e.g., propeller, not shown) may be placed between the nozzle 698 and the cooling surface 688 to cool the liquid.

Figure 7:
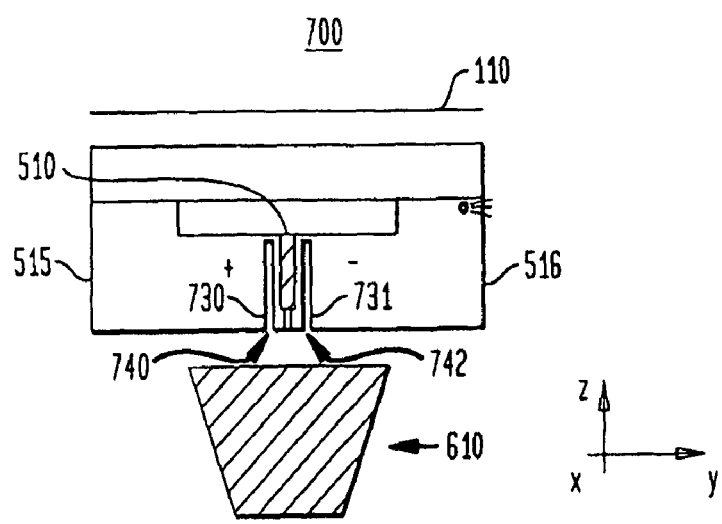
FIG. 7 is a cross-sectional side view of an embodiment of a cooling system having channels.

FIG. 7 is a cross-sectional side view of an embodiment of a head 700 for contacting skin surface 110. Head 700 has channels 730 and 731 in the electrodes 515, 516). Evaporative cooling may occur along the bottom surface of electrodes 515, 516 and along the surface of channels 730, 731, thus increasing the cooling surface area of head 700. Preferably, the location of channels 730 and 731 is proximate diode laser bar 510. In one embodiment, channels 730, 731 are located along the length of the diode laser bar 510 (i.e., along direction-x). In some embodiments, channels 730, 731 are located proximate a spray jet 610 to receive spray. Channels 730 and 731 may have a rectangular cross section or any other shape appropriate to improve cooling. For example, openings 740, 742 may be flared to receive spray from spray jet 610. As an alternative to a single channel extending along the length of the diode bar 510, a series of channels may be placed on one or both sides of diode laser bar 510 along the length of the diode laser bar.

Figure 8:
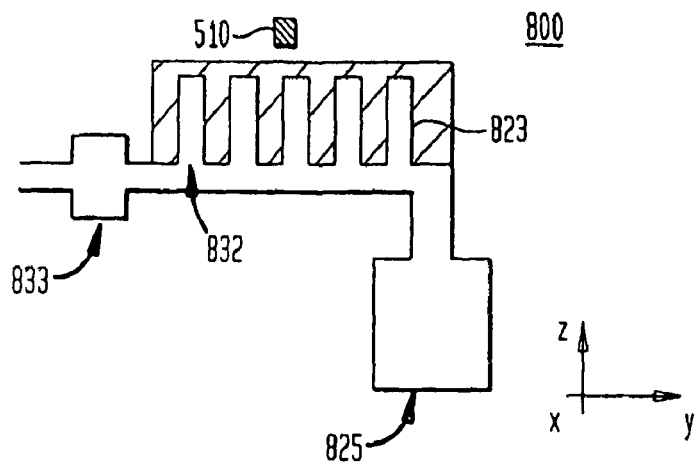
FIG. 8 is a cross-sectional side view of another embodiment of a head utilizing evaporative cooling of a liquid.

FIG. 8 is a cross-sectional side view of another embodiment of a cooling system 800. In FIG. 8, a liquid is used to remove heat from cooling surface 823 but the liquid is not used in spray form. In the illustrated exemplary embodiment, liquid flows out of reservoir 825 into a plurality of channels 832 located within cooling surface 823. The length of each of the plurality of channels 832 extends in the direction of the length of source 510. The liquid is brought into thermal contact or physical contact with cooling surface 823.

Optionally, the liquid may be a low-boiling point liquid that evaporates in response to heat absorbed from cooling surface 823. A valve 833 may be used to control the liquid evaporation; when significant cooling is desired, valve 833 is opened and a pressure less than equilibrium is applied to the liquid to facilitate evaporation. The pressure drop causes the liquid to boil, which removes heat from cooling surface 823. Although channels 832 are illustrated as extending in a direction parallel to the length of light source 510, and the channels are illustrated as having rectangular cross sections, other shape of channels 832 aligned in one or more in various directions are possible and are within the scope of the present aspect of the invention. A feedback signal can be derived from a thermal sensor (e.g., sensor 524 in FIG. 5) to control a solenoid in control valve 833.

Figure 9:
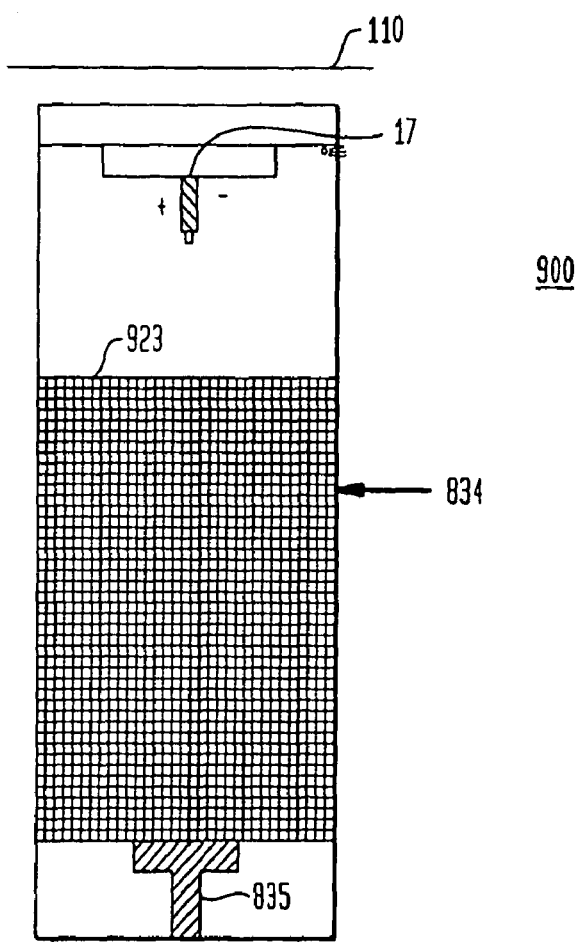
FIG. 9 is a cross-sectional side view of an embodiment of a cooling system using a solid phase-change material according to aspects of the present invention.

FIG. 9 is a cross-sectional side view of another exemplary embodiment of a head 900 for contacting a skin surface 110. Head 900 has a cooling system having a cooling surface 923 that is brought into physical contact with a solid mass (also referred to as a phase change solid). At least a portion of the solid mass 834 changes phase in response to heat absorbed from cooling surface 923. The phase change may be from a solid to liquid, or a solid to a gas. In some embodiments, the solid has a melting temperature between approximately −10 C and +30 C; however, in some applications, materials undergoing a phase change outside this range, particularly below this range, may be utilized.

In some embodiments, the solid mass is conveniently located within a device handpiece (e.g. handpiece 170 in FIG. 1) so as to be user replaceable. In some embodiments, the solid mass is contained in an insulating sleeve to avoid contact with user's hands, and/or to minimize melting do to exposure to room temperature. In the illustrated embodiment, temperature control can be achieved by using a manually or electrically controlled solenoid or a spring 835 to bring the solid mass in and out of contact with cooling surface 923.

In one embodiment of the phase-change cooling system, the phase-change solid is ice. In this embodiment, a user could keep one or more frozen ice blocks in his/her freezer. When the user wanted to operate the photocosmetic device, a frozen ice block could be inserted in the device. In another embodiment, dry ice, which has a significantly lower melting point than water, could also be used to achieve greater cooling capacity. It is to be understood that the ice block may contain water, or water with one or more additives to treat a user's skin.

In some embodiments, commercially available organic compounds (e.g., paraffin wax-based materials, fatty acids, cross-linked polyethylenes) may be used as phase change solids. Examples of appropriate paraffin wax materials include RT25 produced by Rubitherm GmbH. RT25 has a melting point of 27.7° C. In other embodiments, greases having melting points in the 20-35° C. range may be used as the phase change solid. In another embodiment, Ga or a Ga alloy (e.g., Ga/In, Ga/In/Sn, or Ga/In/Sn/Zn), which is tailored to exhibit a melting point in the 15→50° C. range, is used as the solid mass. In a Ga/In alloy, the relatively high thermal conductivity of Ga (40.6 W/m*K) and In (81.6 W/m*K) would help to spread the waste heat throughout the alloy volume. A disposable phase-change cooler cartridge may be used to contain the phase-change solid; for example, the phase change solid may be used either once and then discarded or may be rechargeable (i.e., resolidified one or more times).

Figure 10:
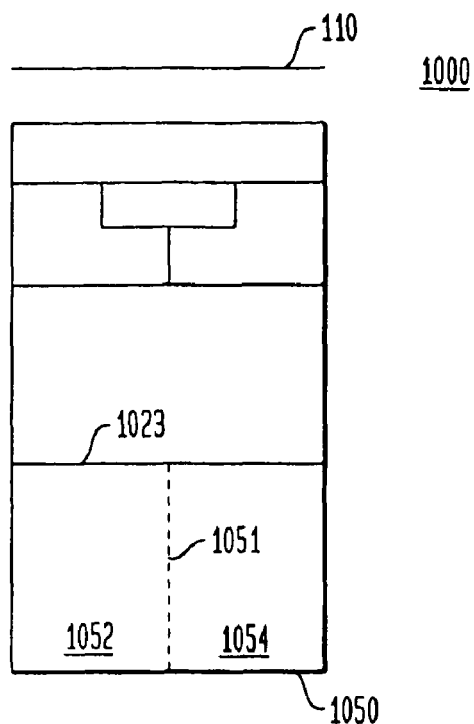
FIG. 10 is a cross-sectional side view of an embodiment of a cooling system using an endothermic chemical reaction for cooling.

FIG. 10 is an embodiment of a head 1000 having a cooling system in which an endothermic chemical reactions is used for cooling. Examples of appropriate reactions are ammonium nitrate ($NH_4NO_3$) or ammonium chloride ($NH_4Cl$) introduced into water causing an endothermic reaction. For example, if 200 ml of water is mixed with 200 g of ammonium nitrate, a temperature of approximately −5° C. can be achieved, thus allowing absorption of a heat.

In FIG. 10, an endothermic reaction is contained within a reaction chamber 1050, and the reaction chamber is thermally coupled to cooling surface 1023. In some embodiments, reaction chamber 1050 could be coupled to the cooling surface 1023 via a material having a good thermal conductivity. In some embodiments, the mechanism includes a thin membrane 1051 separating a first chamber of water and another chamber of ammonium chloride. In some embodiments, membrane 1051 can be broken to initiate the reaction and the reaction chamber could be a disposable container. For example, the user could apply force to a flexible plastic reaction chamber to break a membrane and thereby produce a reservoir of cold liquid prior to turning on the device. Alternatively, the membrane may be removed or otherwise manipulated according to any known means to allow contents of the first chamber and the second chamber to interact.

Figure 11:
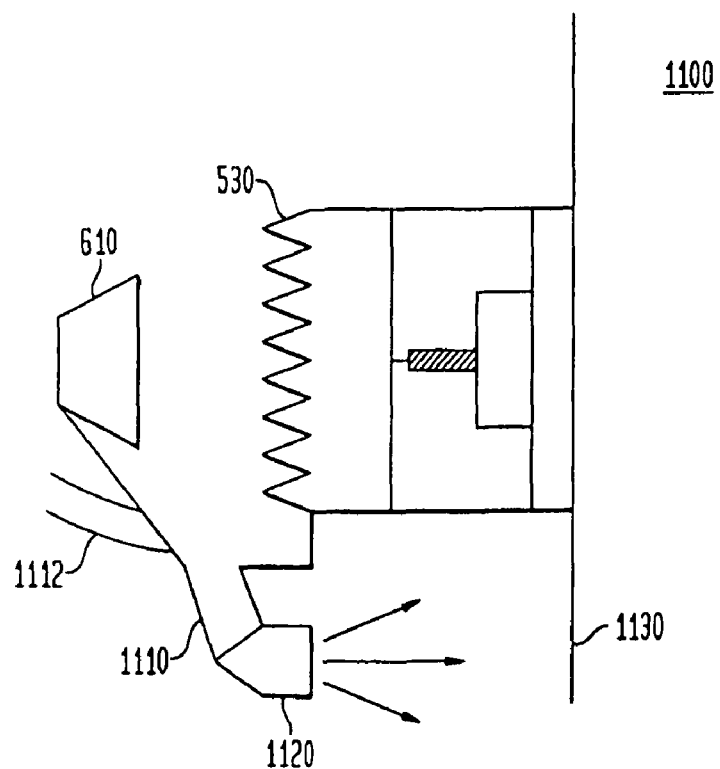
FIG. 11 is a cross-sectional side view of an embodiment of a device having an exhaust vent to cool a patient's skin.

FIG. 11 is a cross-sectional side view of an embodiment of a device 1100 having a conduit 1110 and an exhaust vent 1120. In FIG. 11, a liquid or gas entering exhaust vent 1120 is directed to an area of skin 1130 so as to pre or post cool the area of skin 1130 during treatment. For example, a portion of the same cooling liquid that is sprayed onto cooling surface 530 or the gas resulting from the evaporation of the liquid may enter conduit 1110 and be sprayed onto skin by vent 1120. The portion of liquid may be condensed evaporate or simply excess liquid. If, as described above, tap water was utilized for cooling (or an ice phase-change cooler as described with reference to FIG. 9), it may be possible to divert a portion of the water after the water was used to cool the cooling surface 530. In some embodiments, the pressure from a gas resulting from a phase change cooling system may be used to drive a lotion onto a patient's skin. Although the illustrated embodiment illustrates diverting a portion of the cooling liquid after it is used to cool surface 530, in some embodiments a portion of the cooling liquid may be directly projected onto the skin without being used to cool the cooling surface 530.

Optionally, one or more additives may be added to the liquid via conduit 1112 (e.g., to form a cooling lotion) prior to spraying on the skin. The additives could be stored in a cartridge (not shown) in the handpiece or base unit. In some embodiments, to achieve a "shower effect," all of the water exiting the heatsink could be exhausted onto the skin. As an alternative to using the evaporative liquid, an alternative source of gas, liquid or lotion (i.e., independent of the cooling system) could be stored in a cartridge in the handpiece or the base unit and dispensed while the handpiece is moved across the skin surface.

To avoid obfuscation, the following exemplary embodiments of optical systems for use with aspects of the present invention will be described with reference to a single electromagnetic radiation source; however as described above, one or more sources may be used to form one or more areas of radiation. In the exemplary optical systems described below, each of the surfaces having optical power has optical power along a first axis (e.g., the y-axis) and zero optical power along an axis normal to the first axis (i.e., the x-axis). That is, the lenses are cylindrical. Although the embodiments discussed below have planar or cylindrical curvatures, other refractive or diffractive optical designs are within the scope of the present invention.

Figure 12A:
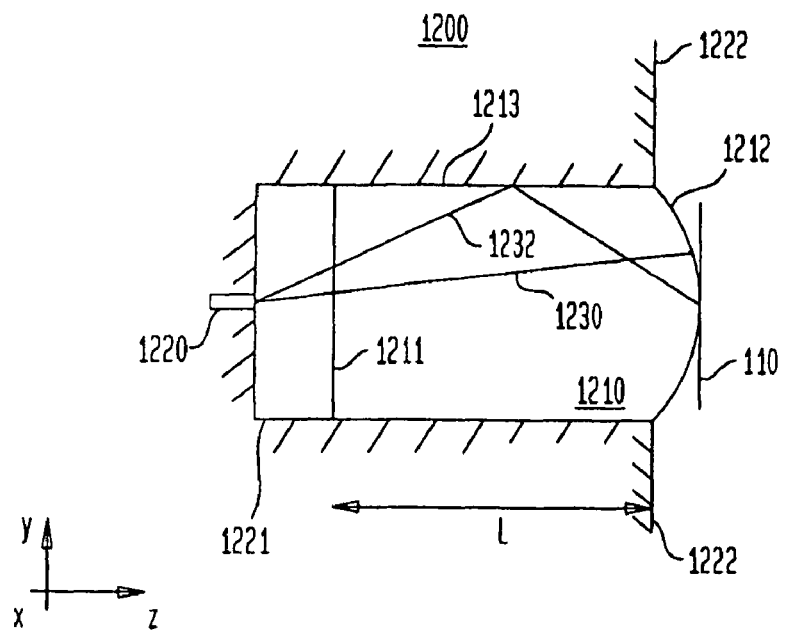
FIG. 12A is a side view of one example of an embodiment of a single-element optical system appropriate for use with photocosmetic devices according to some aspects of the present invention.

FIG. 12A is a side view of one example of an embodiment of a single element optical system 1200 appropriate for use with photocosmetic devices according to some aspects of the present invention. Optical system 1200 includes an element 1210 for transmitting light from an electromagnetic radiation source 1220 (e.g., a laser diode bar) to a patient's skin 110. Element 1210 has an input surface 1211 and an output surface 1212 configured to contact a patient's skin surface.

Source 1220 is closely coupled to input surface 1211 of the element 1210 (e.g., 1 mm separation); close coupling enables a large fraction of light along a highly divergent fast-axis of a laser diode source to be transmitted to a patient's skin. In some embodiments, input surface 1211 has an antireflective (AR) coating.

As described above, element 1210 is made of a material substantially transparent at the operative wavelength, and preferably made of a material that is thermally conductive to remove heat from a treated skin surface (e.g., sapphire). In some embodiments, the lateral sides 1213 of element 1210 are coated with a material reflective at the operative wavelength (e.g., copper, silver or gold). Additionally, the space 1221, between source 1220 and input surface 1211, may be surrounded with a reflective material to increase the strength of light incident on surface 1211.

In one embodiment, optical element 1210 is a sapphire plate (i.e., surfaces 1211 and 1212 are planar, and have no optical power). In another embodiment of optical system 1200, optical surface 1212 has a cylindrical curvature (as shown in FIG. 12) and is selected to converge light incident on surface 1212. For example, in one embodiment, surface 1212 has a radius of curvature of approximately 3 mm. This system can be used to treat skin structures that require high treatment fluence. For example, the lens system of FIG. 13 can be used to target stem cells of hair follicle, sebaceous gland, infrainfundibulum, vascular tissue, tattoos, or collagen.

In some embodiments, lateral surfaces 1213 have a length L approximately in the range 5-50 mm, and a cross-sectional width (measured in the x-direction) and height (measured in the y-direction) are selected to collect light from source 1220. For example, for a source comprised of two 1 cm diode laser bars close-coupled to element 1210, the cross-sectional width is selected to be 2 cm, and the cross-sectional height is 2 cm.

As illustrated, optical element 1210 transmits a portion of light from source 1220 directly to surface 1212 with no reflections on lateral surfaces 1213 (e.g., exemplary ray 1230) and a portion of light from source 1220 is reflected from lateral surfaces 1213 prior to reaching surface 1212 (e.g., exemplary ray 1232). An element, such as element 1210, that directs a portion of light from source to surface using total internal reflection is also referred herein to as a "waveguide."

Optionally, a tip reflector 1222 may be added to redirect light scattered out of the skin back into the skin (referred to as photon recycling). For wavelengths in the near-IR, between 40% and 80% of light incident on the skin surface is scattered out of the skin; as one of ordinary skill would understand the amount of scattering is partially dependant on skin pigmentation. By redirecting light scattered out of the skin back toward the skin using tip reflector 1222, the effective fluence provided by system 1200 can be increased by more than a factor of two. In one embodiment, tip reflectors 1222 extend a total of 3 mm from the upper lateral surface and lower lateral surface of element 1210. In some embodiments, tip reflectors 1222 have a copper, gold or silver coating to reflect light back toward the skin.

A reflective coating may be applied to any non-transmissive surfaces of the device that are exposed to the reflected/scattered light from the skin. As one of ordinary skill in the art would understand, the location and efficacy of these surfaces is dependent on the chosen focusing geometry and placement of the light source(s). Photon recycling is discussed further in U.S. application Ser. No. 09/634,981, filed Aug. 9, 2000, entitled "Heads for Dermatology Treatment," by Altshuler, et al., and application Ser. No. 09/268,433, filed Mar. 12, 1999; the substance of both is hereby incorporated by reference.

Figure 12B:
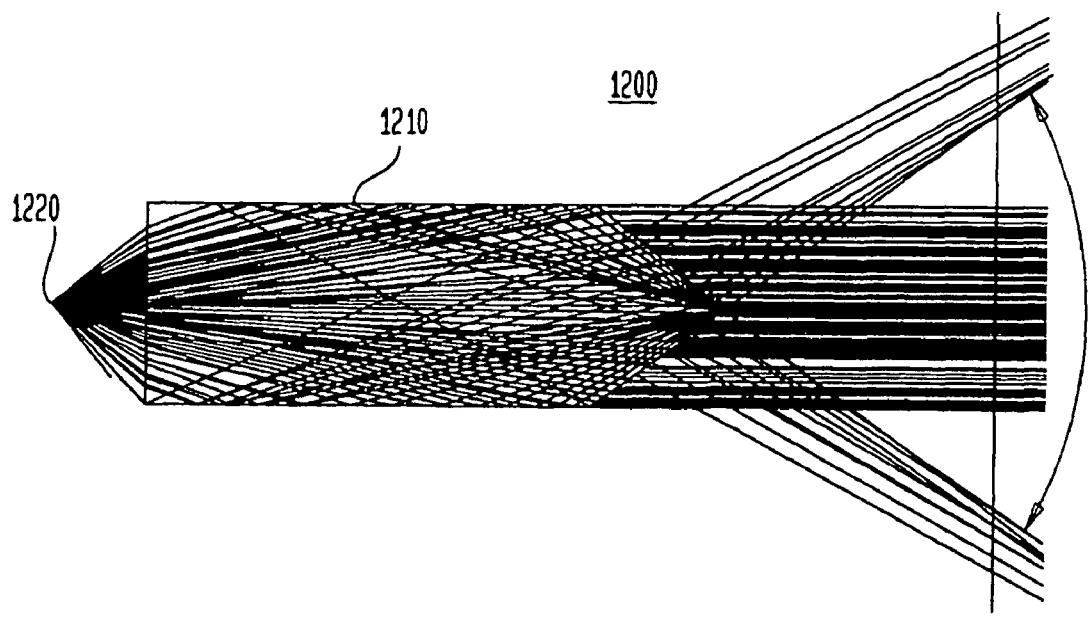
FIG. 12B is a ray trace of one example of an embodiment of an optical system as illustrated in FIG. 12A.

FIG. 12B is a ray trace of one example of an embodiment of such an optical system 1200 having a source 1220 and an element 1210 as illustrated in FIG. 12A.

FIG. 13 is a side view of one example of an embodiment of a two-element cylindrical optical system 1300 appropriate for use with photocosmetic devices according to some aspects of the present invention, in which a collimator 1310 is used in conjunction with element 1210. In FIG. 13, a fast-axis collimator 1310 is very closely coupled to optical source 1220 (e.g., 0.09 mm). In one embodiment, collimator 1310 has a length 1.5 mm, a planar input surface 1311, and an output surface 1312 having a curvature of to collimate the output of collimator 1310. Element 1210 is located 0.1 mm from output surface 1312. Collimator 1310 produces a beam of radiation that is substantially collimated in the y-dimension at output surface 1312. For example, collimator 1310 may be a lens module number S-TIH53 produced by Limo Gmbh of Dortmund, Germany.

Figure 13A:
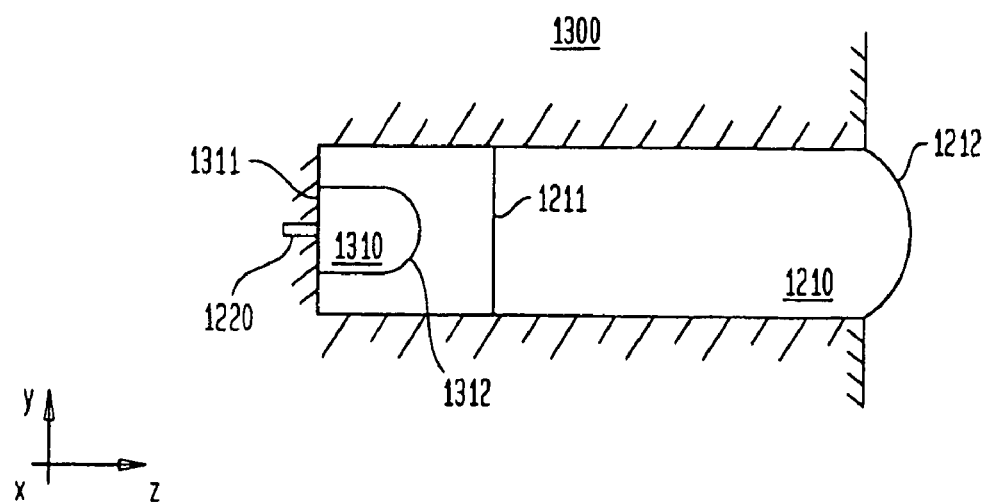
FIG. 13A is a side view of one example of an embodiment of a two-element cylindrical optical system appropriate for use with photocosmetic devices according to some aspects of the present invention.
Figure 13B:
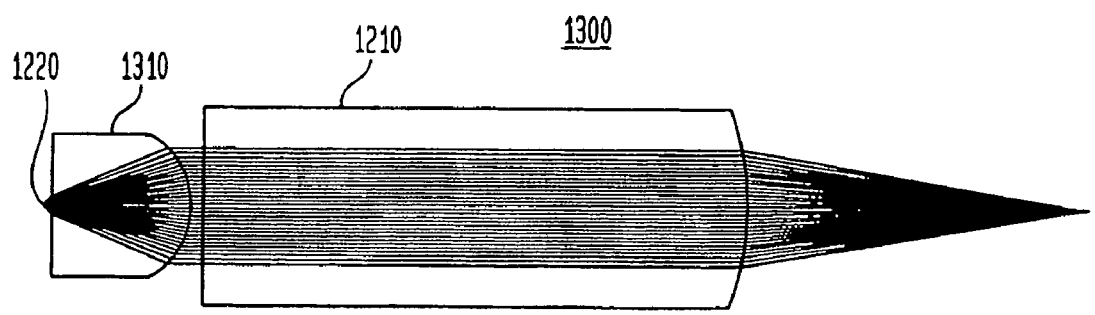
FIG. 13B is a ray trace of one example of an embodiment of an optical system as illustrated in FIG. 13A.

The collimated beam is projected onto input surface 1211 of optical element 1210. As described above, element 1210 may be a plate or may be weakly converging (e.g., output surface 1212 may have a radius of curvature equal to 3 mm) to compensate for scattering in the skin. This system can be used to treat skin structures that require high treatment fluence. For example, the lens system of FIG. 13 can be used to target stem cells of hair follicle, sebaceous gland, infrainfundibulum, vascular, tattoo, or collagen. FIG. 13B is a ray trace of one example of an embodiment of such an optical system 1300 having a source 1220 and a collimator 1310 and an element 1210 as illustrated in FIG. 13A.

Figure 14A:
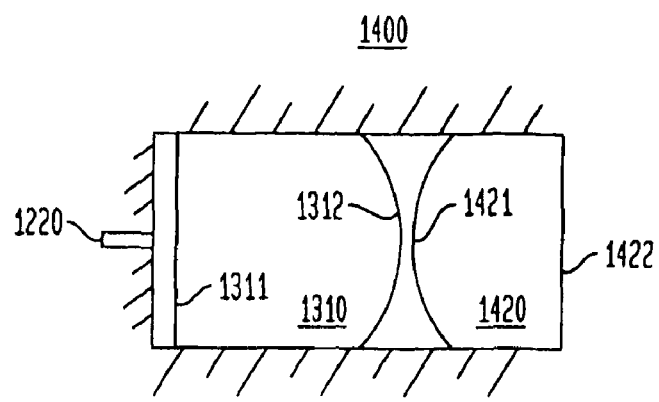
FIG. 14A is a side view of another example of a embodiment of a two-element cylindrical optical system appropriate for use with photocosmetic devices according to some aspects of the present invention.
Figure 14B:
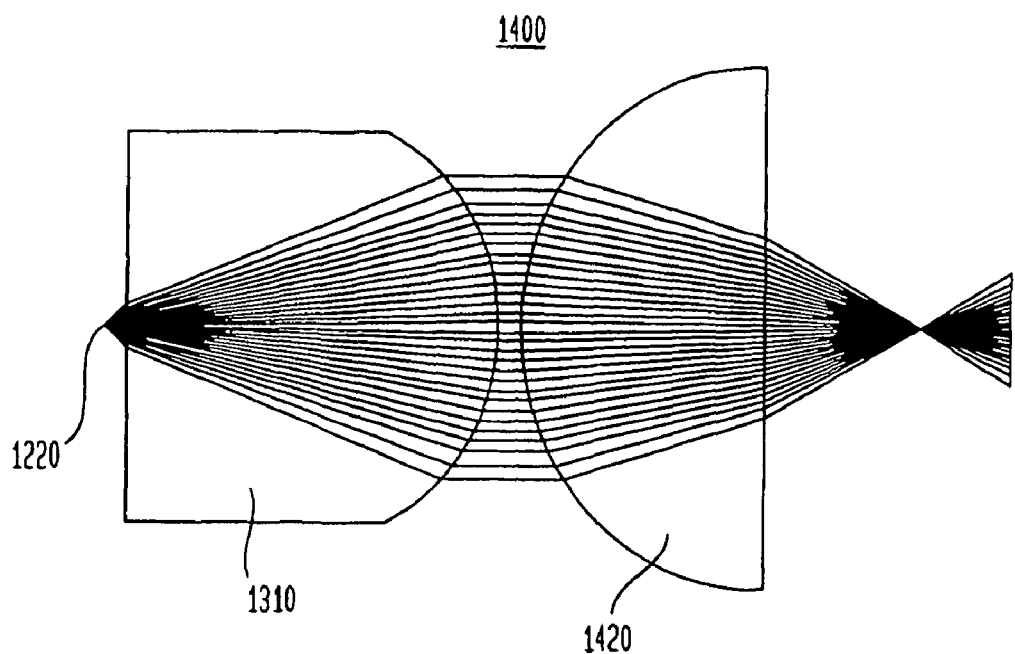
FIG. 14B is a ray trace of one example of an embodiment of an optical system as illustrated in FIG. 14A.

FIG. 14A is a side view of another example of an embodiment of a two-element cylindrical optical system 1400 appropriate for use with photocosmetic devices according to some aspects of the present invention. In optical system 1400, the fast-axis collimator 1310 of FIG. 13 is used in conjunction with an element 1420 located 0.1 mm from surface 1312 of collimator 1310 to project light from source 1220. Element 1420 has an input surface 1421 with a curvature of 1 mm, a planar output surface 1422, and a length of 1 mm. System 1400 focuses light at approximately 1 mm from surface 1422 (i.e., 1 mm below the skin surface for embodiments in which surface 1422 is configured to be in contact with a patient's skin). In one embodiment, the heights of elements 1310 and 1420 are selected to be 1.5 mm. In some embodiments, lens 1420 is made of sapphire. This system can be used to target shallow skin structures that require high treatment fluence. For example, the lens system of FIG. 14 can be used to target psoriasis, sebaceous glands, hair shafts, or hair stem cells. FIG. 14B is a ray trace of one example of an embodiment of such an optical system 1400 having a source 1220 and a collimator 1310 and an element 1420 as illustrated in FIG. 14A.

Figure 15A:
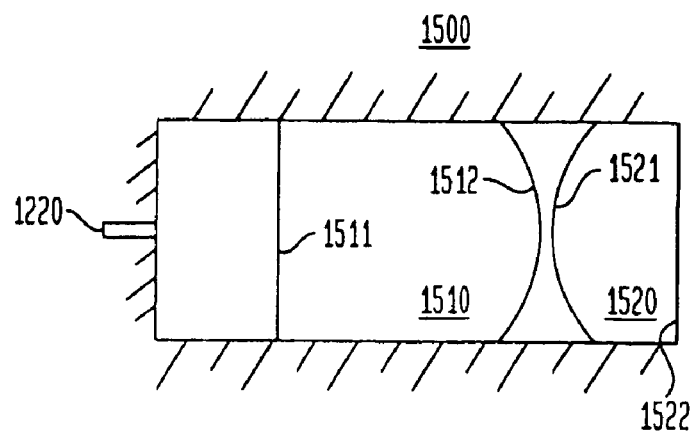
FIG. 15A is a side view of another example of an embodiment of a two-element cylindrical optical system appropriate for use with photocosmetic devices according to some aspects of the present invention.

FIG. 15A is a side view of another example of a embodiment of a two-element cylindrical optical system 1500 appropriate for use with photocosmetic devices according to some aspects of the present invention. FIG. 15 illustrates an optical system 1500 that can be used, for example, to focus the diode light deeper than the optical system 1400 in FIG. 14. For example, optical system 1500 may focus the diode light approximately 2 mm below the skin surface (i.e., 2 mm from surface 1522) to target deep structures (e.g. hair bulb, deeper blood vessels, subcutaneous fat) in the skin.

Figure 15B:
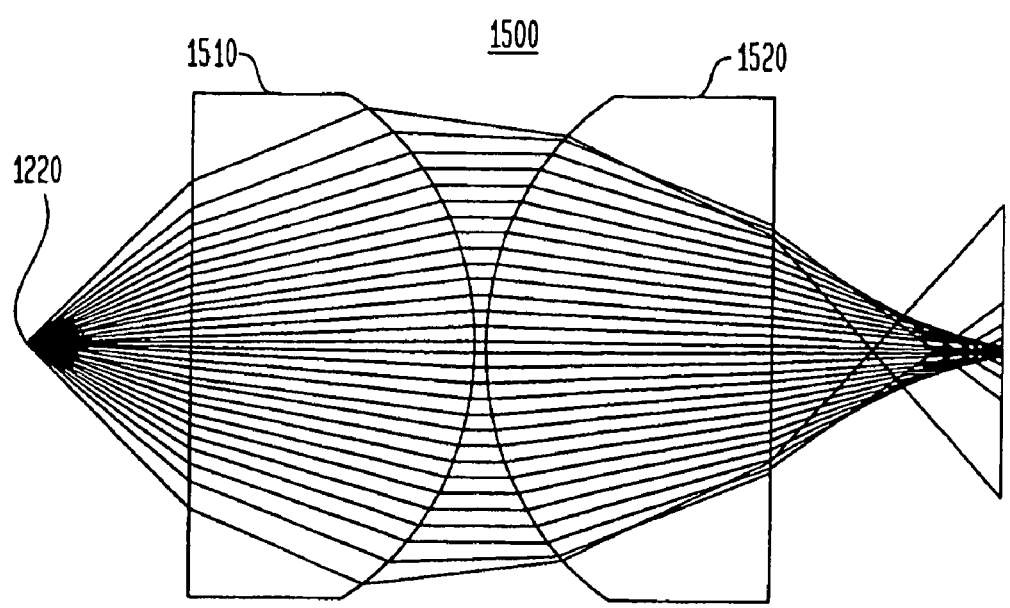
FIG. 15B is a ray trace of one example of an embodiment of an optical system as illustrated in FIG. 15A.

System 1500 is a two-element symmetrical lens system to project light from a source 1220. A first element 1510 is located approximately 1.4 mm from source 1220 and has a input surface 1511 that is planar and an output surface 1512 having curvature of 2.5 mm; accordingly, lens 1510 quasi-collimates the light from light source 1522. A second lens 1520 having an input surface 1521 with a curvature of 2.5 mm and a planar output surface 1522; accordingly lens 1522 focuses the quasi-collimated light 2 mm below the skin surface. In the illustrated embodiment, aberrations in the optical system are balanced to achieve a substantially uniform (i.e., "flat top") spatial optical intensity profile at output surface 1522. The flat top intensity profile is substantially determined by spherical aberration in a plane transverse to the cylindrical surface 1522. In some embodiments, lenses 1510 and 1520 are made of sapphire. FIG. 15B is a ray trace of one example of an embodiment of such an optical system 1500 having a source 1220 and an element 1510 and an element 1520 as illustrated in FIG. 15A.

Figure 16A:
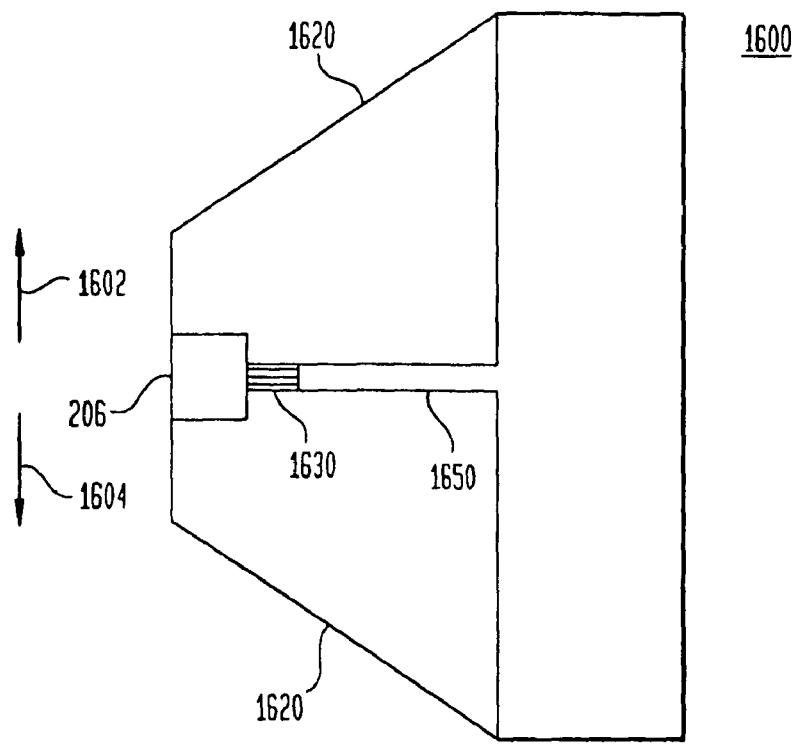
FIG. 16A is a schematic illustration of an exemplary embodiment of a head for performing photocosmetic procedures.

FIG. 16A is a schematic illustration of an exemplary embodiment of a head 1600 for performing photocosmetic procedures. Head 1600 is illustrated without a housing to facilitate description. As described above head 1600 will be moved along an area of a patient's skin, typically in direction 1602 or direction 1604.

Head 1600 includes an optical system 206 to transmit light from an EMR source 1630. Electrodes 1620 activate an EMR source 1630. An electric insulator 1650 may be located between electrodes 1620 to prevent electrical contact between electrodes 1620. Electrodes 1620 may be tapered to reduce the region of contact with a patient's skin.

Figure 16B:
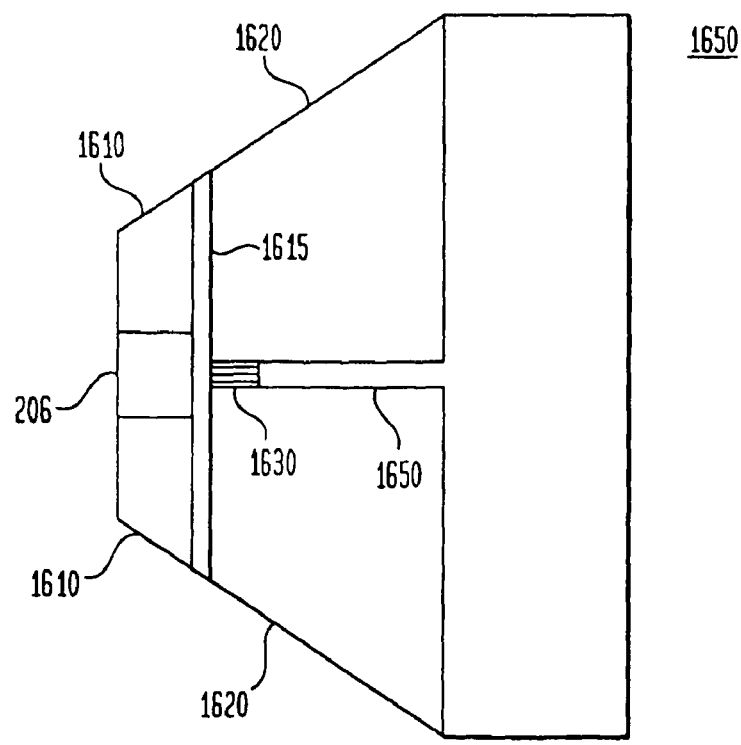
FIG. 16B is a schematic illustration of an exemplary embodiment of a head for performing photocosmetic procedures that also provides the capability to perform muscle stimulation during a photocosmetic procedure.

FIG. 16B is a schematic illustration of an exemplary embodiment of a head 1650 for performing photocosmetic procedures that also provides the capability to perform muscle stimulation during a photocosmetic procedure. Electrical muscle stimulation is a well-known physical therapy procedure that may enhance the efficacy of some photocosmetic procedures. For example, electrical muscle stimulation may be used to improve the efficacy of wrinkle treatment or cellulite treatment.

In one embodiment, two electrodes 1610 for delivering the electrical stimulation are located on opposite sides of optical system 206, on a portion of head 1600 that is designed to be in contact with a patient's skin during a photocosmetic treatment (i.e., during the delivery of EMR by system 206). One electrode 1610 contacts an area of a patient's skin prior to optical system 206 and the other electrode 1610 contacts an area of skin after optical system 206.

A thermally conductive electric insulator 1615 (e.g., made of BeO or diamond or other suitable material) can be used to prevent electrical contact between electrodes 1610 which provide electrical stimulation, and electrodes 1620 which activate EMR source 1630. An electric insulator 1650 may be located between electrodes 1620 to prevent electrical contact between electrodes 1620.

By applying a constant (or pulsed) electrical current to a patient's skin via electrodes 1610 while the handpiece is scanned across the skin surface, simultaneous muscle stimulation and electromagnetic treatment can be achieved. In some embodiments, electrodes may provide radio frequency (RF) current through skin. Alternatively, electrodes, 1610 may provide a DC current or a microwave field. In some embodiments, skin can be scanned with a RF current or microwave field to selectively heat a portion of skin to be treated with EMR radiation. Preheating skin may enable the power of the EMR source 1630 to be decreased.

Figure 17A:
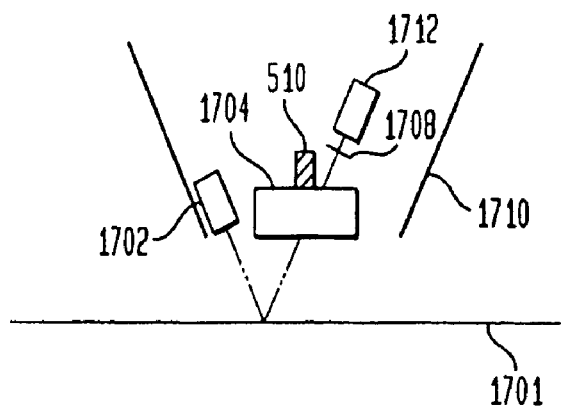
FIG. 17A is a schematic of one example of one embodiment of an apparatus according to some aspects of the invention, which optically determines contact between an optical element and the surface of a patient's skin.

FIG. 17A is a schematic of one example of one embodiment of an apparatus according to some aspects of the invention, which determines contact between an optical element 1704 (e.g., element 1210 of FIG. 12) and the surface of a patient's skin 1701. To provide eye safety, in some embodiments of photocosmetic devices, a contact sensor is used to enable an electromagnetic treatment source (e.g., source 510 of FIG. 5) to activate only when the device is in contact with a patient's skin.

In FIG. 17A, an illumination source 1702 (e.g., diode laser or LED, separate from the treatment source) is mounted a few millimeters (e.g., 5 mm) away from element 1704, and directed toward skin surface 1701. Optionally, illumination source 1702 may be mounted to direct light toward skin surface 1701 through element 1704. Source 1702 may emit radiation at the same wavelength as the treatment source 510 but preferably emits radiation at a different wavelength than the treatment source 510. A detector 1712 is located to detect light from the illumination source that is reflected or scattered from the surface of skin 1701. Optionally, a filter 1708 may be added to selectively transmit light from source 1702, and to eliminate wavelengths of light corresponding to the treatment source 510 and any other extraneous wavelengths of light.

Figure 17B:
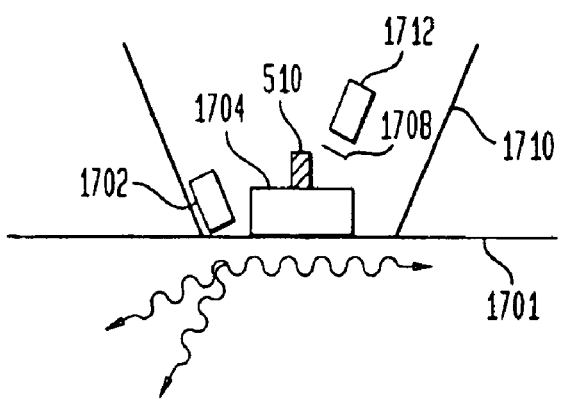
FIG. 17B is a schematic of one example of one embodiment of an apparatus according to some aspects of the invention, which optically determines contact between an optical element and the surface of a patient's skin.

In the case of poor or no skin contact, a relatively large amount of radiation light from source 1702 would reflect or scatter from the skin surface 1701 through the optical system 1704 to detector 1712. As illustrated in FIG. 17B, when element 1740 is in good contact with the skin surface 1701, scattering and absorption in the skin would attenuate light from the illumination source 1702, and a relatively small amount of radiation would reach detector 1712. Thus, by using an electronic means (e.g., a comparator) to measure the output of detector 1712, and selecting an appropriate threshold, the treatment source can be configured to activate only when the output of detector 1712 is below the threshold. Optionally, source 1702 and/or detector 1712 may be located in a base unit and one or more optical fibers may be used to couple light from the handpiece to the source or detector.

In another embodiment, detector 1712 detects light from the treatment source to determine contact between element 1740 and skin surface 1701. In such a system, light from source 510 is scattered and reflected by skin surface 1701 through element 1704 to detector 1712. A radiation filter 1708 may selectively transmit this scattered and reflected radiation to detector 1712. In this embodiment, the treatment source 510 is maintained at a low-power eye-safe mode until firm contact with the skin surface 1701 is made. When there is no or poor contact between skin surface 1701 and element 1704, the output of detector 1712 is relatively low. However, when element 1704 is in good contact with the skin surface 1701, the output of detector 1701 is relatively high. Thus, treatment source 510 would be configured to fire only when the output of detector 1712 was above a threshold level.

Alternatively, instead of source 1702 and detector 1712, a standard optical contact detector that is in an optical computer system mouse can be used, for example, the optical contact system in a CordLess Mouseman™ produced by Logitech of Fremont, Calif.

Figure 17C:
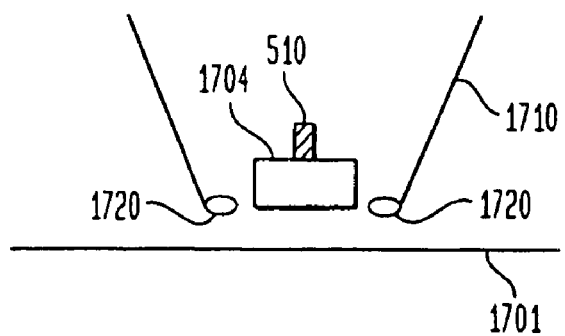
FIG. 17C is a schematic of one example of one embodiment of an apparatus according to some aspects of the invention, which electrically determines contact between an optical element and the surface of a patient's skin.

As an alternative to the optical methods of determining contact, electrical methods can be used to detect contact between element 1704 and a patient's skin 1701. FIG. 17C is a cross-sectional view of handpiece having two electrical contacts located in a portion of the handpiece such that when element 1704 is in contact with skin 1701, contacts 1720 are also in contact with skin 1701. Contact can be determined by measuring resistance (or capacitance) between the contacts. Treatment source 510 would be activated when resistance (or capacitance) between contacts 1720 was within a selected range (i.e., a range typical for skin). In another embodiment, contacts 1720 may be magnetic sensors to detect contact with skin surface 1701. In another alternative embodiment, contacts may be mechanical sensors to detect contact with skin surface 1701. For example, one or more spring-loaded pins or buttons may be located such that when the element 1704 is in contact with the skin the pin or button is depressed. Multiple sensors, pins, buttons, or other mechanical sensors located around the perimeter of element 1704 could be used to help ensure that the entire surface of element 1704 face was in good contact with skin. Alternatively, contacts 1720 can be conventional load cells to determine contact with skin surface 1701. Contacts, sensors, pins, buttons, or other mechanical sensors that allow for the measurement of resistance or capacitance may be preferred to ensure that the contact is with skin and not with another surface, for example, a mirror or countertop.

In another embodiment, one or more temperature sensors are used to determine contact with skin surface 1701. A typical skin surface temperature is in the 30-32° C. range; accordingly temperature sensors could be located near a surface of the device which contacts a patient's skin, and contact could be determined to occur when the measured temperatures were within a selected range (e.g., 23-27° C.). Alternatively, contact could be determined to have occurred when the temperature sensors measured a temperature versus time slope indicative of contact. In still another embodiment, where lotion is to be dispensed on the skin (described above with reference to FIG. 11), skin contact could be detected by using a pressure sensor within spray jet 1120. The pressure sensor would measure the pressure needed to eject the lotion onto the skin. Only when the handpiece was in good contact with the skin would relatively high pressure be provided to dispense the lotion.

Contact sensor designs are described in greater detail in U.S. application Ser. No. 09/847,043, by Henry Zenzie, filed Apr. 30, 2001, entitled "Contact Detecting Method and Apparatus for an Optical Radiation Handpiece," the substance of which is hereby incorporated by reference.

A handpiece is preferably scanned across a patient's skin within a specified speed range. If the handpiece is moved too slowly (typical minimum speed limit would be between 5 and 25 mm/s depending on the application), the light dosage will be too high and undesired thermal damage may result. Correspondingly, if the handpiece is moved too quickly (typically the maximum speed limit would be between 50 and 500 mm/s depending on the application), the light dosage will be too low to achieve treatment efficacy. Thus, only when the handpiece is scanned within this speed range does the handpiece emit electromagnetic radiation for treatment. An exemplary speed range for operation of a photocosmetic hand piece for hair removal/growth delay is 10-500 mm/s which corresponds to the speed ranges with which is approximately equal to the speed which a typical razors passes over their skin.

Figure 18A:
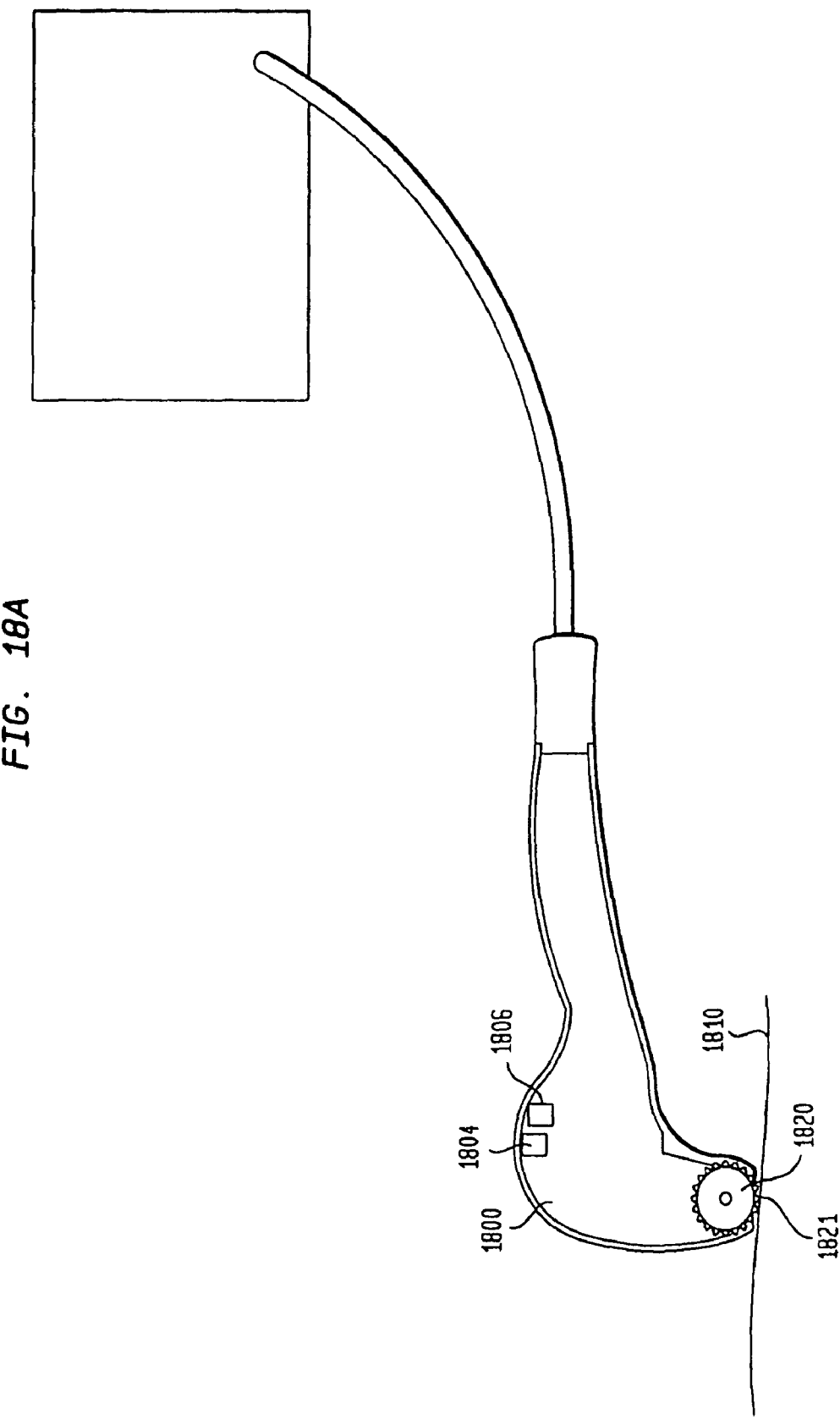
FIG. 18A is a cutaway side view of one embodiment of a handpiece having a motion sensor.

FIG. 18A is a cutaway side view of one embodiment of a handpiece 1800 having a motion sensor 1820 for determining handpiece speed. Motion sensor 1820 may be used to prevent injury to skin 1810 by providing feedback control to a treatment source (e.g., source 510 in FIG. 2), such that if the handpiece remains motionless or if the movement across the skin 1810 is too slow or too fast, the intensity of source may be decreased or increased, respectively, or the source may be turned off. Optionally, the treatment source may be disabled instead of reduced in power. In one embodiment, a wheel 1821 is positioned to make physical contact with skin 1810, such that the wheel rotates as handpiece 1800 is moved relative the skin 1810, and handpiece speed can be determined.

Handpiece 1800 may be configured to inform the operator when the handpiece speed is inside or outside of an acceptable speed range. For example, a tactile indicator (e.g., a vibrator) could be configured to vibrate the handpiece when the handpiece speed is inside or outside the desired range. Alternatively, a visual indicator 1804 (e.g., an LED) or an audio indicator (e.g., a beeper) may be used to inform the operator that the handpiece speed is inside or outside the desired range. In some embodiments, multiple indicators 1806 (e.g., LEDs having different colors, or different sound indicators) may be used to inform the operator that the handpiece speed is either too high or too low or is within the desired range.

Figure 18B:
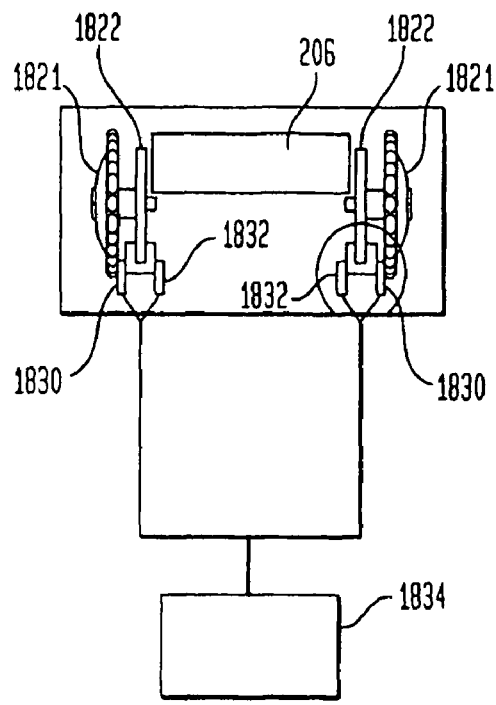
FIG. 18B is a schematic of one example of an embodiment of a motion sensor system.

FIG. 18B is a schematic of one example of an embodiment of a motion sensor system having at least one wheel 1821. Preferably a second wheel 1821 is added and located on an opposite side of optical system 206 to ensure that the entire skin contacting surface of the optical system 206 moves at a rate of speed within the acceptable range to provide uniform illumination on a patient's skin.

In one embodiment, each external wheel 1821 is coupled to a corresponding auxiliary internal wheel 1822 having perforations around its perimeter. A source 1830 projects light in the direction of a corresponding detector 1832 so that as a wheel 1821 rotates, the perforations of auxiliary wheel 1822 alternately transmit and block light projected by source 1830; as a result, as handpiece 1800 (visible in FIG. 18A) moves across a patient's skin, detectors 1832 produce a signal having a chain of pulses.

One of ordinary skill would understand that the speed of the handpiece across a patient's skin is proportional to the rate at which the pulses occur. A controller 1834 correlates the pulse rate to the handpiece speed. The above-described perforated auxiliary wheel design is similar to a standard computer system mouse design, for example, a mouse wheel in the 3 Bth Wheel Mouse produced by Logitec Corporation of Fremont, Calif., which is just one example of an apparatus to measure handpiece speed, many other apparatus are possible and are within the scope of this aspect of the invention. For example, in an alternative embodiment, a simple electric motor is coupled to wheel 1821 to generate a voltage that is proportional to handpiece speed.

Figure 19:
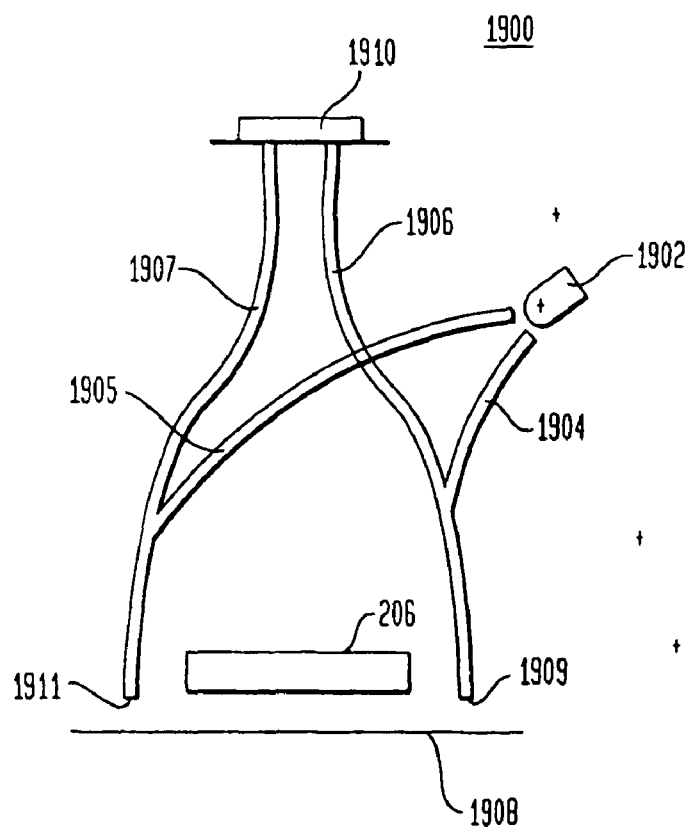
FIG. 19 is a schematic of another example of an apparatus having an optical motion sensor.

FIG. 19 illustrates another optical apparatus 1900 having a motion sensor for determining handpiece speed. In apparatus 1900, a light source 1902 (e.g. an infrared LED) is coupled into the transmitting fiber 1904. A light detector 1910 (e.g., an inexpensive CCD camera or a diode sensor) is coupled to the end of a receiving fiber 1906. In apparatus 1900, the ends of the transmitting fiber 1904 and receiving fiber 1906 are coupled together to form a single fiber end 1909 that is in contact with the skin 1908. A portion of light projected onto skin surface 1908 by transmitting fiber 1904 through fiber end 1908 is reflected or scattered from the skin surface 1908 and received by receiving fiber 1906 through fiber end 1909 and detected by detector 1910. Because the skin surface 1908 has a semi-periodic structure (e.g., the distances between similar tissues such as hair follicle, vessels, glands are almost constant structure) detector output is modulated at a rate dependent on the handpiece speed. One of ordinary skill would understand that handpiece speed can be calculated from the modulated detector output. Optionally, a second transmitting fiber 1905 and receiving fiber 1907 coupled together through fiber end 1911 may be added, so that the first and second transmitting fiber/receiving fiber pairs are located on opposite sides of optical system 206 to ensure that the entire skin-contacting surface of optical system 206 moves across the skin with in the acceptable range to provide uniform illumination on a patient's skin.

In system 1900, each transmitting fibers 1904, 1905 is coupled to a corresponding receiving fiber 1906, 1907; alternatively, a transmitting fiber and corresponding receiving fiber, may contact the skin at distinct, separated points (i.e., the transmitting fiber and corresponding receiving fiber are not coupled at the skin); in such an embodiment, the ends of the fibers contacting the skin may be separated by any distance at which photons scattered by tissue layers can be reliably detected. In such embodiments, the upper bound on the fiber spacing occurs when the light coupled into receiving fiber is reduced to a point at which the amount of scattered photons generates a signal that is too small to be accurately detected.

Although optical apparatus for measuring handpiece speed have been described, it should be understood that other methods of speed measurement are with the scope of this aspect of the invention. For example, electromagnetic apparatuses that measure handpiece speed by recording the time dependence of electrical (capacitance and resistance)/magnetic properties of the skin as the handpiece is moved relative the skin. Alternatively, the frequency spectrum or amplitude of sound emitted while an object is dragged across the skin surface can be measured and the resulting information used to calculate speed because the acoustic spectrum is dependent on speed. Another alternative is to use thermal sensors to measure handpiece speed, by using two sensors separated by a distance along the direction in which the handpiece is moved along the skin (e.g., one before the optical system and one after). In such embodiments, a first sensor monitors the temperature of untreated skin, which is independent of handpiece speed, and a second sensor monitors the post-irradiation skin temperature; the slower the handpiece speed, the higher the fluence delivered to a given area of the skin, which results in a higher skin temperature measured by the second detector. Therefore, the speed can be calculated based on the temperature difference between the two sensors.

An alternative system to measure handpiece speed using thermal characteristics uses a heat source (e.g. the treatment source or another means of heating an area of skin) located a selected distance from a thermal sensor along the direction in which the handpiece is moved along the skin. In such embodiments, the handpiece speed can be determined from the temperature measured by the thermal sensor. For a low handpiece speed, the heat would have sufficient time to propagate through the skin from the heat source to the thermal sensor; however, at high speed the heat would not have time to reach the thermal sensor. Thus, a high skin temperature measured by the thermal sensor would indicate low speed whereas a low skin temperature would indicate high speed.

In an alternative embodiment of a speed sensor, an optical apparatus is used to measure handpiece speed using Doppler-shift techniques. In such a system, the wavelength of light from a probe laser is projected onto the skin and the speed is determined by shifted frequency of a reflected portion of the light.

In any of the above embodiments, a speed sensor may be used in conjunction with a contact sensor (e.g., a contact sensor as described above with reference to FIGS. 17A-17C). In one embodiment of a handpiece, both contact and speed are determined by the same component. For example, an optical-mouse-type sensor such as is used on a conventional computer optical mouse may be used to determine both contact and speed. In such a system, a CCD (or CMOS) array sensor is used to continuously image the skin surface. By tracking the speed of a particular set of skin features as described above, the handpiece speed can be measured and because the strength of the optical signal received by the array sensor increases upon contact with the skin, contact can be determined by monitoring signal strength. Additionally, an optical sensor such as a CCD or CMOS device may be used to detect and measure skin pigmentation level or skin type based on the light that is reflected back from the skin; a treatment may be varied according to pigmentation level or skin type.

In some embodiments of the present invention, a motion sensor is used in conjunction with a feedback loop or look-up table to control the radiation source output. For example, the emitted laser power can be increased in proportion to the handpiece speed according to a lookup table. In this way, a fixed skin temperature can be maintained at a selected depth (i.e., by maintaining a constant flux at the skin surface) despite the fact that a handpiece is moved at a range of handpiece speeds. The power used to achieve a given skin temperature at a specified depth is described in greater detail in U.S. patent application Ser. No. 09/634,981, which was incorporated by reference herein above. Alternatively, the post-treatment skin temperature may be monitored, and a feedback loop used to maintain substantially constant fluence at the skin surface by varying the laser output power. Skin temperature can be monitored by using either conventional thermal sensors or a non-contact mid-infrared optical sensor. The above motion sensors are exemplary; motion sensing can be achieved by other means such as sound (e.g., using Doppler information).

Although the above embodiments were discussed with reference to a system monitoring handpiece speed as moved by an operator, the handpiece could be mounted on a translation stage to move the handpiece at controlled, predetermined speed across the skin surface. In such an embodiment, the apparatus would be positioned relative the patient to treat a selected area of skin, and the translation stage could be moved to a subsequent area as necessary.

Figure 20:
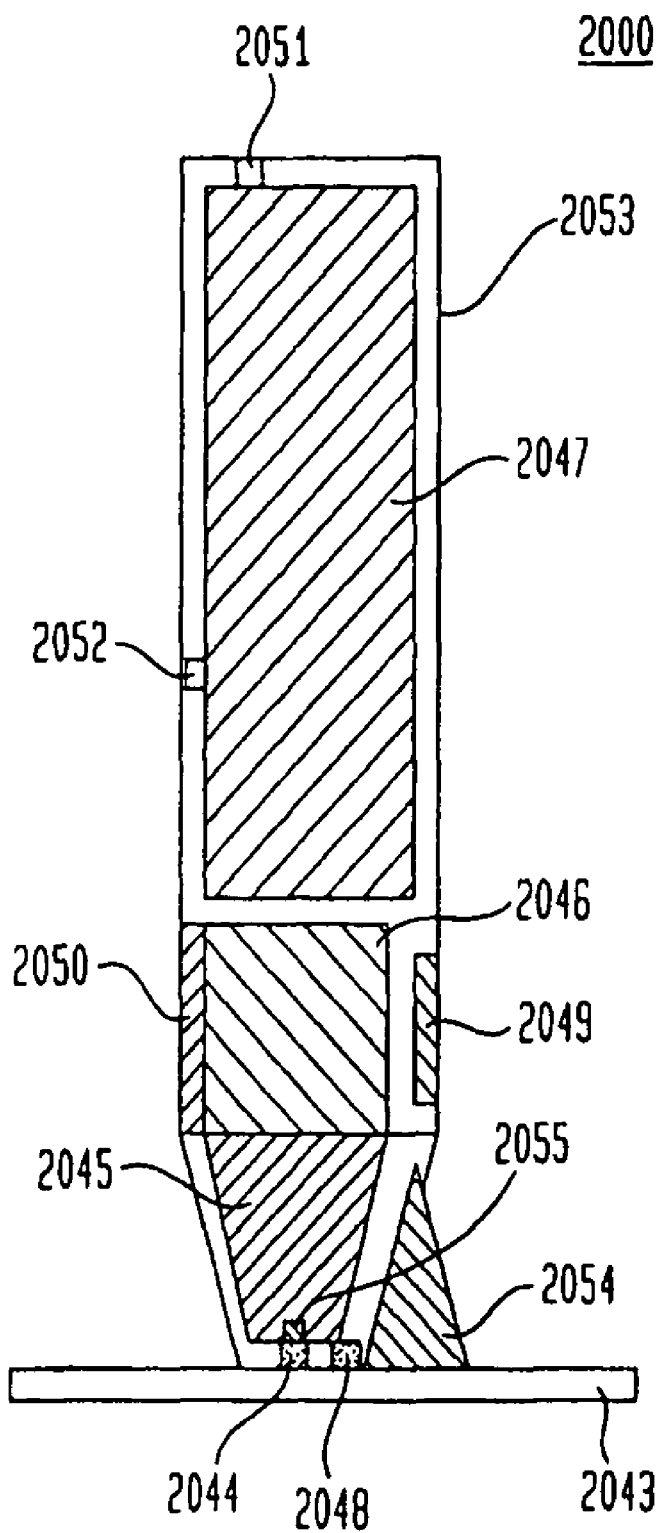
FIG. 20 is a schematic of one example of one embodiment of a handpiece illustrating some aspects of a self-contained photocosmetic device according to the present invention.

FIG. 20 is a schematic of one example of one embodiment of a handpiece 2000 illustrating some aspects of a self-contained photocosmetic device. Handpiece 2000 includes an optical source 2055, a power supply 2047, an optical system 2044, a cooling system 2046, and a speed and/or contact sensor 2048. The device is shown in contact with an area of skin 2043. Optical system 2044 couples light from light source 2055 into the skin treatment area 2043.

Cooling system 2046 can be a phase-change cooler or any other appropriate cooling system. In some embodiments cooling system 2046 is in good thermal contact with the heatsink 2045 (or electrodes or other cooling surface, not shown). A power supply 2047 (e.g., battery or capacitor) supplies electrical current to optical source 2055. Contact and/or speed sensor 2048 ensures safe and effective treatment as described herein above. Although a contact and speed sensor is illustrated as a single component, it should be understood the contact and speed sensor may be different components and there may be multiple of each type of sensor as described above. Control electronics 2049 process data from contact/speed sensors 2048 or other sensors (e.g., thermal sensors) and control optical source 2055 and cooling system 2046. Cooling system 2046 may be cooled prior to treatment via a thermal-contact plate 2050. Power source 2047 may be charged via electrical contact 2051. On/off button 2052 controls the electrical power. A housing 2053 may be used to enclose, protect, or mount one or more of the above parts.

Optionally, a hair removal device 2054 may be located to remove hair prior to irradiation by light from optical source 2055 to ensure that substantially no hair extends above the skin surface. For example, hair removal device 2054 may be a blade razor (e.g., a safety razor, a cartridge razor), an electric razor, a stripping device wherein the hair adheres to a surface and is pulled out as the handpiece is moved across a user's skin (e.g., a device like the Epilady™ produced by Happy Lady, Inc.), an abrasive device that grinds the hair, or a chemical compound that dissolves the hair. A hair removal device may be made disposable such that the hair removal device is easily replaceable by a user. In the instance of coarse hair, a razor having one or a plurality of blades may be used; however in the instance of fine hair, an abrasive paper may be used. A body location having coarse hair initially may have fine hair after one or more photocosmetic treatments; accordingly, a blade razor may be used for the first few treatments and an abrasive paper may be used for subsequent treatments. In some embodiments, the abrasive paper may be simply moved across the skin with a stroke of the photocosmetic device, and in other embodiments the paper may be vibrated by a vibrating mechanism (e.g., a motor).

Figure 21:
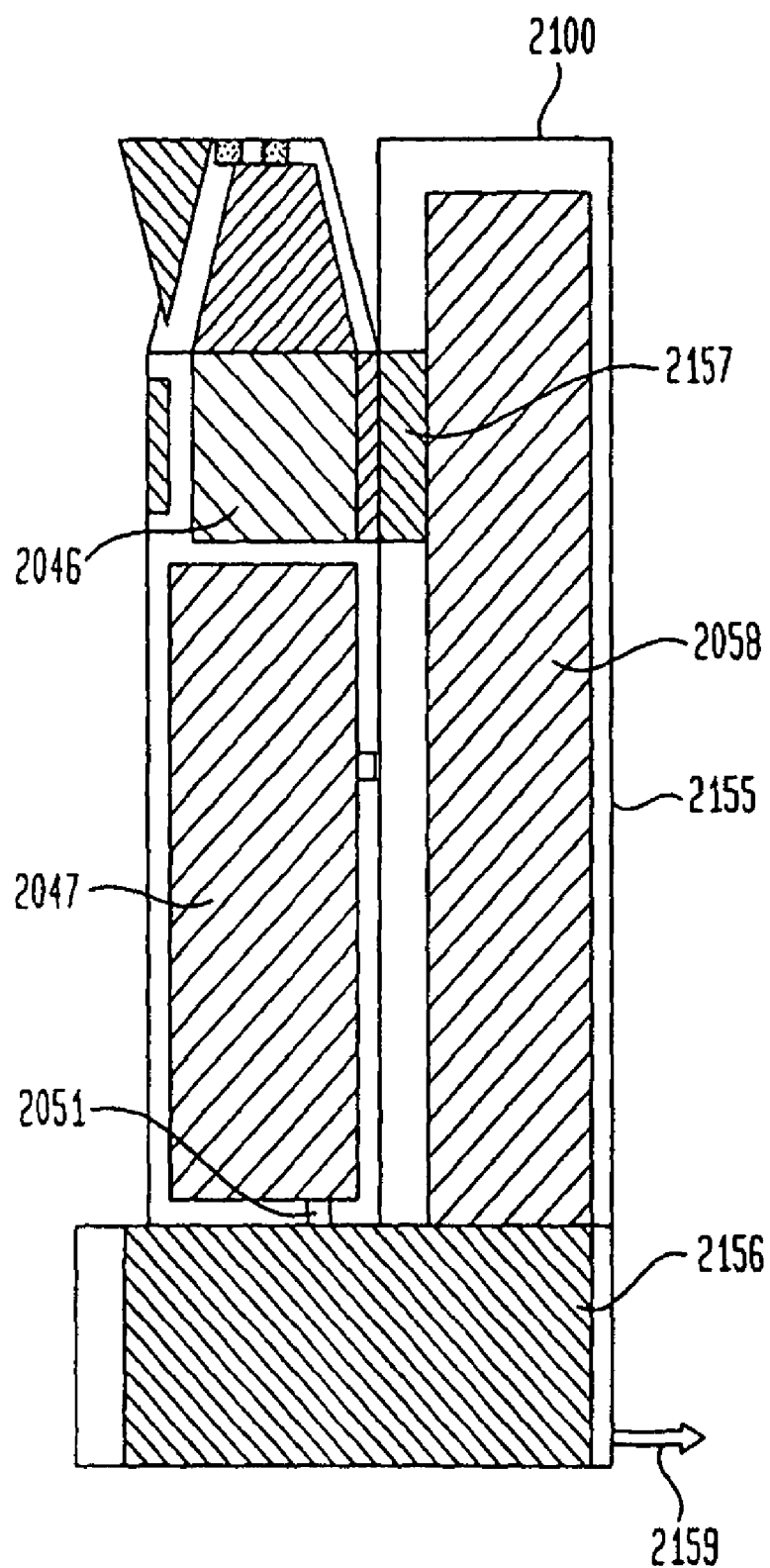
FIG. 21 is a schematic of one example of an embodiment of a handpiece docking station for docking a self-contained photocosmetic device.

FIG. 21 is a schematic of one example of an embodiment of a handpiece docking station 2100 for docking a handpiece 2000. Docking station 2100 is contained in housing 2155. Power supply 2156 charges battery/capacitor 2047 via electrical contact 2051. Cooling material 2046 is cooled by chiller 2157 (e.g., a Peltier element). For example, chiller 2157 may be used to recharge a cooling system, by condensing a phase change liquid or freezing a phase change solid. Heatsink 2058 dissipates heat produced by chiller 2157. Heatsink 2058 may utilize gas, liquid, or solid (phase change) media for heat removal or may simply be fins that are cooled by exposure to room temperature. Umbilical 2159 contains wires to supply electrical power to the docking station from an electrical outlet and may further include tubing for water cooling of heatsink 2058. A self-contained photocosmetic device, and a handpiece docking station are described in greater detail in U.S. Application No. 60/292827, filed Dec. 28, 2000, by G. Altshuler et al., entitled "Method and Apparatus for EMR Treatment," the substance of which is hereby incorporated by reference.

For some embodiments of a photocosmetic device, it is advantageous to have one or more replaceable components. For example, in some embodiments, where the handpiece will likely be dropped or otherwise abused, it may be advantageous to make one or more optical systems removable from the handpiece. In addition, to achieve a variety of treatments that each require different optical sources or optical systems (e.g., treatment of pigmented lesion removal and treatment to achieve hair removal), interchangeable optical components would permit the user to perform different applications with the same handpiece. Additionally, for systems employing light sources or power sources having a limited lifetime, replacement of the light sources at the end of useful life may be desirable.

Figure 22:
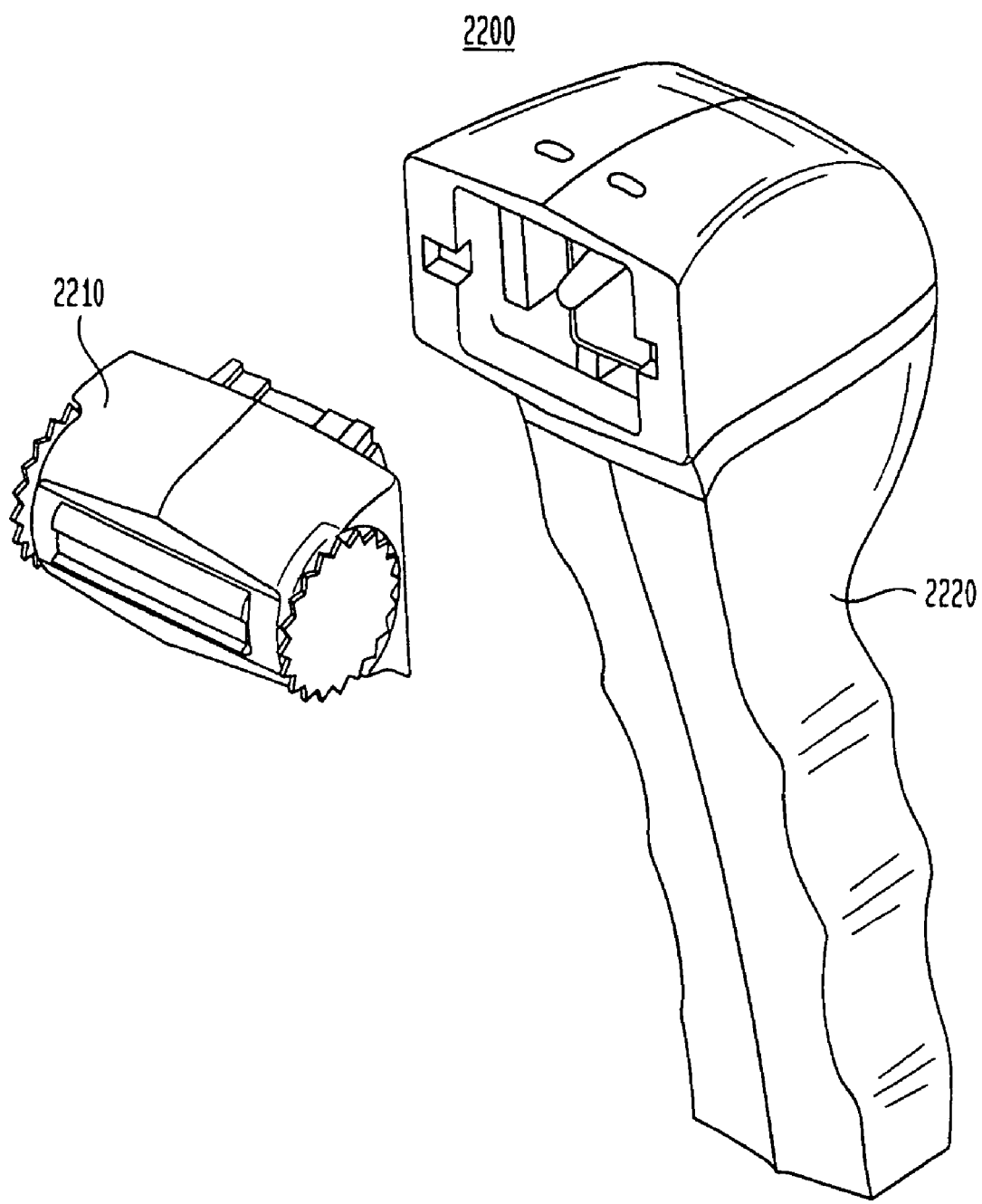
FIG. 22 is a schematic of one example of one embodiment of a handpiece having a detachable head.

FIG. 22 is a schematic of one example of one embodiment of a handpiece 2200 having a detachable head 2210. Handpiece 2200 has a handle 2220 coupled to a head 2210. Handle 2220 may be coupled to head 2210 using any known method of fastening. Preferably head 2210 includes optical components (e.g., head 1600 of FIG. 16A) to facilitate the use of replaceable components.

Figure 23:
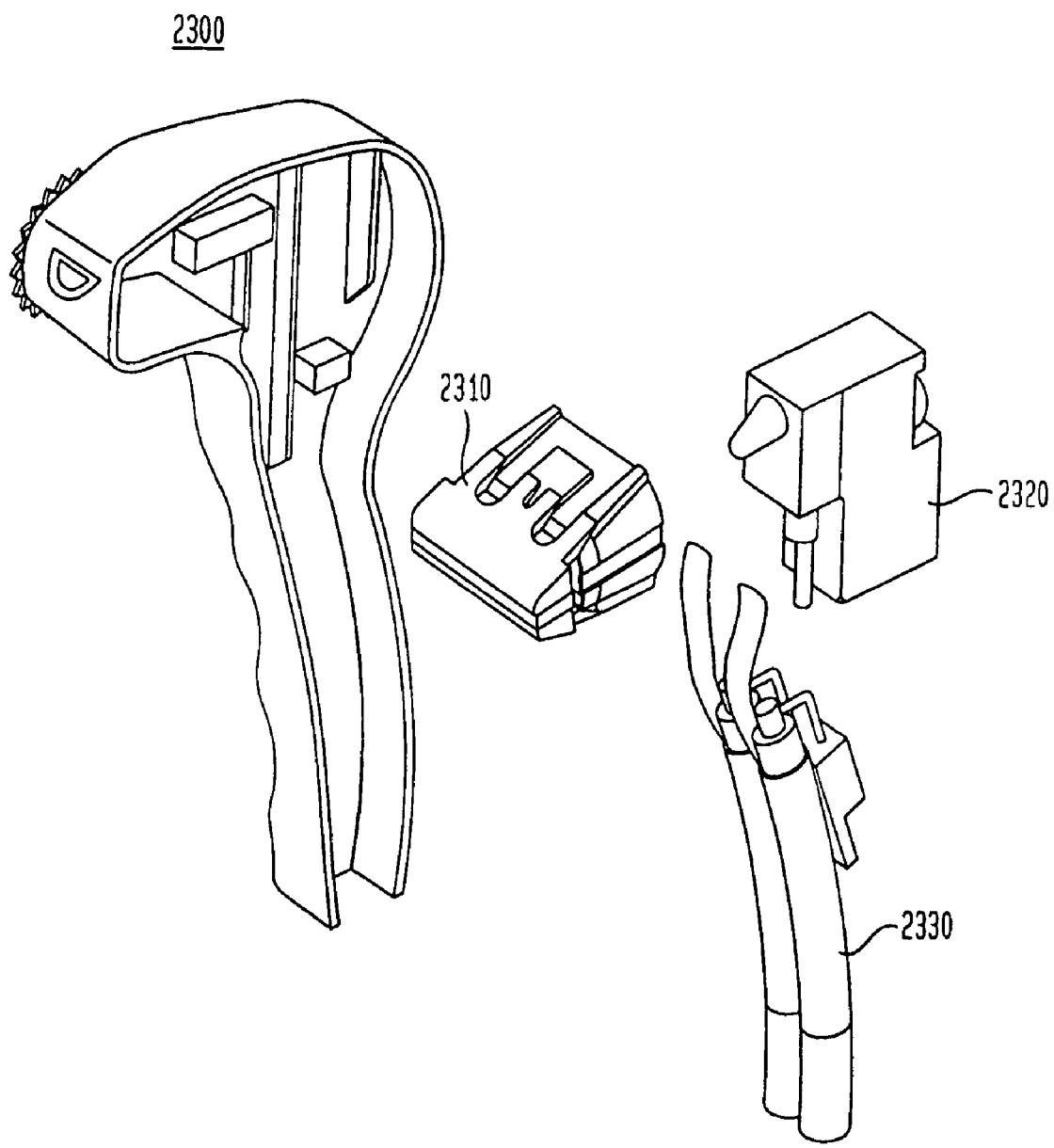
FIG. 23 is a schematic illustrating a modular handpiece having one or more components suitable for user-replacement.

FIG. 23 is a schematic of one example of an embodiment of a modular handpiece 2300 having one or more components suitable for ease of manufacturablity and/or user-replacement. For example, handpiece 2300 facilitates assembly and/or replacement of a head assembly 2310 (including an optical system), a cooling assembly 2320, and a power assembly 2330. Preferably, modular handpiece 2300 is configured such that when assembled, head assembly 2310 contacts a mating power plug of power assembly 2330.

Figure 24:
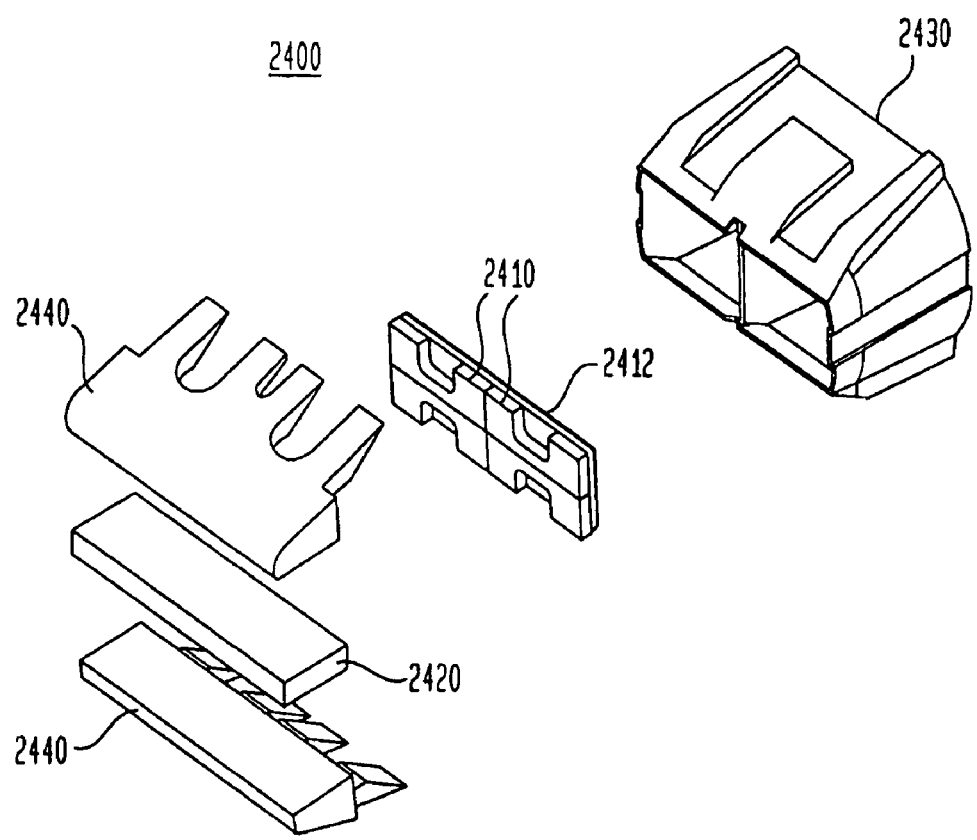
FIG. 24 is a schematic illustrating a modular optical assembly having one or more components suitable for user-replacement.

FIG. 24 is a schematic illustrating an optical assembly 2400 including a source 2410 (e.g., two diode-laser-bars). The source 2410 may be incorporated into a user-replaceable disposable cartridge, including electrodes 2412, heat sink 2430, optical system 2420 and coupling plates 2440. Coupling plates 2440 may be used to fasten optical system 2420, source 2410, and heat sink 2430. Preferably the fastening mechanism of source 2410 is configured to automatically align source 2410 to optical system 2420. Also preferably, coupling plates are made of a material having a good thermal conductivity (e.g., copper) to conduct heat from the optical system 2420. To simplify alignment of source 2410 and element 2420, source 2412 may be fixedly mounted to optical system 2420.

In addition to replacing the source 2410 at the end of its useable lifetime, it may also be desirable to facilitate the user-replacement of light sources 2410 for use for different cosmetic treatments without having to purchase multiple handpieces. Furthermore, it may be desirable to facilitate user-replacement of light sources 2410 based on skin type, hair type and/or on the location of the area of skin to be treated (e.g., underarm, bikini, leg, face).

Figure 25:
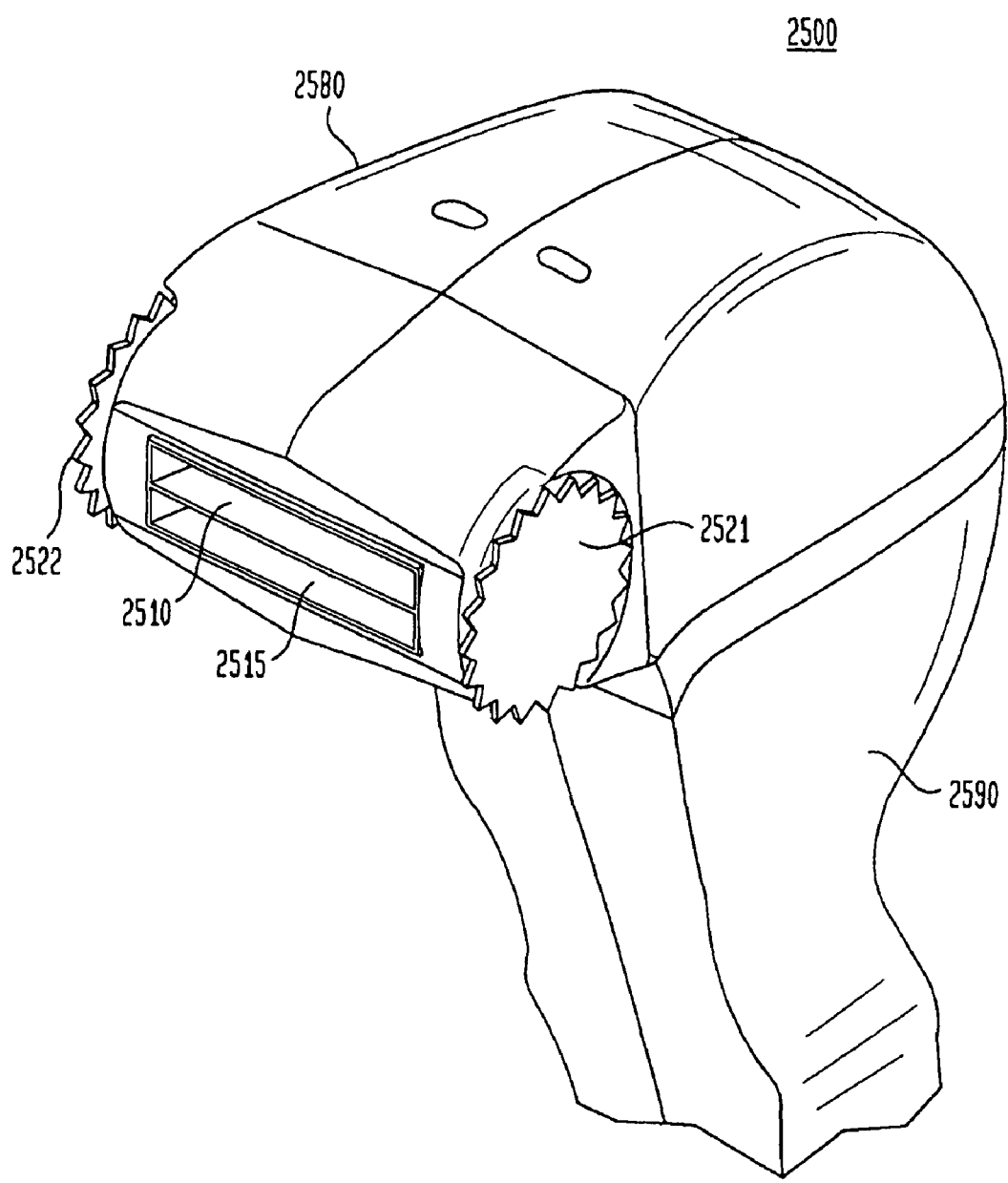
FIG. 25 is a schematic of one example of a photocosmetic device illustrating some aspects of the present invention.

FIG. 25 is a schematic of one example of a photocosmetic device 2500 illustrating some aspects of the present invention. Device 2500 has a head 2580 and a handle 2590. Head 2580 has a first optical system 2510 (e.g., optical system 310 in FIG. 3) to form a first area of radiation (e.g., area 311 in FIG. 3), and a second optical system 2515 (e.g., optical system 315 in FIG. 3) to form a second area of radiation (e.g., area 316 in FIG. 3) on a patient's skin. As described above with reference to FIG. 3, radiation to form the first area and the second area may be from a single divided source or two sources (sources not shown). Device 2500 also includes a motion sensor system having a wheel 2521 (e.g., corresponding to wheel 1821 of FIG. 18), and a second wheel 2522 (e.g., corresponding to wheel 1822 of FIG. 18) located on an opposite side of optical system 2510 to ensure that the entire skin contacting surface of the optical element 2510 moves at a rate of speed within the acceptable range to provide substantially uniform illumination on a patient's skin.

Figure 26A:
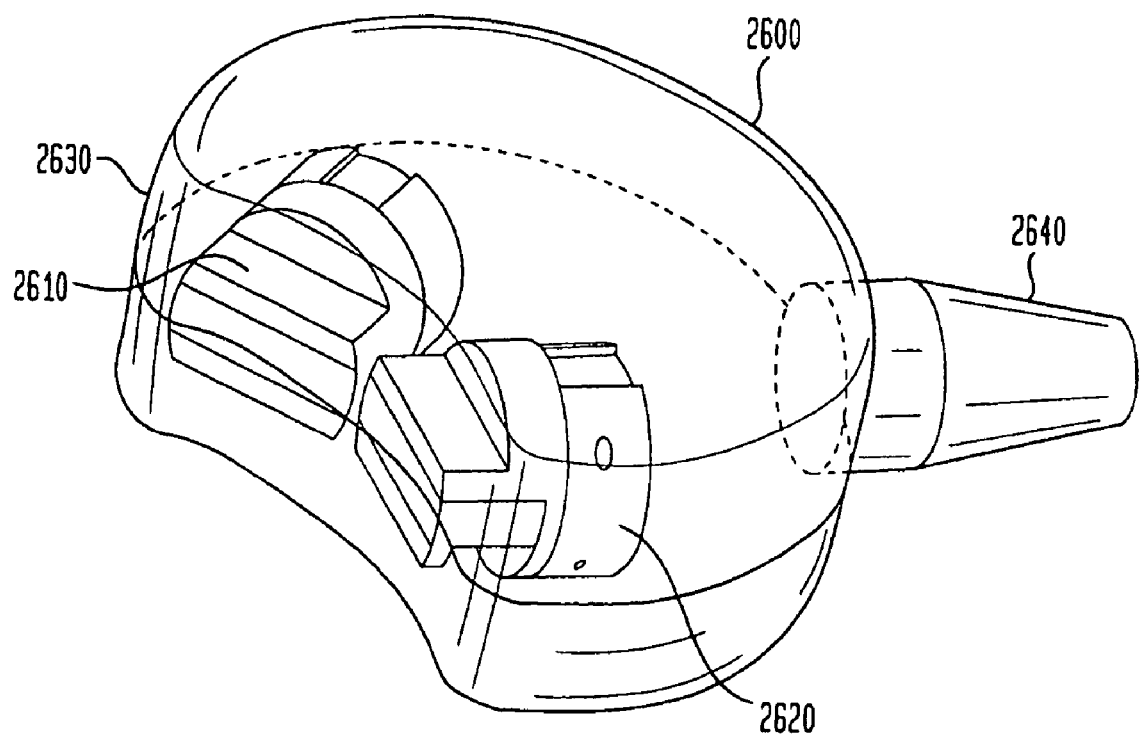
FIG. 26A is a schematic of one example of a photocosmetic head illustrating aspects of the present invention directed to treating a curved area of skin.

FIG. 26A is a schematic of one example of a photocosmetic head 2600 illustrating aspects of the present invention directed to a treating curved area of skin (e.g., a jaw, back or arm). Head 2600 includes two pivoting transmission systems 2610 and 2620 for delivering electromagnetic radiation. The components of head 2600 are substantially contained within a housing 2630 and coupled to a base unit (not shown) via cord 2640. Housing 2630 is illustrated as a transparent wire frame to facilitate description. The size of components of head 2600 may be selected according to the body part with which they are to be used, and multiple heads may be connectable to cord 2640 to permit treatment of various body parts. Alternatively, each head may have a fixed cord such that each cord can be plugged into a base unit and removed.

Figure 26B:
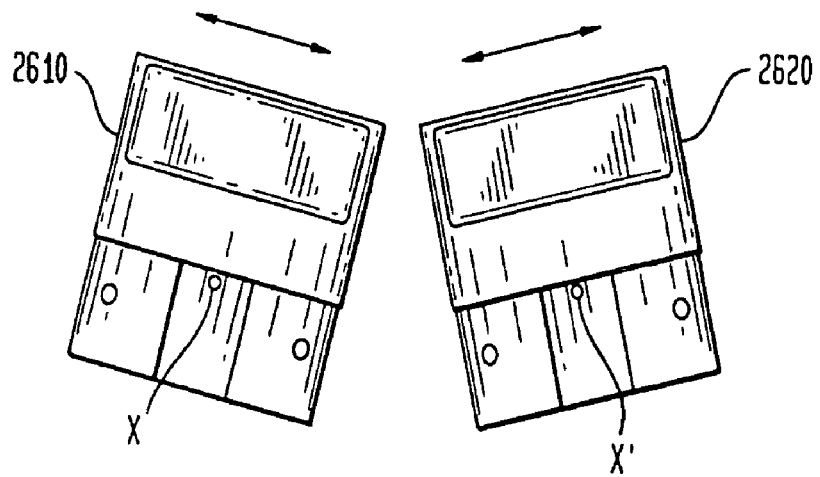
FIG. 26B is a schematic of one embodiment of two transmission systems of a head to treat a curved surface.

FIG. 26B is a schematic of one embodiment of two transmission systems 2610 and 2620 of a head to treat a curved surface. Transmission systems 2610 and 2620 are illustrated without a housing to illustrate there relative positioning. FIG. 26B illustrates that transmission systems pivot in at least one rotational direction to facilitate maintenance of contact with a curved area of skin. For example, transmission systems 2610 and 2620 may be mounted at an angle relative to one another (e.g., 5-30 degrees) and mounted to enable rotation about axis X and X'.

Figure 27:
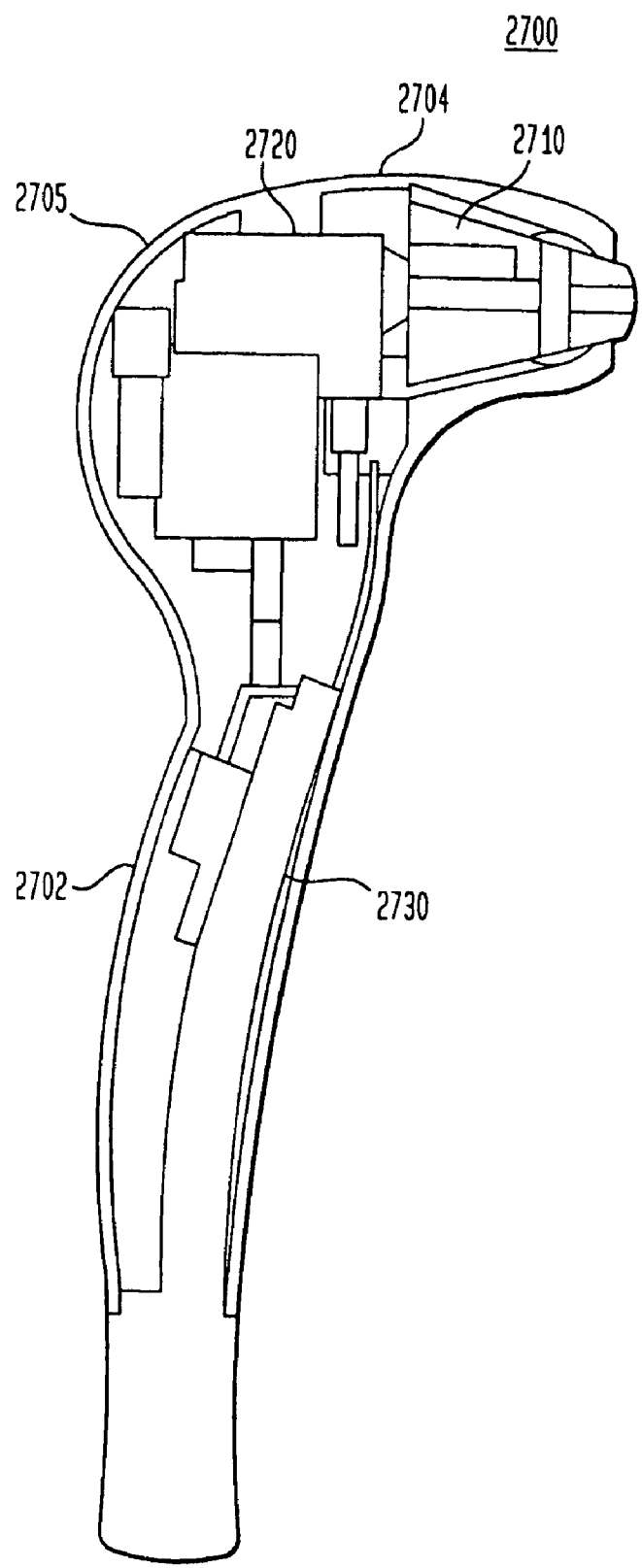
FIG. 27 is a schematic illustrating an embodiment of some aspects of handpiece 2700 according to the present invention.

FIG. 27 is a schematic illustrating an embodiment of some aspects of handpiece 2700 according to the present invention. Handpiece 2700 includes a housing 2710 having a handle 2702 and a head 2704. Handpiece 2700 includes a head assembly 2710 (including an optical system), a cooling assembly 2720, and a power assembly 2730.

Figure 28:
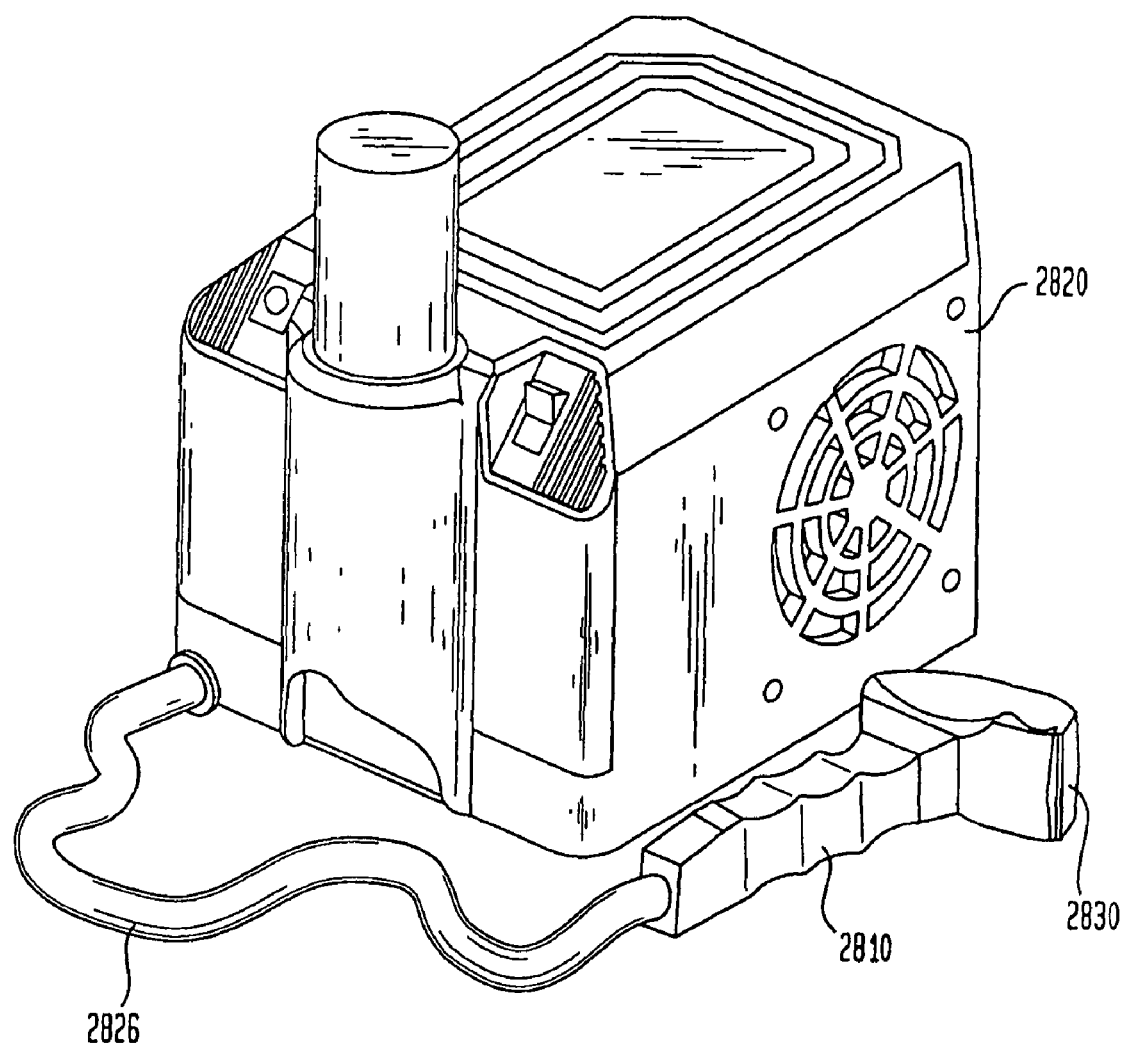
FIG. 28 is a schematic illustration of one embodiment of a photocosmetic device according to at least some aspects of the present invention.

FIG. 28 is a schematic illustration of one embodiment of a photocosmetic device 2800 according to at least some aspects of the present invention. Device 2800 includes a handpiece 2810, a base unit 2820, a cord 2826 to couple handpiece 2810 to base unit 2820. Handpiece 2810 may be grasped by an operator to move a head 2830 across a patient's skin (not shown). Head 2830 may be any head as described herein above or any other suitable head to achieve a photocosmetic treatment, for example, any of the treatments described below.

The following is a discussion of examples of treatments that can be achieved using apparatus and methods according the present invention; however, the treatments discussed are exemplary and are not intended to be limiting. Apparatus and methods according the present invention are versatile and may be applied to any known or yet-to-be-developed treatments.

Exemplary treatment mechanisms include absorption of light by a chromophore within a tissue responsible for the unwanted cosmetic condition or by a chromophore in proximity to the tissue. Treatment may be achieved by limited heating of the target tissue below temperature of irreversible damage or may be achieved by heating to cause irreversible damage (e.g., denaturation). Treatment may be achieved by direct stimulation of biological response to heat, or by induction of a cascade of phenomena such that a biological response is indirectly achieved by heat. A treatment may result from a combination of any of the above mechanisms. Optionally, cooling, DC or AC (RF) electrical current, physical vibration or other physical stimulus/action may be applied to a treatment area or adjacent area to increase the efficacy of a treatment. A treatment may result from a single session, or multiple sessions may be used to achieve a desired clinical effect.

A device according to one or more aspects of the invention may operate in a variety of optical ranges. For example, electromagnetic radiation delivered to the skin may have wavelength within the range 380-1900 nm. The power of the light delivered may be in the range 0.001-300 W/cm, and exemplary scan speeds include 0.1-500 mm/sec. The desired radiation characteristics may be achieved by any suitable LEDs, lamps, and diode lasers or any other suitable light source presently available or yet-to-be developed.

Radiation-induced hair removal is a cosmetic treatment that could be performed by apparatus and methods according to aspects of the present invention. In the case of hair removal, the principal target for thermal destruction is the hair bulb and preferably the hair matrix, hair papilla or basement membrane of the bulb. For hair removal treatments, melanin located in the hair shaft and follicle is the targeted chromophore. While the bulb contains melanin and can thus be thermally treated, the basement membrane, which provides the hair growth communication pathway between the papilla within the bulb and the matrix within the hair shaft, contains the highest concentration of melanin and may be selectively targeted.

Wavelengths between 0.6 and 1.2 μm are typically used for hair removal. By proper combination of power, speed, and focusing geometry, different hair related targets (e.g., bulb, matrix, basement membrane, stem cells) can be heated to the denaturation temperature while the surrounding dermis remains undamaged. Since the targeted hair follicle and the epidermis both contain melanin, a combination of epidermal contact cooling and long pulsewidth can be used to prevent epidermal damage. A more detailed explanation of hair removal is given in co-pending provisional patent application No. 60/363,871, entitled "METHOD AND APPARATUS FOR HAIR GROWTH CONTROL," by Rox Anderson, et al. filed Mar. 12, 2002, which is hereby incorporated herein by reference.

Hair removal is often required over large areas (e.g. back and legs), and the required power is therefore correspondingly large (on the order of 20-500 W) in order to achieve short treatment times. Current generation diode bars are capable of emitting 40-60 W at 800 nm, which makes them effective for use in some embodiments of photocosmetic device according to the present invention.

Exemplary methods of hair growth management may be achieved by combining low power irradiation of hair follicles with light and physical extraction of hair shaft, and/or complete or non-complete physical extraction of the hair follicle from the body. According to some embodiments irradiation is achieved by irradiating a portion of the skin containing the hair follicle with a light source emitting at a range of wavelengths absorbed by melanin or other endogenous or exogenous chromophores in the follicle. Physical extraction can be performed by mechanical, electromechanical or other suitable techniques. This treatment can be used for either temporary hair reduction or permanent hair reduction.

A first exemplary embodiment of a method of hair growth management according to the present invention includes first physically removing hair ("depilation") and then irradiating the skin as described above. According to some embodiments, the hair removal can be adjusted to remove mostly hair shafts from hair follicles; alternatively hair removal may be down to keratinoized zone. This depilation can be done by electromechanical depilation or waxing.

Phototreatment can be performed, for example, using one of the embodiments of photocosmentic device described above. According to these embodiments, light is absorbed by melanin in hair matrix and as a result of thermal injury hair growth is decelerated or completely arrested.

Optionally, after depilation but before irradiation, a topical lotion can be applied to the skin (e.g., via the handpiece) in a treatment area to fill empty hair follicles corresponding to the removed hair. In some embodiments, the transparent lotion is selected to have a refractive index in a range suitable to provide a waveguide effect to direct the light to a region of the skin to be irradiated. Preferably the index of refraction of the lotion is higher than the index of refraction of water (i.e., approximately 1.33 depending on chemical additives of the water). In some embodiments, the index of refraction of the lotion is higher than the index of refraction of the dermis (i.e., approximately 1.4). In some embodiments, the index of refraction of the lotion is higher than the index of refraction of the inner root sheath (i.e., approximately 1.55). In embodiments where the index of refraction is greater than the index of refraction of the inner root sheath, light incident on the surface of the skin can be delivered directly to hair matrix without significant attenuation.

The effective pulse length used to irradiate the skin is given by the beam size divided by the speed of scanning of the irradiation source. For example, a 2 mm beam size moved at a scanning speed of 50-100 mm/s provides an effective pulse length of 20-60 ms. For a power density of 250 W/cm the effective fluence is 5-10 J/cm$^2$, which approximately doubles the fluence of the light delivered by a device without the use of a high index lotion.

In some embodiments, the pH of the lotion can be adjusted to decrease the denaturation threshold of matrix cells. In such embodiments, lower power is required to injure the hair matrix and thus provide hair growth management. Optionally, the lotion can be doped by molecules or ions or atoms with significant absorption of light emitted by the source. Due to increased absorption of light in hair follicle due to the lotion, a lower power irradiation source may be used to provide sufficient irradiation to heat the hair matrix.

A second exemplary embodiment of a method of hair growth management according to the present invention includes first irradiating the skin, and then physically removing hair as described above. By first irradiating the skin, attachment of the hair shaft to the follicle or the hair follicle to dermis is weakened. Consequently, mechanical or electromechanical depilation may be more easily achieved (e.g., by using a soft waxing or electromechanical epilator) and pain may be reduced.

Irradiation can weaken attachment of hair bulb to skin or subcutaneous fat; therefore it is possible to pull out a significantly higher percentage of the hair follicle from the skin compared to the depilation alone. Because the diameter of the hair bulb is close to the diameter of the outer root sheath, pulling out hair with hair bulb can permanently destroy the entire hair follicle including stem cells. Accordingly, by first irradiating and then depilating, new hair growth can be delayed or terminated.

Treatment of cellulite is another example of a cosmetic problem that may be treated by apparatus and methods according to aspects of the present invention. The formation of characteristic cellulite dimples begins with poor blood and lymph circulation, which in turn inhibits the removal of cellular waste products. For example, unremoved dead cells in the intracellular space may leak lipid over time. Connective tissue damage and subsequent nodule formation occurs due to the continuing accumulation of toxins and cellular waste products.

The following are two exemplary treatments for cellulite, both of which aim to stimulate both blood flow and fibroblast growth. In a first exemplary treatment, localized areas of thermal damage are created using a treatment source emitting in the near-infrared spectral range (e.g., at a wavelength in the range 650-1850 nm) in combination with an optical system designed to focus 2-10 mm beneath the skin surface. In one embodiment, light having a power density of 1-100 W/cm is delivered to the skin surface, and the apparatus is operated at a speed to create a temperature of 45 degrees Celsius at a distance 5 mm below the skin. Cooling may be applied to avoid or reduce damage to the epidermis to reduce wound formation. Further details of achieving a selected temperature a selected distance below the skin is given in U.S. patent application Ser. No. 09/634,691, filed Aug. 9, 2000, the substance of which was incorporated by reference herein above. The treatment may include compression of the tissue, massage of the tissue, or multipasses over the tissue.

In a second exemplary treatment, a treatment source emitting near-infrared light (e.g., a light emitting diode emitting at a wavelength in the range 700-1300 nm) is used to focus the light a distance 2-10 mm beneath the skin surface, to elevate the dermis/subcutaneous fat temperature to a point well below the thermal damage threshold (e.g., a temperature in the range 42-60 degree Celcius). According to the second exemplary treatment, heating may increase the rate of lipolysis (i.e., fat breakdown) and cause apoptosis (i.e., programmed cell death) of fat cells. Optionally, a topical lipolytic cream may be used in combination with the second exemplary treatment; the elevated temperature profile in the dermis/subcutaneous fat may enhance cream penetration and thus increase its efficacy. Due to very long thermal relaxation time of subcutaneous fat (i.e., longer than 1 minute), multiple scanning treatments of an area can achieve the desired heating of the fat, while maintaining normal skin surface temperature. The above exemplary treatments may be used for fat metabolism activation and fat reduction.

Acne is another very common skin disorder that can be treated using apparatus and methods according to aspects of the present invention. Acne results when sebum from the sebaceous gland cannot reach the skin surface via the hair follicle, and a bacterial infection occurs within the hair follicle. Photocosmetic treatment is an alternative to traditional treatments (e.g., topical and oral medications).

The following are exemplary methods of treating acne according to the present invention. In each of the exemplary methods, the actual treated area may be relatively small (assuming treatment of facial acne), thus a low-power CW source may be used. A first possible treatment is to selectively damage the sebaceous gland to prevent sebum production. The sebaceous glands are located approximately 1 mm below the skin surface. By creating a focal spot at this depth and using a wavelength selectively absorbed by lipids (e.g., in proximity of 0.92, 1.2, and 1.7 μm), direct thermal destruction becomes possible. For example, to cause thermal denaturation, a temperature of 45-65 degrees Celsius may be generated at approximately 1 mm below the skin surface using any of the methods described in U.S. patent application Ser. No. 09/634,691, filed Aug. 9, 2000, the substance of which was incorporated by reference herein above.

Optionally, a linear matrix of focal spots (as described above with reference to FIG. 4) may be used to create islands of damage. Although the exact position of the sebaceous glands may not be known, each treatment with a matrix of focal spots will result in a certain number of sebaceous glands being damaged. Thus, by treating the area multiple times, a significant number of sebaceous glands will be damaged.

An alternative treatment for acne involves heating a sebaceous gland to a point below the thermal denaturation temperature (e.g., to a temperature 45-65 degrees Celsius) to achieve a cessation of sebum production and apoptosis (programmed cell death). Such selective treatment may take advantage of the low thermal threshold of cells responsible for sebum production relative to surrounding cells. Another alternative treatment of acne is thermal destruction of the blood supply to the sebaceous glands (e.g., by heating the blood to a temperature 60-95 degrees Celsius).

For the above treatments of acne, the sebaceous gland may be sensitized to near-infrared radiation by using compounds such as indocyanine green (ICG, absorption near 800 nm) or methylene blue (absorption near 630 nm). Alternatively, non-thermal photodynamic therapy agents such as photofrin may be used to sensitize sebaceous glands. In some embodiments, biochemical carriers such as monoclonal antibodies (MABs) may be used to selectively deliver these sensitization compounds directly to the sebaceous glands.

Although the above procedures were described as treatments for acne, because the treatments involve damage/destruction of the sebaceous glands (and therefore reduction of sebum output), the treatments may also be used to treat excessively oily skin.

Another light-based method of treating acne involves thermally destruction of the bacteria (P. acnes) responsible for the characteristic inflammation associated with acne. Destruction of the bacteria may be achieved by targeting porphyrins stored in P. Acnes Porphyrines, such as protoporphyrins, coproporphyrins, and Zn-protoporphyrins are synthesized by anaerobic bacteria as their metabolic product. Porphyrines absorbs light in the visible spectral region from 400-700 nm, with strongest peak of absorption around 415 nm. By providing light in the selected wavelength ranges in sufficient intensity heat resulting from absorption causes death of the bacteria. For example, the desired effect may be achieved using a treatment source emitting at a wavelength in the range 360-700 nm using an optical system designed to focus 0.2-1 mm beneath the skin surface and a power density of 0.01-10 W/cm at the skin surface.

Yet another technique for treating acne involves using light to expand the opening of an infected hair follicle to allow unimpeded sebum outflow. In one embodiment of the technique, a lotion that preferentially accumulates in the follicle opening (e.g., lipid consistent lotion with organic non organic dye or absorbtion particles) is applied to the skin surface. A treatment source wavelength is matched to an absorption band of the lotion. For example, in the case of ICG doped lotion the source wavelength is 790-810 nm. By using an optical system to generate a temperature of 45-100 degrees Celsius at the infundibulum/infrainfundibulum, for example, by generating a fluence of at skin surface (e.g., 1-100 W/cm), the follicle opening can be expanded and sebum is allowed to flow out of the hair follicle and remodeling of infrainfundibulum in order to prevent comedo (i.e., blackhead) formation.

Non-ablative wrinkle treatment, which is now used as an alternative to traditional ablative $CO_2$ laser skin resurfacing, is another cosmetic treatment that could be performed by apparatus and methods according to aspects of the present invention. Non-ablative wrinkle treatment is achieved by simultaneously cooling the epidermis and delivering light to the upper layer of the dermis to thermally stimulate fibroblasts to generate new collagen deposition.

In wrinkle treatment, because the primary chromophore is water, wavelengths ranging from 0.8-2 μm appropriate wavelengths of treatment radiation. Since only wrinkles on the face are typically of cosmetic concern, the treated area is typically relatively small and the required coverage rate ($cm^2/sec$) is correspondingly low, and a relatively low-power treatment source may be used. An optical system providing sub-surface focusing in combination with epidermal cooling may be used to achieve the desired result. Precise control of the upper-dermis temperature is important; if the temperature is too high, the induced thermal damage of the epidermis will be excessive, and if the temperature is too low, the amount of new collagen deposition will be minimal. A speed sensor (in the case of a manually scanned handpiece) or a mechanical drive may be used to precisely control the upper-dermis temperature. Alternatively, a non-contact mid-infrared thermal sensor could be used to monitor dermal temperature.

Vascular lesions (e.g. port-wine stains, rosacea, spider veins) present another cosmetic problem that could be treated by apparatus and methods according to aspects of the present invention. For treatment of vascular lesions, the target chromophore is blood in these lesions. Exemplary treatment wavelengths range from 0.4-0.6 μm for superficial vascular lesions and 0.6-1.3 for deep vascular lesions. In the case of treatment of spider veins, the relatively large size and corresponding long thermal relaxation time of the target tissue requires a large deposition of energy over a long time period to achieve thermal destruction and to preserve the epidermis. In addition, aggressive epidermal cooling (particularly for patients with darker skin type IV-VI) can be used to prevent epidermal damage. The use of CW sources is advantageous in the treatment of lesions because, similar to hair removal, part of the targeted structure (vein wall) contains little blood and must be damaged by thermal diffusion.

Pigmented lesions such as age spots can be removed by selectively targeting the cells containing melanin in these structures. These lesions are located using an optical system focusing at a depth of 100-200 μm below the skin surface and can be targeted with wavelengths in the 0.4-1.1 μm range. Since the individual melanin-bearing cells are small with a short thermal relaxation time, a shallow sub-surface focus is helpful to reach the denaturation temperature.

Elimination of underarm odor is another problem that could be treated by an apparatus and methods according to aspects of the present invention. In such a treatment, a source having a wavelength selectively absorbed by the eccrine/apocrine glands is used to thermally damage the eccrine/apocrine glands. Optionally, a sensitization compound may be used to enhance damage.

Tattoo removal is another procedure that can be achieved by apparatus and methods according to aspects of the present invention. Conventional devices for tattoo removal include short pulsed (10-50 ns) Q-switched ruby, alexandrite, Nd:YAG and frequency-doubled Nd:YAG for cosmetic tattoo removal. Typically, a source wavelength is selected based on the color of the tattoo to be removed (e.g., a green laser is used to remove a red portion of a tattoo). Since the ink particles are actually incorporated into individual cells, one embodiment of a thermal treatment for tattoo removal cause the rupture of the cells, thereby releasing the ink.

Exemplary embodiments of apparatus according to aspects of the present invention for use in tattoo removal use a CW source, and an optical system selected to tightly focus radiation from a treatment source at the depth where the cells containing the ink particles reside (e.g., 150-700 μm) to rupture the ink-containing cells. Alternatively, it may also be possible to heat the cells below their thermal denaturation point and induce apoptosis. In the case of embodiments designed to cause apoptosis, healing may be enhanced by operating the radiation source in a quasi-continuous mode while the handpiece is continuously scanned across the skin surface to create areas in which cells are damaged and areas of non-irradiated areas in between. In some embodiments, feedback from a speed sensor could be used to control laser emission and create equally spaced lines of damage independent of handpiece speed. To completely remove the tattoo, multiple treatments would be required.

In some conventional, relatively expensive tattoo-removal apparatus, a Q-switched frequency-doubled Nd:YAG laser emitting at 0.532 µm is combined with an (Nd:YAG) emitting at 1.064 µm, and alexandrite laser emitting at 0.755 µm; the lasers are selectively operated to target cells containing various tattoo ink colors. Embodiments of modular apparatus according to aspects of the present invention, provide a relatively low-cost alternative to the above system. For example, an embodiment of the present invention may be configured to allow the use of optical sources emitting at distinct wavelengths or wavelength bands or a single source and optical components to modify the wavelength of the light generated by a source. In particular, to achieve a wavelength close to the 0.755 µm wavelength, a 0.808 µm diode laser bar may be used; and a Nd:YAG crystal module could be inserted into the handpiece that would be pumped by the diode laser bar to produce a wavelength close to the 1.064 µm wavelength; and to produce a wavelength close to the 0.532-µm wavelength, an SHG crystal may be used to double the frequency of a laser diode emitting 1.064 µm wavelength radiation. Alternatively, a self-frequency-doubling crystal such as Nd:YCOB may be used.

Low-intensity therapy (LIT) is another procedure that can be achieved by apparatus and methods according to aspects of the present invention. LIT may be used to for treatment of wounds, carpal-tunnel syndrome treatment, or to stimulate hair growth, or to accelerate biochemical reactions. Power densities and wavelengths (630-820 nm) typically used for LITs may be achieved using diode lasers or LED treatment sources. Optionally one or more of the above treatments may be used for veterinary LIT applications.

Elimination of or reduction of the prominence of stretch marks and scars are procedures that may be achieved using apparatus and methods according to aspects of the present invention. Similar to the case of non-ablative skin resurfacing, to achieve the above procedures, it may be possible to stimulate collagen deposition and wound healing by creating a thin thermally damaged layer in the upper dermis.

Removal of warts is another procedure that can be achieved using apparatus and methods according to aspects of the present invention. Wart removal may be achieved using a source producing light in the region of blood absorption (0.5-0.8 µm). This wavelength is selectively absorbed by hemoglobin, which appears to shuts off the wart's blood supply.

Psoriasis is skin disorder that can be treated using apparatus and methods according to aspects of the present invention. Exemplary, embodiments of the present invention configured to treat psoriasis emit at wavelengths near 800 nm. Optionally, one or more sensitization agents such as photodynamic drugs or ICG/Methylene blue may be used. Treatment may be applied several times per week, and may be delivered in several different ways including islands (or lines) of treatment. Additional application of apparatus and methods according to aspects of the present invention include facilitation of delivery of topical medications and cosmetic preparations into skin.

Having thus described the inventive concepts and a number of exemplary embodiments, it will be apparent to those skilled in the art that the invention may be implemented in various ways, and that modifications and improvements will readily occur to such persons. Thus, the examples given are not intended to be limiting. The invention is limited only as required by the following claims and equivalents thereto. The invention is limited only as required by the following claims and equivalents thereto. Also, it is to be understood that the use of the terms "including," "comprising," or "having" is meant to encompass the items listed thereafter and equivalents thereof as well as additional items before, after, or in-between the items listed.

What is claimed is:

1. A dermatologic treatment apparatus that is cordless and sufficiently compact as to be hand-held, comprising: a self-contained housing configured for gripping by a person's hand for cordless manipulation in a dermatologic treatment procedure; a light source comprising one or more diode laser bars within the housing; an electrical circuit within the housing comprising one or more batteries and an electronic control circuit for energizing the light source to produce output light pulses; a light path within the housing including an aperture through which the output light pulses are propagated out of the housing having properties that provide efficacious treatment; and a heatsink for contacting a region of an epidermis of a person undergoing treatment, having one or more thermal characteristics that serve to remove heat from the epidermis, and wherein the temperature of the heatsink is maintained below a normal skin temperature, wherein a normal skin temperature is a temperature of the skin when not being treated with the device; wherein the cordless apparatus has a total weight and volume such that it is able to be hand-held.

2. The apparatus of claim 1, wherein the heatsink comprises a sapphire output window.

3. A dermatologic hair-regrowth-inhibiting apparatus that is cordless and sufficiently compact as to be hand-held, comprising: a self-contained housing configured for gripping by a person's hand for cordless manipulation in a hair-regrowth-inhibiting procedure; a light source comprising one or more diode laser bars within the housing; a direct drive electrical circuit within the housing comprising one or more batteries for energizing the light source to produce output light pulses; a light path within the housing including an aperture through which the output light pulses are propagated out of the housing having properties sufficient for at least temporary hair-regrowth inhibition; and a heatsink for contacting a region of an epidermis of a person undergoing treatment, having one or more thermal characteristics that serve to remove heat from the epidermis, and wherein the temperature of the heatsink is maintained below a normal skin temperature, wherein a normal skin temperature is a temperature of the skin when not being treated with the device.

4. The apparatus of claim 3, wherein the heatsink comprises a sapphire output window.

5. A dermatologic hair-regrowth-inhibiting apparatus that is cordless and sufficiently compact as to be hand-held, comprising: a self-contained housing configured for gripping with a person's hand for cordless manipulation in a hair-regrowth-inhibiting procedure; a light source within the housing containing one or more diode lasers; an electrical circuit within the housing comprising one or more batteries and an electronic control circuit for energizing the light source to produce output light pulses; a light path within the housing including an aperture through which the output light pulses are propagated out of the housing; and wherein a peak power, a pulse duration of a light pulse emitted by the apparatus, an output fluence of a light pulse emitted by the apparatus and a majority of the energy of a light pulse emitted by the apparatus are sufficient such that the light pulses propagated out of the housing inhibit hair-regrowth; and a heatsink for contacting a region of an epidermis of a person undergoing treatment, having one or more thermal characteristics that serve to remove heat from the epidermis, and wherein the temperature of the heatsink is maintained below a normal skin temperature, wherein a normal skin temperature is an average temperature of the skin when not being treated with the device.

6. The apparatus of claim 5, wherein the heatsink comprises a sapphire output window.

7. A dermatologic hair-regrowth-inhibiting apparatus that is cordless and sufficiently compact as to be hand-held, comprising: a self-contained housing configured for gripping by a person's hand for cordless manipulation in a hair-regrowth-inhibiting procedure; a light source within the housing comprising one or more diode lasers a direct drive electrical circuit within the housing comprising one or more batteries for energizing the light source to produce output light pulses; a light path within the housing including an aperture through which the output light pulses are propagated out of the housing; and wherein a peak power, a pulse duration of a light pulse emitted by the apparatus, an output fluence of a light pulse emitted by the apparatus and a majority of the energy of a light pulse emitted by the apparatus are sufficient such that the light pulses propagated out of the housing inhibit hair-regrowth; and wherein the cordless apparatus has a total weight and volume such that it is able to be hand-held; light pulses are emitted at a pulse repetition frequency sufficient to produce lines of light at the skin surface to inhibit hair-regrowth; and a heatsink for contacting a region of an epidermis of a person undergoing treatment, having one or more thermal characteristics that serve to remove heat from the epidermis, and wherein the temperature of the heatsink is maintained below a normal skin temperature, wherein a normal skin temperature is a temperature of the skin when not being treated with the device.

8. The apparatus of claim 7, wherein the heatsink comprises a sapphire output window.

9. A dermatologic treatment apparatus that is cordless and able to be hand-held, comprising: a self-contained housing configured for grasping by a person's hand for cordless manipulation in a dermatologic treatment procedure; a light source comprising one to three diode laser bars within the housing; an electrical power source within the housing comprising one or more batteries and an electronic control for energizing the light source to produce output light pulses; a light path within the housing including an aperture through which the output light pulses are propagated out of the housing having properties that provide efficacious treatment; and a heatsink for contacting and cooling a region of an epidermis of a person undergoing treatment, by removing heat from the epidermis; wherein the cordless apparatus is of a size such that it may be hand-held.

10. The apparatus of claim 9, wherein the heatsink comprises a sapphire output window.

11. A dermatologic hair-growth-reduction apparatus that is cordless and able to be hand-held, comprising: a self-contained housing configured for grasping by a person's hand for cordless manipulation in a hair-growth-reduction procedure; a light source comprising one to three diode laser bars within the housing; an electrical power source within the housing comprising one or more batteries for energizing the light source to produce output light pulses; a light path within the housing including an aperture through which the output light pulses are propagated out of the housing to a patient's skin having properties sufficient for at least temporary hair-growth reduction; and a heatsink for contacting a region of skin of a person undergoing treatment, and removing heat from the skin, and wherein the temperature of the heatsink is maintained below a normal skin temperature, wherein a normal skin temperature is a temperature of the skin when not being treated with the device.

12. The apparatus of claim 11, wherein the heatsink comprises a sapphire output window.

13. A dermatologic hair-growth-reducing apparatus that is cordless and able to be hand-held, comprising: a self-contained housing configured for grasping with a person's hand for cordless manipulation in a hair-growth-reducing procedure; a light source within the housing containing one to three diode lasers; an electrical power source within the housing comprising one or more batteries and a control for energizing the light source to produce output light pulses; a light path within the housing including an aperture through which the output light pulses are propagated out of the housing to the patient's skin surface; and wherein a peak power of a light pulse emitted by the apparatus is between 0.001-300 W/cm; a pulse duration of a light pulse emitted by the apparatus is between 20 and 60 milliseconds; an output fluence of a light pulse emitted by the apparatus is between 5 J/cm$^2$ and 10 J/cm$^2$; a majority of the energy of a light pulse emitted by the apparatus is contained within a spectral band of 790 nm to 900 nm; and a heatsink for contacting a region of skin of a person undergoing treatment, and removing heat from the skin, and wherein the temperature of the heatsink is maintained below a normal skin temperature, wherein a normal skin temperature is a temperature of the skin when not being treated with the device.

14. The apparatus of claim 13, wherein the heatsink comprises a sapphire output window.

15. A dermatologic hair-growth-reduction apparatus that is cordless and able to be hand-held, comprising: a self-contained housing configured for grasping by a person's hand for cordless manipulation in a hair-regrowth-inhibiting procedure; a light source within the housing comprising one to three diode laser bars an electrical power source within the housing comprising one or more batteries for energizing the light source to produce output light pulses; a light path within the housing including an aperture through which the output light pulses are propagated out of the housing; and wherein a peak power of a light pulse emitted by the apparatus is between 0.001-300 W/cm; a pulse duration of a light pulse emitted by the apparatus is between 20-60 milliseconds; an output fluence of a light pulse emitted by the apparatus is between 5 J/cm$^2$ and 10 J/cm$^2$; a majority of the energy of a light pulse emitted by the apparatus is contained within a spectral band of 790 nm to 900 nm; the cordless apparatus having a size such that it may be hand-held; wherein the lines of light emitted to the skin surface have a length of 1-300 mm and a width of 0.1-10 mm; and a heatsink for contacting a region of skin of a person undergoing treatment, and removing heat from the skin, and wherein the temperature of the heatsink is maintained below a normal skin temperature, wherein a normal skin temperature is a temperature of the skin when not being treated with the device.

16. The apparatus of claim 15, wherein the heatsink comprises a sapphire output window.

* * * * *

UNITED STATES PATENT AND TRADEMARK OFFICE
CERTIFICATE OF CORRECTION

PATENT NO.       : 8,182,473 B2
APPLICATION NO.  : 11/603712
DATED            : May 22, 2012
INVENTOR(S)      : Gregory B. Altshuler et al.

Page 1 of 1

It is certified that error appears in the above-identified patent and that said Letters Patent is hereby corrected as shown below:

On the Title Page in the Related U.S. Application Data:

Item (63) should read:

Continuation of application No. 10/154,756, filed on May 23, 2002, now Pat. No. 7,204,832, and a continuation-in-part of application No. 10/052,474, filed on Jan. 18, 2002, now Pat. No. 6,663,620, which is a continuation of application No. 09/473,910, filed on Dec. 28, 1999, now Pat. No. 6,517,532, ~~and a continuation in part of application No. 09/078,055, filed on May 13, 1998, now Pat. No. 6,273,884,~~ and said application No. 10/154,756, filed May 23, 2002, now Patent No. 7,204,832, ~~which~~ is a continuation-in-part of application No. 09/268,433 filed on Mar. 12, 1999, now Pat No. 6,508,813, ~~which is a continuation-in-part of application No. 08/759,036, filed on Dec. 2, 1996, now Pat No. 6,015,404, and a continuation in part of application No. 08/759,136 filed on Dec. 2, 1996, now abandoned, which is a continuation-in-part of application No. 09/634,981, filed on Aug. 9, 2000, now Pat. No. 6,511,475,~~ and ~~which~~ is a continuation-in-part of application No. 09/847,043, filed on Apr. 30, 2001, now Pat. No. 6,653,618.

Item (60) should read:

Provisional application No. 60/363,798, filed on Mar. 12, 2002, provisional application No. 60/115,447, filed on Jan. 8, 1999, provisional application No. 60/164,492, filed on Nov. 9, 1999, ~~provisional application No. 60/046,542, filed on May 15, 1997, provisional application No. 60/077,794, filed on Jan. 8, 1999, provisional application No. 60/077,726, filed on Mar. 12, 1998,~~ provisional application No. 60/200,431, filed on Apr. 28, 2000, provisional application No. 60/292,827, filed on May 23, 2001, provisional application No. 60/363,871, filed on Mar. 12, 2002.

Signed and Sealed this
Twenty-fourth Day of July, 2012

David J. Kappos
*Director of the United States Patent and Trademark Office*